(12) United States Patent
Chaudhary et al.

(10) Patent No.: US 7,642,346 B2
(45) Date of Patent: Jan. 5, 2010

(54) FLAX SEED SPECIFIC PROMOTERS

(75) Inventors: Sarita Chaudhary, Calgary (CA); Gijs Van Rooijen, Calgary (CA); Maurice M. Moloney, Calgary (CA); Surinder Singh, Downer (AU)

(73) Assignees: Sembiosys Genetics Inc., Calgary (CA); Commonwealth Scientific and Industrial Research Organization (CSIRO), Campbell (AU)

( * ) Notice: Subject to any disclaimer, the term of this patent is extended or adjusted under 35 U.S.C. 154(b) by 331 days.

(21) Appl. No.: 10/804,219

(22) Filed: Mar. 19, 2004

(65) Prior Publication Data
US 2004/0255350 A1 Dec. 16, 2004

Related U.S. Application Data

(63) Continuation-in-part of application No. 09/645,593, filed on Aug. 25, 2000, now Pat. No. 6,777,591.

(60) Provisional application No. 60/151,044, filed on Aug. 27, 1999, provisional application No. 60/161,722, filed on Oct. 27, 1999.

(51) Int. Cl.
*C12N 15/82* (2006.01)
(52) U.S. Cl. ............... 536/24.1; 435/320.1; 800/278; 800/281; 800/298
(58) Field of Classification Search ............... None
See application file for complete search history.

(56) References Cited

U.S. PATENT DOCUMENTS
6,777,591 B1 * 8/2004 Chaudhary et al. ......... 800/298

FOREIGN PATENT DOCUMENTS
WO     WO 98/18948     * 5/1998

OTHER PUBLICATIONS

Chamberland et al 1992, Plant Molecular Biology, 19:937-949.*
Donald et al 1990, EMBO J. 9:1717-1726.*
Shen et al 1995, The Plant Cell 7: 295-307.*
Hobo et al 1999, Proc. Natl. Acad. Sci. USA 96(26): 15348-15353.*
Bobb et al 1997, Nucleic Acids Research 25(3): 641-647.*
Reidt et al 2000, The Plant Journal 21(5): 401-408.*
Reda Helmy Sammour et al., "Proteins of linseed (*Linum usitatissimum* L.), extraction and characterization by electrophoresis", Bot. Bull. Acad. Sin. (1999) 40: 121-126.
Jeffry R. Borgmeyer et al., "Isolation and Characterization of a 25 kDa Antifungal Protein From Flax Seeds", Biochemical and Biophysical Research Communications, vol. 187, No. 1, 1992, Aug. 31, 1992 pp. 480-487.
G.R. Reeck et al., ""Homology" in Proteins and Nucleic Acids: A Terminology Muddle and a Way Out of It", Cell, vol. 50, 1987, p. 667.
Robert G.K. Donald et al., "Mutation of either G box or I box sequences profoundly affects expression from the *Arabidopsis* rbcS-1A promoter", The EMBO Journal, vol. 9, No. 6, 1990, pp. 1717-1724.
Sylvain Chamberland et al., "The legumin boxes and the 3' part of a soybean β-conglycinin promoter are involved in seed gene expression in transgenic tobacco plants", Plant Molecular Biology, vol. 19, 1992, pp. 937-949.

* cited by examiner

*Primary Examiner*—David H Kruse
(74) *Attorney, Agent, or Firm*—Stephen A. Bent; Foley & Lardner LLP

(57) ABSTRACT

Novel methods for the expression of non-native genes in flax seeds and the seeds of other plant species are provided. The methods involve the use of seed-specific promoters obtained from flax. Additionally provided are novel flax seed-specific promoters, chimeric nucleic acid constructs comprising novel flax seed-specific promoters, transgenic plant cells, transgenic plants and transgenic plant seeds containing novel flax seed-specific promoters. The promoters and methods are useful, for example, for altering the seed oil and protein composition in flax seed or other plant seeds.

16 Claims, 24 Drawing Sheets

FIGURE 1-1

```
   1  ttcaaaacccgattcccgaggcgccctattgaagatatgggggaagttcgacgagatcgatgtcgggtcgagtgctatg    80
  81  gtgatggtgccgtttggggggaggatgagcgagatagccaagactagcattccgttcccacacagagttggaatttgta   160
 161  ccaaatccaacactgtcgtattggagcgacgataggggacgcggaaaaacacatccgttggatcagggagttgtacgatg   240
                    R1
 241  atctcgagccttatgtgtcgaagaatccgagtatgctacgtgaactacagggatctcgacatcgggatgaatggagga    320
 321  ggtgaaggggatgagaagggtacttatgtgaggctaaggtgtggggggagaagtactttgggtgtcaactttgatcggtt   400
                                                                            R2
 401  ggttcgggtgaagacgattgttgatcccaataatgtgtttcgaaacgagcagagcattccctcaattccaactcggttat   480
 481  aaggatcaatgatcaatgagaatttcctttccaatgtgattacaagttctatttggtgtcagcttctcaactgctcctat   560
 561  tcatttagattaattcataacaactattaattaccagcctttatccgcccgttggccgattaatttctttaagtttt     640
 641  agatgaaatgaaaccgattagttttttattgagatgagattaatcttgcttgaaattactcacgttgatgtga         720
 721  tatttggaattaactaaaatgataaatatcggataaaaatattaaaataataacataagaacaata                800
              I1                                                          R4
 801  aaataaataatttaatttattcccttgtttcttctgtatcatacatctctctcttacttcttaaaggctt            880
           R4                R3
 881  ttcaattatcacttaattaaataatacaaatcgttaattctataacattaacctatacacttgcacggtgaacaat      960
 961  caatatgataataatataataataattcaattattaatctacaattttttaattataaagtttatgcggtcagtt      1040
                                                                              R5
1041  tctgcaagctccgagctccttgtcatcgttagttttctgcggtctcaaggtataacgactcggagcgacgagcccttgct  1120
                                                                              R1
1121  tccaatgacgggttgcattctgccgtcgttgagctcgattggcgtgtcatgctggagtctcagagttcctacaaaaaaac  1200
1201  cctaaactagagggtgattagggtgaaattaggggtgaaatttaggtgttggcctggttccattgtccaaagtttagtcaacttaaaaac  1280
1281  agacttaaatttatgcttcaaatagtttatctgttattatattagcgtgtaattagtcttgacaatgggccgacgg     1360
```

FIGURE 1-2

```
1361 gtacggattcggagacccgatcccgccatagtgtaatggctcaactgccaagtcagcattggaccgaaattattggac 1440
1441 acgaagtactaatgtgaaaaacttacatttgttatttctacttttaatactatgctatttcaaaatttgaacttaat 1520
                                                                              R6
1521 actatgttttatatagttagtatcttaattttatgcaaattcatctaattgtataactatttcgatccgtag 1600
     ─────                                                                R3
1601 ctaattatttcgaaggcaagtcaaagtgttattgtggactatgtgagctaatattgaaccttatctctcccaaccactc 1680
1681 aagttaattgaaccaaactcgatcggttgggtttcgagctatttcgagccattgttgttatatgcacgtgagatatcaag 1760
                               R2
1761 attgacccgaacactttattatgataatgtagaaaaagaaacatattctaagactacatgcatgcaaagtcaaccct 1840
                            I2
1841 gcatggaaagctgctcaacacgtggcatagactcccgcacgtgtccattccacctcatcacctcaccccaccgttcac 1920
     ─────── ────
     CACA    ABRE
1921 ctcttattatatcacaacaatcaatcctactcctccatactcgaacaaatccgaccaacttatacaatattccca 2000
     ────────                                                          ────
     R5                                                                CAT
     TATA
2001 aacttgattaattctcagcaat ATG GAT CAG ACG CAC CAG ACA TAC GCC GGA ACC ACG CAG AAC 2065
  1                        M   D   Q   T   H   Q   T   Y   A   G   T   T   Q   N    14

2066 CCG AGC TAT GGC GGG GGC ACA ATG TAC CAG CAG CAG CCG AGG TCT TAC CAG GCG 2125
 15   P   S   Y   G   G   G   T   M   Y   Q   Q   Q   P   R   S   Y   Q   A    34

2126 GTG AAG GCG GCC ACT GCA GCC ACC GCG GGT GGA TCC CTC ATC GTT CTG TCC CTC ATC 2185
 35   V   K   A   A   T   A   A   T   A   G   G   S   L   I   V   L   S   L   I    54

2186 CTT ACG GCC ACC GTC ATT TCA CTC ATC ATA GCC ACC CCT CTC CTT GTC ATC TTC AGC CCT 2245
 55   L   T   A   T   V   I   S   L   I   I   A   T   P   L   L   V   I   F   S   P    74

2246 GTT CTT GTC CCG GCT CTC ATC ACC GTC GGG CTC TTG ATC ACC GGG TTT CTT GCT TCC GGT 2305
 75   V   L   V   P   A   L   I   T   V   G   L   L   I   T   G   F   L   A   S   G    94

2306 GGG TTC GGA GTC GCC GCC GTC ACC GTC TTG TCC TGG ATC TAT AG gtatgtataagctttggactt 2370
 95   G   F   G   V   A   A   V   T   V   L   S   W   I   Y   R                        109

2371 tagtattgttataaatacataagctgatttatgaacatgatcccaacaagagttatttaaatgcattctcggtctg 2450
```

FIGURE 1-3

```
2451 actcgatcggttgggtttgagctactcggtcacaatgtcgggtcggctctgatctgttatactaatatttggaagcc 2530

2531 tgaagttcattgttctgcccaacttcccactacctttgagggtgtgacggttctctataaacattcgaaatctttgttcaattatgaatccct 2610

2611 cccaacaactcagaactcgagtcagtgggtgtgacggttctctataaacattcgaaatctttgttcaatgaacgtag 2690

2691 aaatgaccatgctgatgattgtgggtcttataag G TAC GTG ACC GGC GGG CAC GCG GGA GGG 2756
                                        Y   V   T   G   G   H   P   A   G   G   119

2757 GAT TCG CTG GAC CAG GCT AGG TCG AAG CTG GCC GGA AAG GCC AGG GAG GTG AAG GAC AGG 2816
 120 D   S   L   D   Q   A   R   S   K   L   A   G   K   A   R   E   V   K   D   R   139

2817 GCG TCG GAG TTC GCA CAG CAG CAT GTC ACA GGT GGT CAA CAG ACC TCT TAA agagagtcctct 2879
 140 A   S   E   F   A   Q   Q   H   V   T   G   G   Q   Q   T   S   *               156

2880 agttaaattggtctctcgttctgttcgtgcggcttgtaaactctctttaagtgtgctgtttcctttgtctcgtgt 2959

2960 gttgtaagtgaaagtgtaatcgaagttccaagttggagatgtttgtaacgatgatgtttctaataatcagagatattaa 3039
                                                                        Poly A signal 3040 aagggttgctaatttagtattgcgtctgatctcggaccaaactgcaagtaaaattgcagagaggatgagttgtacagaaca 3119

3120 agcgtgcattgttctggaagttcatctctccttgttgctcgacctttgttgctgcagtttcgccaagtccactagacaatgtt 3199

3200 acgagttaagcctctgtcaaacagatcgctcagcgtcccagaaaacaccagattttcgaaaaccatcggggatcaatt 3279

3280 ttcgattcaattccgatcttggaagtactgaacagaagcatgatgctaaagataatcaacagaccccaaaaaatgaca 3359

3360 ttgtacagaaagcaacaagtcaactcaaaaatcaaagttcaacttacatcttacagacccccaaaaaatgaca 3439

3440 gttaacagaagtcgactaacagaaacagccagcttcacctggaatgaaggagctttgatcaatcatcctagcttcat 3519

3520 tccccttttgaaattgcagacagagctctcatcctgctaaagctgttggcttattcttaaccctgcaatcaataagcatga 3599

3600 actaacattgacaccttcatcggcgattgctcgaaatcagtgagcgagggattaacctgtgtgtagtaacctctc 3679
```

FIGURE 1-4

```
3680  tccttgtacataaatctggaaattccggcatcaactactgccacctttctgcttaaggtgattttatcaccaaggctga  3759
3760  gcgtgattccttgctcttgctccgaatcctgatgtatccactgagctttccatctccttctccaggcttatgttc      3839
3840  accaatgcgtcctcgccgaacacactcttggcgcagcaagttcgcgtacaagttcaacactctccatcaagtgcagacct  3919
3920  gcaaacccaaataagaacacaaactccaaagtcaacgatcaattctccgccttttatgaagaaaggaaacttctgggt    3999
4000  acttacggtgtgccgtcagacacttcatatttgtagacttgatgatatggtccaggaattccttctcgttctgaattgttgt  4079
4080  gttaacagcaacctgacagacagaaagatatcgcaaatttaagatactggatgactaggcacagagcagcaagaatctaa  4159
4160  ttctagaagtaaaaccttattttcccattcaaattctgcccacatagtccgaacgcagcatccgagcaagaagcaggag    4239
4240  agatgtaatccatgatatcgatgtggatatcgttgaggacgacaactgaacgttccatcacattgg  4305
```

FIGURE 2-1

```
   1 tctagacattgacataaccgaattcaaagaacacaacattgactaaccaccaaaagaaatagagtagtgaaatttgga   80
                   R1
  81 agattaaaaatagaaacaaactgattcttagaaagaagagatgattaggtgcttcagttcgtgcttcagttcgtctgtcaggaaatcga  160
     R2
 161 gatgttcacttattgtcgattcatctcccaattgtcctgttccttactgtccgacgcttttttgaatcccag  240
              R3
 241 ttaattcccatcaagtcttcctcagctgctagcactgctagctcccaacatggagcgtggagtctactcgttcatgggg  320
 321 catcgcaaaggtttgccttcatgttctgctaccagccagcgcccaccgcctcttggttgtgtggacaattgcggtgaagc  400
 401 gcgcaagttgacatcccatagtctcgacacttcaccatggatgtttaaaacgtatatcacgagtgcgatctacatgtc  480
 481 ccatcacaccacacatataaagcaatagtttgggagctttcatatttgaaacgggcattgacgactgccctctcgataat  560
 561 ttaatctttttttctcttcagctgattgtgtgcatccattcgggctcagaagcacatcaaaggatctctccatcgtagt  640
 641 attgggtcgtgtcgtatgatacgaagcagtcgatgaagtttcctaatgtgcgagctacaggctccgcaaagaaccccgca  720
 721 ggtagatcgtatgctagtacccaaaatcagtttgtcgtagcggaatcaacactagagactcacccttaatgcatctcatg  800
 801 tgtgatgaacagttattcatttgtgagtctaggggtcattgtcgatgaccaatgcacattgagcttatgatagaatttg  880
 881 aataggaagcgttttccacccagatcacgaatagctaccccctttttcgggcgccaaattccggcgcatcctatcttccacc  960
 961 acaacttaaagatgcgatcggtaaggaactcaccgaccacacatcgaataatcttcggtgaccggttcctgttgatca  1040
1041 agtccctcaattcctcaacctagtcttcaatcgccgctagcgttatcccccgcatatgacttcatagcgcggagcgt  1120
1121 agccggagacgacgagcaagaaggatgagcgcggcggcagattgcggctaagaaaacgagcttcctgcctgtctatggag  1200
1201 gcagatttctgagttgatggtgatgtggacactttaattaagttgattttttagcacttcattcacg  1280
1281 taattaaataaattccagtattttatattttcctacgttatctaattttttgaaagattaaaactttgatat  1360
     R4                                                                          R2
```

FIGURE 2-2

```
1361 aggcaagatcatgacacgtcgaagttaagtgaatgagactcctaacaagtaataacaagcagttcataaccgaatga 1440
                                                                    R1
1441 cctgatctcttactaagcttgagatcattgaacatataattaatacgttaatgaagataagaactttaatataaaat 1520
1521 cattcaaaacgagaaactgataacaaacaaaacggccaacaaataatagacggtggaggatgatgcagagcc 1600
                                                                          R5
1601 atccaccctttttccagttccttactcttctatgcatatcacaagacgcccttgaacttgttagtcatg 1680
1681 cagagcccttactcgcaggtcaccgcaccacgtgttactctctatcactctcctcctttaagaaccaccacgc 1760
      R5
1761 cacctcctctcacaaacactcataaaaaccactcttgcatttctcccaagtcaattagttcacagctaagcaag 1840

1841 aactcaacaaca ATG GCG GAT CGT ACA ACA CAG CCA CAC CAA GTC CAG GTC CAC ACC CAG CAC 1903
                M   A   D   R   T   T   Q   P   H   Q   V   Q   V   H   T   Q   H    17
              1

1904 CAC TAT CCC ACC GGC GGG GCT TTC GGC CGT TAT GAA GGT GGA CTC AAA GGC GGT CCA CAT 1963
 18   H   Y   P   T   G   G   A   F   G   R   Y   E   G   G   L   K   G   G   P   H    37

1964 CAC CAG CAA GGA TCA GGC AGC GGC CCA TCA GCT TCC AAG GTG TTA GCA GTC ATG ACC GCG 2023
 38   H   Q   Q   G   S   G   S   G   P   S   A   S   K   V   L   A   V   M   T   A    57

2024 CTC CCC ATC GGC GGG ACC CTC GCC CTT GCC ATA ACC TTG GCT ACG ATG ATC 2083
 58   L   P   I   G   G   T   L   A   L   A   I   T   L   A   G   T   M   I    77

2084 GGG CTG GCG ATC ACC ACC CCG ATT TTT GTC ATC TGC AGC CCT GTT CTA GTC CCG GCC GCT 2143
 78   G   L   A   I   T   T   P   I   F   V   I   C   S   P   V   L   V   P   A   A    97

2144 CTC CTC ATC GGG TTT GCC GTG AGC GCG TTT CTG GCC TCG GGG ATG GCC GGG CTG ACA GGG 2203
 98   L   L   I   G   F   A   V   S   A   F   L   A   S   G   M   A   G   L   T   G   117

2204 CTG ACC TCG CTG CTG TCG TGG TTT GCG AGG TAT CTG CAG CAG GCT CAG GGA GTT GGA GTG 2263
118   L   T   S   L   L   S   W   F   A   R   Y   L   Q   Q   A   Q   G   V   G   V   137

2264 GGG GTG CCG GAT AGT TTC GAG CAG AAG CGC CGC ATG CAG GAT GCT GCT GGG TAT ATG 2323
138   G   V   P   D   S   F   E   Q   A   K   R   R   M   Q   D   A   A   G   Y   M   157
```

FIGURE 2-3

```
2324 GGG CAG AAG ACC AAG GAA GTT GGG CAG GAG ATC CAG AGG AAG TCT CAG GAT GTG AAA GCA   2383
 158  G   Q   K   T   K   E   V   G   Q   E   I   Q   R   K   S   Q   D   V   K   A    177

2384 TCA GAC AAA TAA ggtgataataaggggtttgggttcgtgtgtaaactggtaaatgaaattctggtttactg         2459
 178  S   D   K   *                                                                      181

2460 tacttttgcatgtgtagtggaatgaatgagttctttgttctctttttaatcataaagtaagaagcagcatttcatgt        2539
2540 tctggttgaatattgtcaagaattcgcaacaaatttagctaaccagttcaatcttaccgttagacgacttcccagtaa      2619
2620 gaaacattccaggtccatcccgtataagagtctggacttctgaaacctttagacccttggatttggaaaaagatgaaac    2699
2700 ctttagaataaattacaacgatggcagattgtacaaaactggagtcgagatcatgtaaattagcccataactaagaaccg   2779
2780 gcgatgacaacaattactaggaatatggttgttggctgtcggcgggctagcgtgatgatttggaagaatcggggatcc      2859
2860 agaatgtgagaaccgatcatcgacgaacattacccggcgaacattcaagcaactttggaactcctatatggct          2939
2940 gttccagcaggccacctgctcaagaagaagccatgtcagaaatcctacgaaatctaactgatgctgatatgaa           3019
3020 tccgccaggtgtgcggagttctttacaggcaggatcctaacaacaaatacgattctgtaagaacaagcgcagaaacttctgcaac 3099
3100 agcacgcagcgatctatctccgatatttggttctgagttggagaaagatgaccatactgtatttggttgaacttggaaccga  3179
3180 gaaaccactcgtatatttggttctgagttggagaaagatgaccatactgtatttggttgaacttggattggaaccga        3259
3260 aattttgagttgaaaagcgagtgatcgtatataaatttcagattcagattaggatatcctatgagagaaggtagagttac     3339
3340 ctgatactacatactgccatcaggggtaaaagttgcctcgatggttgtgtttggagatggttccaggctaaatccacaa      3419
3420 cgctgaacaaattaaagatgaatggatcaatcttcaacccttacttctgcatttatgaggattggctcaaggctctcta     3499
3500 ga                                                                                   3501
```

FIGURE 3-1

```
1    tccactatgtgtaggtcatatccatcatttaattttttgggcaccattcaattccatcttgccttttaggatgtgaatatga      80
          5' primer (1)          AT rich
81   acggccaagtgtaagagagaataaaaataatccaaattaaagcaagaggccaagtaagataatccaaatgtacacttgtca    160
                                                AT rich
161  tcgccgaaattagtaaaatacggcatatgtattcccacacattataaaatacgtatatgtattggctgcatttgc          240
241  atgaataatactacgtgtaagcccaaaagaacccacgtgtagcccatgcaaagttaacactcacgacccattcctcagt      320
      RY                                    G box seed-specific
321  ctccctatataaacccaccatcccaatcttaccacaccacgactcacaactgactctcacacttaaagaa                400
             TATA                                              3' primer (1)
401  ccaatcaccaccaccaaaaaATGGCAAAGCTGATGAGCTTAAGACTCTGGAGCAGTTCCTCTTCCTGATCGTGGTGGAC       480
                        M  A  K  L  M  S  L  A  A  V  A  T  Q  F  L  F  L  I  V  V  D      21
481  GCATCCGTCCGAACCACAGTGATTATCGACGAGGAGACCAACCAAGGCCGCGGTGTGGAGGCAAGGTGGCAGGACAGCAGC     560
      A  S  V  R  T  T  V  I  I  D  E  E  T  N  Q  G  R  G  G  G  K  V  A  G  T  A  A      48
561  AGTCTGGAGCAGCAGATCCAGCAGCAGCGAGACTTCCTGAGAAGCTGCCAGCAGTTCATGTGGGAGAAAGTCCAGAGGGGCG    640
      S  L  E  Q  Q  I  Q  Q  Q  R  D  F  L  R  S  C  Q  Q  F  M  W  E  K  V  Q  R  G  G    75
641  GCCACAGCCACTATTACAACCAGGGCCGTGGAGGCGAACAGAGCCAGTACTTCGAACAGCTGTTTGTGACGACCTTA         720
      H  S  H  Y  Y  N  Q  G  R  G  G  E  Q  S  Q  Y  F  E  Q  L  F  V  T  T  L          101
721  AGCAATTGCGCACCGCGGTGCCACCATGCCAGGGGACTTGAAGCGTGCCATCGGCCAAATGAGGCAGGAAATCCAGCAGCA    800
      S  N  C  A  P  R  C  T  M  P  G  D  L  K  R  A  I  G  Q  M  R  Q  E  I  Q  Q  Q    128
801  GGGACAGCAGCAGGACAGCAGGAAGTTCAGAGGTGGATCCAGCAGGCTAAACAAATCGCTAAGGACCTCCCCGGAC        880
      G  Q  Q  Q  Q  Q  Q  E  V  Q  R  W  I  Q  Q  A  K  Q  I  A  K  D  L  P  G  Q    155
```

FIGURE 3-2

```
 881 AGTGCCGCACCCAGCCTAGCCTAGGCCAGTTCCAGGGCCAGCAATCTGCATGGTTTGAagggtgatcgattga  960
 156  C  R  T  Q  P  S  Q  C  Q  F  Q  G  Q  Q  Q  S  A  W  F  *    5'primer (2)   175
 961 gatcgtacaaagacactgctaggtgttaaggatgatgataataatgagatgaatgtgtttaagttagtgtaa 1040
1041 cagctgtaataagagagagagagagagagagagagaggctgatgaaatgttat 1120
1121 gtatgtttcttggttttaaaataaatgaaagcacactactacaaccaagccgtggaggagggcaacagagccagcacttcgatagctg 1200
1201 aaagtccagaagggcggcgccagctactactacaaccaagccgtggaggagggcaacagagccagcacttcgatagctg 1280
1281 ctgcgatgatcttaagcaattgaggagcgagtgcacatgcaggggactggagcgtgcaatcggccagatgaggcaggaca 1360
1361 tccagcagggacagcagcaggaagttgagaggtggtcccatcaatctaaacaagtcgctaggaccttccggacag 1440
1441 tgcggcacccagcctagccagtccagggcagcagtctgcatgtttgaagtggtgatcgtgatgagatcg 1520
1521 tataaagacactgctaggtgttaaggatgggataataagatgtgtttaagtcattaaccgtaataaagagagagagg 1600
1601 ctgatggaatgttatgtatgtttcctggttttaaaattaaatgaaagcacatgctcgtgtgggtttctatc 1676
                                                             3'primer (2)
```

FIGURE 4-1

```
         10         20         30         40         50         60         70         80         90        100
ctcaagcatacggacaagggtaaataacatagtcaccagaacataataaacaaaagtgcagaagcaagataaaaaattagctatgacattcaggttc 110        120        130        140        150        160        170        180        190        200
atattgaaacatcattatcctagtcttgtgaccatccttcctcctgctctagttgagaggcttgggactaacgagaggtcagttggatagcagatcc 210        220        230        240        250        260        270        280        290        300
ttatcctggactagcctttctgtgtttcagatcttcgtgccgcgtctacatctatctccattagtctgaagatgactcttcaccaacgacgttt
                                                                            IR1

310        320        330        340        350        360        370        380        390        400
aaggtctctatcctcctactcctagcttgcaatacctggcttgcacgatgattggacatcgtgcacgatgattggatactgtggaggagtgtttgctgatt
                                                                IR1

410        420        430        440        450        460        470        480        490        500
tagagctcccggttgggtgatttgacttcagtttaggcttgttgaaattttcagttccattgtgaagcttagagcttgagcttccttcca 510        520        530        540        550        560        570        580        590        600
tgttaatgccttgatcgaattctcctagagaaaaggaagtcgatctctgagtattgaaatcgaagtgcacattttttttcaacgtgtccaatcaatcca
              IR2

610        620        630        640        650        660        670        680        690        700
caaacaagcagaagacaggtaatctctttcatactttatgacaagtaatagtctcttaccgtcatgcataataacgtctcgttcctcaagagggttttc 710        720        730        740        750        760        770        780        790        800
cgacatccataacgaccgaagcctcatgaagcattagggaagaacttttggttcttcttgtcatggcctttataggtgtcagccgagccgagctcgccaattc 810        820        830        840        850        860        870        880        890        900
ccgtccgactggctccgcaaaatattcgaacgcaagttatgacttgcaaccataactccacggtattgagcaggaccattgtgaagactcatctcat 910        920        930        940        950        960        970        980        990       1000
ggagcttcagaatggttgtcagcaaccaatgaccgaatccatcacatgacgacgtcgagtgggtgagcgagcgaaacgaaacaggaagcgcctatctttt 1010       1020       1030       1040       1050       1060       1070       1080       1090       1100
cagagtcgtgagctccacaccgattccggcaactacgtgttgggcaggcttccgcgtattagagatatgttgaggcaagaaccatctgtgccactcgta 1110       1120       1130       1140       1150       1160       1170       1180       1190       1200
caattacgagagttgttttttttgtgattttcctaagtttctcgttgatggtgagctcatattctacatcgtatggtctctcaacgtctcgttcctgtcat
```

FIGURE 4-2

```
     1210       1220       1230       1240       1250       1260       1270       1280       1290       1300
ctgatatcccgtcatttgcatgcgccgcctccacgtgccaagtcccctagtgtcatgcacgccaaattggtggtgcgcgctgccctgtctt
                              ABRE
     1310       1320       1330       1340       1350       1360       1370       1380       1390       1400
cttaccgatggtgagttgagtttgggggtctccgcggcgatggtagtggttgacggtttgttgtggttgacgcattgatcaattactctttgc
                                                                              R1
     1410       1420       1430       1440       1450       1460       1470       1480       1490       1500
ttcaaattctttggcagaaacaattcattagattagaactggaaccagagtgatgagacggattaagtcagattccaacagagttacatctcttaaga
                                                                                                R1
     1510       1520       1530       1540       1550       1560       1570       1580       1590       1600
aataatgtaacccctttagacttatatatttgcaattaaaaaataatttaactttttagactttatatagtttaataactaagtttaaccactcta
              R2
     1610       1620       1630       1640       1650       1660       1670       1680       1690       1700
ttatttatcgaaactatttgtatgtctcccctctaataaacttgtattgtgtttacagaacctataatcaaataatcaatactcaactgaagtttg
                                                                                      R2
     1710       1720       1730       1740       1750       1760       1770       1780       1790       1800
tgcagttaattgaaggattaacgccaaaatgcactagtattatcaaccgaatagattcacactagatggccatttccatcaatatcatcgccgttctt
     1810       1820       1830       1840       1850       1860       1870       1880       1890       1900
ctttctgtccacatatcccctctgaaacttgagagacacctgcacttcattgtcttattacgtgttacaaaatgaaaccatgcatcgatgcaaactgaa
                                                                              Legumin  Vicilin
     1910       1920       1930       1940       1950       1960       1970       1980       1990       2000
gaatgcgcaagaaccctttccccctccattttcttatgtggcgaccatccattcaccatcccgctataaacaccccccatcacttcacctagaacatca
                                                                CAAT       TATA
     2010       2020       2030       2040       2050       2060       2070       2080       2090       2100
tcactacttgcttatctcatccaaaagataccccaccATGGCTAGATCATCAAGCCCTTGCTTCTCTGCTTGCTCCACTCTGCATTTCGCACTCTTCCACTCTTC
                                       M  A  R  S  S  P  L  L  L  S  L  L  C  I  F  A  I  L  F  H  S
                                                       Signal sequence
     2110       2120       2130       2140       2150       2160       2170       2180       2190       2200
TCTGGGTAGGCAGCAATTCCAGCAGGGGAACGAGTGCCAGATGCCGACATCCGAGCCGACAAAACCATCCAGCGACAGAAGCTGGCACCATC
 L  G  R  Q  Q  F  Q  Q  G  N  E  C  Q  I  D  R  I  D  A  S  E  P  D  K  T  I  Q  A  E  A  G  T  I
     2210       2220       2230       2240       2250       2260       2270       2280       2290       2300
GAGGTATGGGACCAGAACCGCCAGCAATTCCAGTGCGCTGGTGTTGCCGTTGTAAGGCGACCATTGAGCCCAAAGGTCTTCTCTTGCCTTTCTACAGCA
 E  V  W  D  Q  N  R  Q  Q  F  Q  C  A  G  V  A  V  V  R  R  T  I  E  P  K  G  L  L  L  P  F  Y  S
```

FIGURE 4-3

```
     2310      2320      2330      2340      2350      2360      2370      2380      2390      2400
ACACCCCTCAGCTCATCTACATCGTTCAAGgtataaattaatcagttcatcaatgataaccaccacttcgaatgtatttatcaaatatcaatgatcga
 N  T  P  Q  L  I  Y  I  V  Q 2410      2420      2430      2440      2450      2460      2470      2480      2490      2500
tgcacctgtatgtgtgtatattcagGTAGGGGAGTTACAGGAGTCCAGAGAACATTCGAGGAATCCAGCAGCAAGGACAAC
                         G  R  G  V  T  G  I  M  F  P  X  C  P  E  T  F  F  E  E  S  Q  Q  Q  G  Q 2510      2520      2530      2540      2550      2560      2570      2580      2590      2600
AGGGCCAACAGGGTAGTTCCCAAGACCACCAGAAGATCCGCCGCTTCCGTGAAGGTGACGTCATTGCCGTCCCTGCCGGTGTAGCCCACTGGTCCTA
 Q  G  Q  Q  G  S  S  Q  D  Q  H  Q  K  I  R  R  F  R  E  G  D  V  I  A  V  P  A  G  V  A  H  W  S  Y 2610      2620      2630      2640      2650      2660      2670      2680      2690      2700
CAACGATGGCAACGAACCAGTCATGGCCATTGTTGTCCATGACACTTCCAGCCACCTCAACCAACTGGACAACAACCCCAGgtatataagcattgccgt
 N  D  G  N  E  P  V  M  A  I  V  V  H  D  T  S  S  H  L  N  Q  L  D  N  N  P  R 2710      2720      2730      2740      2750      2760      2770      2780      2790      2800
agttgctaataaattgcacacaattggaactctattttcagtatctaataacttttcctttttggcagAACTTCTACTTGGCAGGAAACCCGAGAGAC
                                                                    N  F  Y  L  A  G  N  P  R  D 2810      2820      2830      2840      2850      2860      2870      2880      2890      2900
GAGTTCGAACAATCGCAGCAGGAGCAGGCTGAGCCGTGGGGAGAGTGAAGGTGGACGGAGGAACGCAGGAGAACCTCTTCAACCTGCAACAACCTCTTCTT
 E  F  E  Q  S  Q  Q  E  Q  G  G  R  L  S  R  G  E  S  E  G  G  R  G  R  R  E  P  L  Q  P  A  T  T  S  S 2910      2920      2930      2940      2950      2960      2970      2980      2990      3000
GCGGAATCGACTCCAAGCTCATCGCGGAGGCGTTCAATGTCGACGAGGCAGTGGACGAGGAGGTACAGAGGCGAGAACAACAGAGGCCAGATCGTCCG
 A  E  S  T  P  S  S  S  R  R  S  R  R  V  Q  C  V  D  E  A  V  D  E  E  V  Q  R  R  E  Q  Q  R  P  D  R  P 3010      3020      3030      3040      3050      3060      3070      3080      3090      3100
AGTCGAAGGCGAGCTCGACATCGTCAGACTTCCGACCAGTATCCAGGAGGAGTCACAGGAGGAGGTCGTGGTGGCCGTACTACTCCAATGA
 V  E  G  E  L  D  I  V  R  P  P  T  S  I  Q  E  E  S  Q  E  Q  G  G  R  G  G  G  R  Y  Y  S  N  G 3110      3120      3130      3140      3150      3160      3170      3180      3190      3200
GTGGAGGAGACCTTCTGCTCCATGAGACTAATTGAGAACATCGGCGATCCTTCTCGGGCAGAGCATTTCACTCCAGAAGCCGGTTAGATCCCTCA
 V  E  E  T  F  C  S  M  R  L  I  E  N  I  G  D  P  S  R  A  D  I  F  T  P  E  A  G  R  V  R  S  L
```

FIGURE 4-4

```
          3210       3220       3230       3240       3250       3260       3270       3280       3290       3300
ACAGCCACAACCTCCCGTCCTGCAATGGATCCAGTTAGCGCCGAGAGAGGCGTTCTCTACAATgtatagatctcactcacgcaccaactctaaattga
 N  S  H  N  L  P  V  L  Q  W  I  Q  L  S  A  E  R  G  V  L  Y  N
          3310       3320       3330       3340       3350       3360       3370       3380       3390       3400
atccctaattattcaccgatatctgaccgacccggtttgaattttgtagGAAGCGATCAGGCTGCCGCACTGGAACATCAACGCACACAGCATAGT
                                                  E  A  I  R  L  P  H  W  N  I  N  A  H  S  I  V
          3410       3420       3430       3440       3450       3460       3470       3480       3490       3500
GTACGCGGATCAGAGGACAAGCCAGATCGTGCAGATCCGGAATTCGGTGTTCGATGGAGTGCTGCAGGAAGGACAGGTGGTGACGGTGCCG
 Y  A  I  R  G  Q  A  R  V  Q  I  V  N  E  E  G  N  S  V  F  D  G  V  L  Q  E  G  Q  V  V  T  V  P
          3510       3520       3530       3540       3550       3560       3570       3580       3590       3600
CAGAACTTCGCGGTGGTAAAGAGATCCCAGAGCCAGAGAGGTTTGAGTGGGTGGCGTTCAAGACCAACGACAATGCGATGGTGAACTCGCTAGCCGGGAGGA
 Q  N  F  A  V  V  K  R  S  Q  S  E  R  F  E  W  V  A  F  K  T  N  D  N  A  M  V  N  S  L  A  G  R
          3610       3620       3630       3640       3650       3660       3670       3680       3690       3700
CATCGGCAGTAAGGGCGATCCCCGCGATGTACTGGCTAACGCCTGAGGGTGTCGCCGGAGGAGGCGAGGAGGGTGAAGTTCAACAGGCAGGAGACTCA
 T  S  A  V  R  A  I  P  A  D  V  L  A  N  A  W  R  V  S  P  E  E  A  R  R  V  K  F  N  R  Q  E  T  H
          3710       3720       3730       3740       3750       3760       3770       3780       3790       3800
CTTGGCTAGCACCAGGGCGCCAGTCGCCCGGAGGTCGAATGTCGTCAAGGAGGTGATCAACTTGCTTATGTAAaatgtgacggtgaaataataa
 L  A  S  T  R  G  Q  S  R  S  P  G  R  L  N  V  V  K  E  V  I  N  L  L  M  *
          3810       3820       3830       3840       3850       3860       3870       3880       3890       3900
cggtaaaatatgtaataataaagccacacaaagtgagaatgagggggaaggggaaatgtgtaatgagccagtagccggtggtgctaattttg
          3910       3920       3930       3940       3950       3960       3970       3980       3990       4000
tatcgtattgtcaataaatcatgaattttgtgttttttatgtgttttttaaatcatgaatttaataaatctccaatcggaagaacaac
          4010       4020       4030       4040       4050       4060       4070       4080       4090       4100
attccatatccatgtgatgtttctttacccaaatctagtcttgagaggatgaagcatcgacagttctgcaactatccctcaaaagctttaaaatga
          4110       4120       4130       4140       4150       4160       4170       4180       4190       4200
acaacaaggaacagagcaacgttccaaagatcccaaacatattatctatactactaatactactattattattaattactactgcccgaatcacaatccct
```

FIGURE 4-5

```
      4210       4220       4230       4240       4250       4260       4270       4280       4290       4300
gaatgattcctattaactacaagcctt gttgcggcggagaagtgatcggcgcggcgcgagaagcagcgagacctcggagacgaggcctt ggatgagcagagtc 4310       4320       4330       4340       4350       4360       4370       4380       4390       4400
tttacctgccagggcgtgaagggaagagcggcctt ctctggagtaggagttcagcaagcggcggttcctt ggcggagtaagcggacgtaagggtggntgtc 4410       4420       4430       4440       4450       4460       4470       4480       4490       4500
gacgtcntcgtttcggaggcgnattcatgaaggtt aaagtcanatctgtagctctcgagtgctcaggagccnaaagacgtt gggaaaccgtcgncgt 4510       4520       4530       4540       4550       4560       4570       4580       4590       4600
ttgggcatcagtcngcggggcacgcttccctcctgctgctccanaancnangtanatttaaaagana tggaaattaantaatggaatnannaggagg 4610       4620       4630       4640       4650       4660       4670       4680       4690       4700
attgnaacggtcngancggtttttanggttt aaatactgggggagtngagccngccnctggttccngtgtagangaaccaagnnccgg 4710       4720       4730       4740       4750       4760       4770       4780       4790       4800
gaggnttncannngnnaggggagaaaaaggannca tttnannangcngagggacatgaancgtacngagctgnggttcannnancggcgnnnggnagtcc 4810       4820       4830       4840       4850       4860       4870       4880       4890       4900
cnnggaccnggntgggtnanaagggaanggaaca ttnggtngnanggananaccntttacnatgcctttgcaggnnngtntnggcncntncgggt 4910       4920       4930       4940       4950       4960       4970       4980       4990
nacatnccgctgcatgggngctttggggngccnanaggnagcccnca nggnannccngccncctt gtncangncgctnaagttcnattgtanatggncgttg
```

A            B 10J
(L-isoform)

3T
(H-isoform)

Figure 9.1
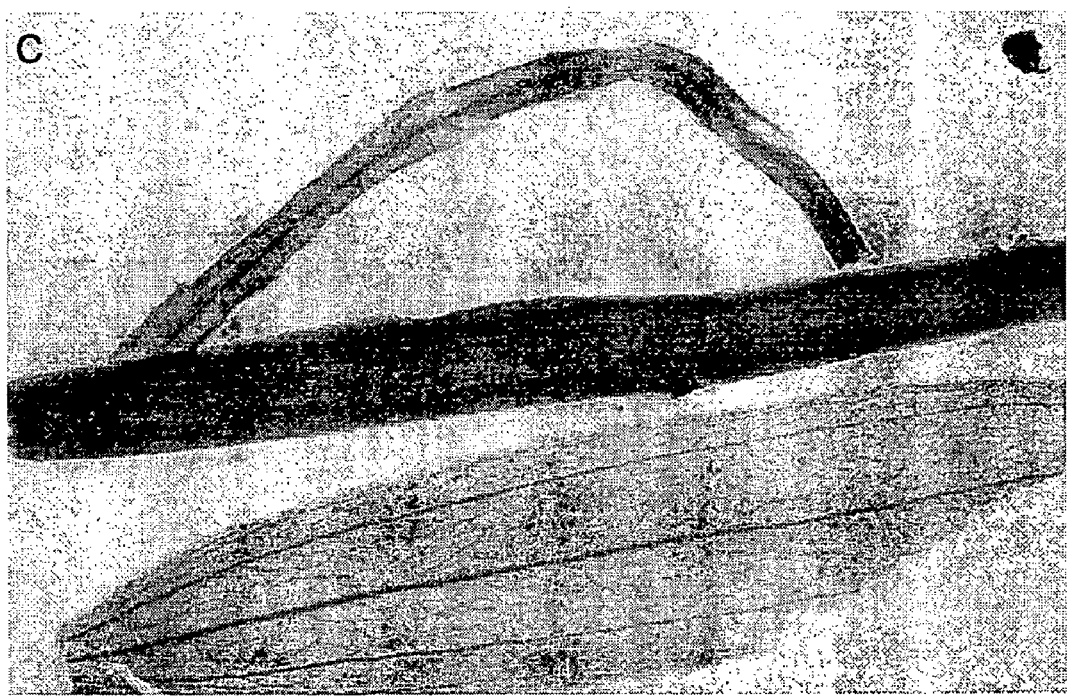

Figure 9.2
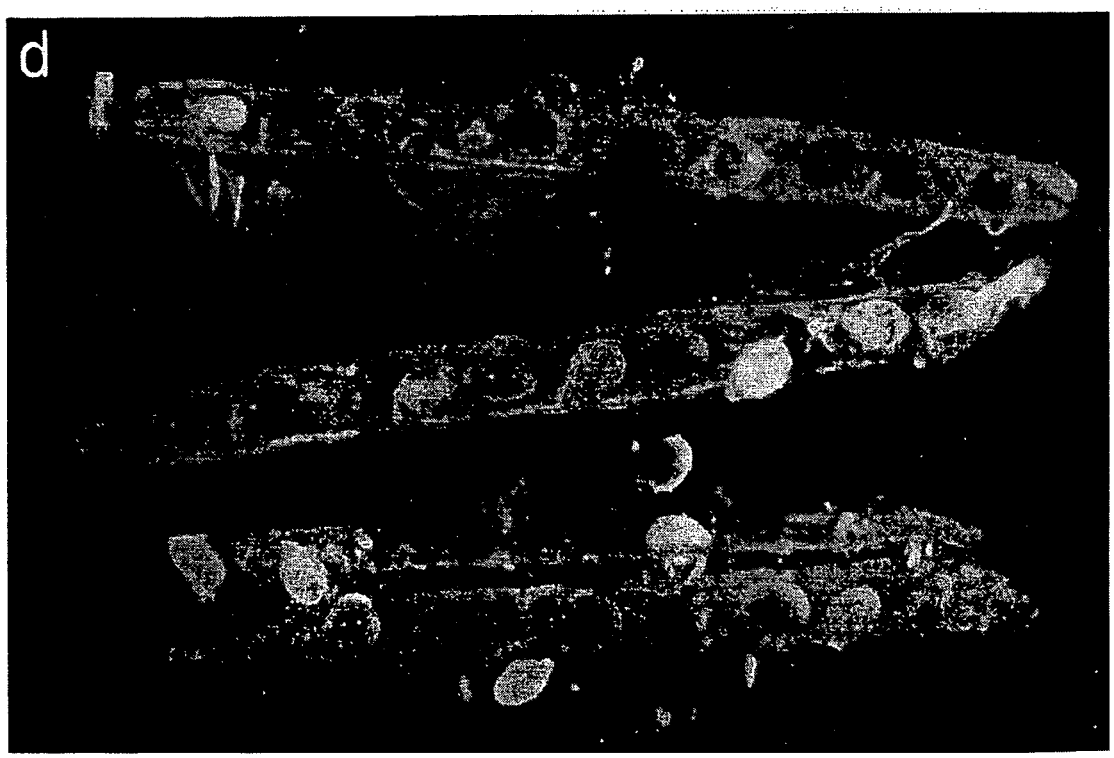

FLAX SEED SPECIFIC PROMOTERS

CROSS-REFERENCE TO RELATED PATENT APPLICATIONS

This application is a continuation-in-part of U.S. application Ser. No. 09/645,593 filed Aug. 25, 2000 (now U.S. Pat. No. 6,777,591), and claims benefit from U.S. Provisional Application Nos. 60/151,044, filed Aug. 27, 1999 and 60/161,722, filed on Oct. 27, 1999.

FIELD OF THE INVENTION

The present invention relates to plant genetic engineering methods useful for the alteration of the constituents of plant seeds.

More specifically, the invention relates to promoters that have been obtained from flax and are capable of directing expression of non-native genes in flax seeds as well as the seeds of other plants.

BACKGROUND OF THE INVENTION

Flax or linseed (*Linum usitatissimum*) is a commercially important oilseed crop. Flax oil and meal are valuable raw materials derived from flax seed. A further economically significant raw material, flax fiber, is obtainable from the stem of the plant. The flax oil fraction is used for non-edible purposes, for example in the manufacture of varnish and paint, and has more recently become suited for use in the manufacture of a range of edible products, such as margarines and salad oils and dressings, by virtue of newly bred so called Linola cultivars (Green (1986) Can. J. Plant Sd, 66: 499-503). Flax meal is used primarily as a constituent of ruminant feeds while flax fibers are used in the manufacture of linen fabrics. Given its economic importance as a source for raw materials, it is desirable to further improve and diversify the available flax cultivar portfolio both with respect to agronomic performance, for example seed yield, resistance to pathogens and low climatic temperatures, and with respect to yield and quality of the raw materials to suit downstream applications.

Although it is possible to obtain improved flax cultivars through conventional plant breeding, as evidenced by the development of the Linola cultivars, developing an elite agronomic plant line requires large investments in plant breeding due to the long timelines involved.

Plant genetic engineering technology allows the isolation of genes directly from unrelated species and the transfer of these genes into elite agronomic backgrounds, thereby significantly reducing the time required to develop new cultivars. In addition plant genetic engineering permits the manufacture of products not naturally obtainable from flax, for example therapeutic agents.

In order to develop novel flax cultivars through plant genetic engineering, control over the expression of the introduced foreign or non-native gene is of critical importance. The desired expression characteristics for the non-native gene, such as the level of expression of the non-native gene, the particular plant tissue or organ in which the non-native gene is expressed, and the particular time in the growth cycle of the plant at which the non-native gene is expressed, will vary depending on the application for which the plant line is developed. For example, the modification of the seed oil composition may require low levels of seed-specific expression of an enzyme involved in fatty acid metabolism at an early stage in seed development (see for example U.S. Pat. No. 5,420,034). On the other hand expression of a pharmaceutical protein could preferably require high levels of leaf-specific expression upon harvesting of the plant leaves (see for example, U.S. Pat. No. 5,929,304).

In order to manipulate the expression characteristics of non-native genes numerous factors can be influenced. One factor is the choice of the transcriptional promoter used. A wide range of plant compatible promoters is currently available and some of the better documented promoters include constitutive promoters such as the 35-S CaMV promoter (Rothstein et al. (1987), Gene 53: 153-161) and the ubiquitin promoter (U.S. Pat. No. 5,614,399), tissue specific promoters such as seed-specific promoters, for example the phaseolin promoter (Sengupta-Gopalan et al., (1985), PNAS USA 82: 3320-3324) and inducible promoters, such as those inducible by heat (Czarnencka et al., (1989), Mol. Cell. Biol. 9 (8): 3457-3464), UV light, elicitors and wounding (Lois et al., (1989) EMBO J. 8 (6): 1641-1648), or chemicals such as endogenous hormones (Skriver et al. (1991), Proc. Natl. Acad. Sci. USA 88(16): 7266-7270). Other factors that can be manipulated in order to control the expression characteristics of non-native gene in plants include transcriptional modification factors such as introns, polyadenylation sites and transcription termination sites. The expression characteristics of the non-native gene can further be manipulated by factors that affect translation, such as ribosomal binding sites and the codon bias that is exhibited by the host.

Furthermore, the non-native gene itself may affect the viability of the transgenic plant, thus limiting particularly the levels of expression that can be attained. In some cases it may be possible to overcome this problem, by expressing the protein in a tissue specific manner, e.g. in the leaves or seed, or by restricting the accumulation of the protein in different subcellular compartments such as for example the cytoplasm, the endoplasmic reticulum or vacuoles, typically by the presence or the absence of specific targeting sequences capable of directing the protein to these compartments. Another factor that will affect the expression characteristics is the location in which the construct inserts itself into the host chromosome. This effect could provide an explanation as to why different plants, transformed with the same recombinant construct, can have fluctuating levels of recombinant protein expression.

To the best of the inventors' knowledge, expression of non-native genes in flax seeds is only documented in PCT Patent Application WO 98/18948. This application discloses two stearoyl-acyl carrier protein desaturase (SAD) genes derived from flax. The associated SAD promoter sequences are useful for the modification of flax and other plants for the expression of endogenous or foreign genes. However the methods taught by WO 98/18948 are limited by the fact that the SAD promoters are not seed-specific in flax and confer expression to leaves, stems, flowers and seeds. Expression of non-native genes thus may result in undesirable side effects in non-seed tissues. In addition the use of the SAD promoters allows limited control over expression level and timing of expression.

There is a need in the art to further improve methods for the expression of non-native genes in flax seeds and other plant seeds.

SUMMARY OF THE INVENTION

The present invention relates to improved methods for the seed-specific expression of non-native genes in plants. In particular, the invention relates to improved methods for the seed-specific expression of non-native genes in flax.

Accordingly, in one aspect, the invention provides a method for the expression of a nucleic add sequence of interest in plant seeds comprising:
   (a) preparing a chimeric nucleic add construct comprising in the 5' to 3' direction of transcription as operably linked components
      (1) a seed-specific promoter obtained from flax; and
      (2) the nucleic add sequence of interest wherein said nucleic add of interest is non-native to said flax seed-specific promoter;
   (b) introducing said chimeric nucleic add construct into a plant cell; and
   (c) growing said flax plant cell into a mature plant capable of setting seed, wherein said nucleic acid sequence of interest is expressed in the seed under the control of said flax seed-specific promoter.

In a preferred embodiment the seed-specific promoter obtained from flax comprises at least one of the following promoter elements: an RY-repeat, an ABRE, an E-BOX or an SEF3 element. Preferably the seed specific promoter obtained from flax comprises and RY-repeat and an ABRE.

In a further preferred embodiment of the invention, at least one expression characteristic, e.g. timing of expression in the plant's life cycle, conferred by the promoter to the non-native nucleic add sequence is similar to that expression characteristic when conferred to a native nucleic acid sequence. In further preferred embodiments, the flax seed-specific promoter is an oleosin promoter, a 2S storage protein promoter or a legumin-like seed storage protein promoter.

In a further aspect, the present invention provides transgenic seeds prepared according to a method comprising:
   (a) preparing a chimeric nucleic acid construct comprising in the 5' to 3' direction of transcription as operably linked components:
      (1) a seed-specific promoter obtained from flax; and
      (2) a nucleic acid sequence of interest wherein said nucleic acid of interest is non-native to said seed-specific promoter;
   (b) introducing said chimeric nucleic acid construct into a plant cell; and
   (c) growing said plant cell into a mature plant capable of setting seed, wherein said nucleic acid sequence of interest is expressed in the seed under the control of said seed-specific promoter.

In a further aspect the present invention provides plants capable of setting seed prepared by a method comprising:
   (a) preparing a chimeric nucleic acid construct comprising in the 5' to 3' direction of transcription as operably linked components:
      (1) a seed-specific promoter obtained from flax; and
      (2) a nucleic acid sequence of interest wherein said nucleic acid of interest is non-native to said seed-specific promoter;
   (b) introducing said chimeric nucleic acid construct into a plant cell; and
   (c) growing said plant cell into a mature plant capable of setting seed, wherein said nucleic acid sequence of interest is expressed in the seed under the control of said seed-specific promoter.

In yet a further aspect, the present invention provides novel flax seed specific promoters useful for the expression of non-native genes in flax seeds and the seeds of other plant species, useful for example for modification of the protein or oil composition of the seed. In a preferred embodiment the seed-specific promoter obtained from flax comprises at least one of the following promoter elements: an RY-repeat, an ABRE, an E-BOX or an SEF3 element. Preferably the seed specific promoter obtained from flax comprises and RY-repeat and an ABRE.

In a specific embodiment, the seed specific promoter comprises:
   (a) a nucleic acid sequence as shown in FIG. 1 (SEQ.ID.NO.:1), FIG. 2 (SEQ.ID.NO.:4), FIG. 3 (SEQ.ID.NO.:6) or FIG. 4 (SEQ.ID.NO.:8) wherein T can also be U;
   (b) a nucleic add sequence that is complimentary to a nucleic acid sequence of (a);
   (c) a nucleic acid sequence that has substantial sequence homology to a nucleic acid sequence of (a) or (b);
   (d) a nucleic acid sequence that is an analog of a nucleic acid sequence of (a), (b) or (c); or
   (e) a nucleic add sequence that hybridizes to a nucleic acid sequence of (a), (b), (c) or (d) under stringent hybridization conditions.

In another aspect, the invention provides chimeric nucleic add sequences comprising a first nucleic acid sequence obtained from flax operatively linked to a second nucleic acid sequence non-native to said first nucleic acid sequence wherein said first nucleic acid sequence comprises a novel flax seed-specific promoter.

Other features and advantages of the present invention will become readily apparent from the following detailed description. It should be understood, however, that the detailed description and the specific examples while indicating preferred embodiments of the invention are given by way of illustration only, since various changes and modifications within the spirit and scope of the invention will become apparent to those skilled in the art of this detailed description.

BRIEF DESCRIPTION OF THE DRAWINGS

The invention will now be described in relation to the drawings in which:

FIG. 1 shows the DNA sequence (SEQ.ID.NO.:1) of a flax genomic clone encoding a 16.0 kDa oleosin protein (SEQ.ID.NOS.:2 and 3).

FIG. 2 shows the DNA sequence (SEQ.ID.NO.:4) of a flax genomic clone encoding a 18.6 kDa oleosin protein (SEQ.ID.NO.:5).

FIG. 3 shows the DNA sequence (SEQ.ID.NO.:6) of a flax genomic clone encoding a 2S storage protein (SEQ.ID.NO.:7).

FIG. 4 shows the DNA sequence (SEQ.ID.NO.:8) of a flax genomic clone encoding a 54.5 kDa legumin-like storage protein (SEQ.ID.NOS.:9-12).

FIG. 9 shows GUS expression in developing flax embryos and *Arabidopsis* seeds of plants transformed with a 2S protein gene promoter GUS fusion.

DETAILED DESCRIPTION OF THE INVENTION

I. Seed-Specific Promoters

Figure 5:
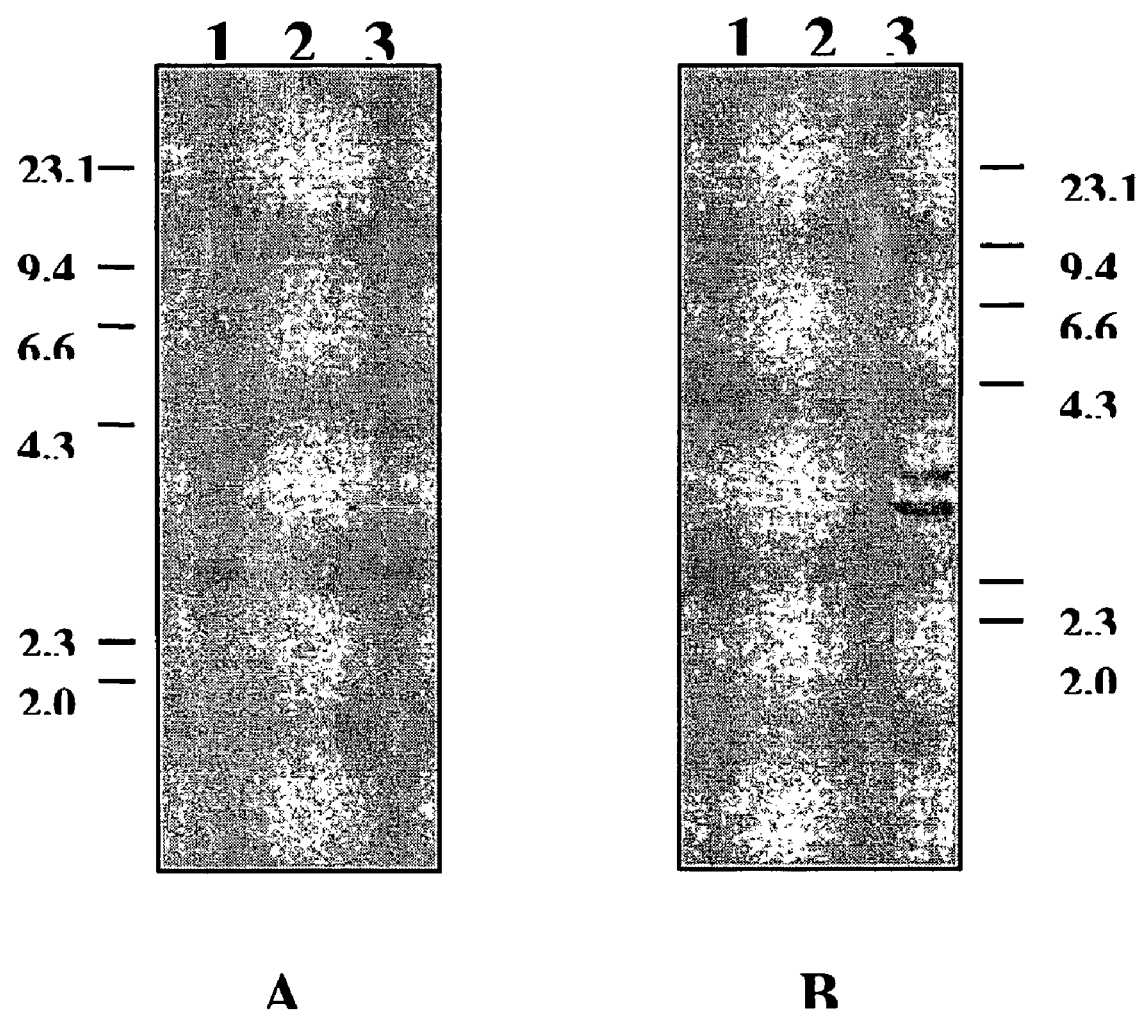
FIG. 5 shows Southern blot analysis of flax genomic DNA probed with flax oleosin DNA sequences.

The present invention provides novel flax seed specific promoters useful for the expression of non-native genes in flax seeds and the seeds of other plant species. The promoters may be used to modify for example the protein, oil or polysaccharide composition of the seeds.

The term "seed-specific promoter", means that a gene expressed under the control of the promoter is predominantly expressed in plant seeds with no or no substantial expression, typically less than 5% of the overall expression level, in other plant tissues.

In one aspect, the invention provides a flax seed specific promoter which comprises one or more of the following promoter elements purine-pyrimidine sequences (RY repeats), abscisic acid-responsive elements (ABRE), E-Box elements (CANNTG element) and soybean embryo factor 3 elements (SEF3).

As used herein, the RY promoter element is defined as a promoter element having a sequence of CATGCA in accordance with the consensus sequence for RY promoter elements as discussed by Dickenson et al. (1988) Nud. Acids Res. 16:371. The RY elements are found in seed-specific promoters of both monocots and dicots including the *napin* genes of *Brassica napus* (Ellerstrom et al. (1996) Plant Mol. Biol. 32:1019), and the maize C1 gene (Kao et al. (1996) Plant Cell 8:1171). It should be noted that RY elements have also been referred to as the "legumin box", the "Sph" element or the "G-box".

The phytohormone abscisic add (ABA) is necessary for regulation of several events during late seed development (Busk and Pages. (1998) Plant Mol. Biol. 37:425-435.) As used herein, the abscisic add responsive element (ABRE) is defined as a promoter element having a sequence of 8-10 base pairs with a core sequence of ACGT in accordance with the consensus sequence for ABRE as defined by Izawa et al. (1993) J. Mol. Biol. 14:61-72 and Shen and Ho (1995) Plant Cell 7:295-307. Hobo et al. (1999) PNAS 96:15348-15353 have performed promoter dissection studies and further identified the ABRE sequence to be (G/C/T)ACGT(G/T)GC. Expression studies have also shown that the sequence (C/T) ACGTGGC is a strong ABRE (Busk et al. (1999) Plant Mol Biol 41:529-536 and Shen and Ho (1995) Plant Cell 7:295-307).

The ABRE elements have been identified in many seed-specific promoters induding Em, a dass I Late Embryogenesis Abundant protein in *Arabidopsis* (Carles et al. (2002) Plant J. 30(3):373-83.), rab17 gene from maize (Busk et al. (1997) Plant J. 11(6):1285-95) and the *Brassica napus* storage protein gene napA (Ellerstrom et al. (1996) Plant Mol Biol. 32(6):1019-27).

As used herein, the E-box motif promoter element is defined as a promoter element which is a basic region helix-loop-helix with the sequence CANNTG in accordance with the consensus sequence for E-box motifs as defined by Yoder et al. (1999) Biochimica et Biophysica Acta 1446:403-413. The E-box element is found in seed-specific genes induding a cotton palmitoyl-acyl carrier protein (ACP) thioesterase (Fat B1) (Yoder et al. (1999) Biochimica et Biophysica Acta 1446: 403-413) and has shown to be involved in both tissue specific and developmental control of the *Phaseolus vulgaris* seed storage glycoprotein Phaseolin (Burrow, et al. (1992) Plant J 2: 537-548 and Kawagoe et al. (1994) Plant J 5: 885-890).

Finally the soybean embryo factor 3 (SEF3) responsive element has a consensus of AACCCA (Allen et al. (1989). Plant Cell 1: 623-631). The SEF3 element has been identified in the promoter of the _' subunit of the soybean_-conglycinin 7S seed storage protein (Allen et al. (1989) Plant Cell 1: 623-631).

In a preferred embodiment, the seed-specific promoter obtained from flax comprises at least one of the following promoter elements: an RY-repeat, an ABRE, and E-Box or an SEF3 element. In accordance with the present invention, the flax seed specific promoter preferably comprises an RY repeat and an ABRE. Preferably, the RY repeat and the ABRE are separated from each other by less than 100 nucleotides and more than 20 nucleotides. More preferably, the RY repeat and the ABRE are separated from each other by less than 50 nudeotides and more than 20 nucleotides and most preferably, the RY element and the ABRE are separated from each other less than 35 nudeotides and more than 20 nucleotides.

In particular, the inventors have isolated and sequenced four seed-specific promoters from flax. The four promoters share structural similarities in that they all have an alternating purine-pyrimidine sequences (RY repeat) and abscisic acid-responsive element (ABRE) with similar spacing. In addition, the 2S and linin promoters both have the following four promoter elements: EBOX (CANNTG element), abscisic acid-responsive element (ABRE), soybean embryo factor 3 (SEF3), alternating purine-pyrimidine sequences (RY repeat) and the order of the elements is maintained. The two oleosin promoters share the promoter elements RY repeat and CACGTG sequence (which has ABRE as a sub-set) and the order of the elements is also maintained. The elements found in each of the four promoters are listed in the table below.

| Specification Figure | Promoter | Element | Nucleotides |
|---|---|---|---|
| 1 | 16 kDa oleosin promoter | RY repeat | 1817-1822 |
|  |  |  | 1821-1826 |
|  |  | ABRE element | 1880-1884 |
| 2 | 18.6 kDa oleosin promoter | RY repeat | 1677-1682 |
|  |  | ABRE element | 1711-1750 |
| 3 | 2S Storage protein promoter | RY repeat | 285-290 |
|  |  | ABRE element | 253-257 |
|  |  | EBOX | 234-239 |
|  |  | SEF3 | 269-274 |
| 4 | Linin promoter | RY repeat | 1888-1893 |
|  |  | ABRE element | 1860-1864 |
|  |  | EBOX | 1836-1841 |
|  |  | SEF3 | 1877-1882 |

In one embodiment the flax seed specific promoter of the present invention, in addition to the RY-repeat and the ABRE, comprises an EBOX element and a SEF3 element. The EBOX element is preferably located between 250 and 150 nudeotides from the "ATG" start codon. More preferably, the EBOX element is located between 200 and 175 nucleotides from the start codon and most preferably, the EBOX element is located are between 195 and 185 nudeotides, inclusive, from the "ATG" start codon. Preferably, the SEF3 element is located between 200 and 50 nucleotides from the "ATG" start codon. More preferably, the SEF3 element is located between 175 and 100 nucleotides from the start codon and most preferably, the SEF3 element is located between 160 and 145 nucleotides, inclusive, from the "ATG" start codon.

In a preferred embodiment, the seed specific promoter comprises:
(a) a nucleic acid sequence as shown in FIG. 1 (SEQ.ID.NO.:1), FIG. 2 (SEQ.ID.NO.:4), FIG. 3 (SEQ.ID.NO.:6) or FIG. 4 (SEQ.ID.NO.:8) wherein T can also be U;
(b) a nucleic add sequence that is complimentary to a nucleic acid sequence of (a);
(c) a nucleic acid sequence that has substantial sequence homology to a nucleic acid sequence of (a) or (b);
(d) a nucleic acid sequence that is an analog of a nucleic acid sequence of (a), (b) or (c); or
(e) a nucleic add sequence that hybridizes to a nucleic add sequence of (a), (b), (c) or (d) under stringent hybridization conditions.

The term "sequence that has substantial sequence homology" means those nucleic acid sequences which have slight or inconsequential sequence variations from the sequences in (a) or (b), i.e., the sequences function in substantially the same manner and are capable of driving seed specific expression of non-native nucleic acid sequences. The variations may be attributable to local mutations or structural modifications. Nucleic acid sequences having substantial homology include nucleic acid sequences having at least 65%, more preferably at least 85%, and most preferably 90-95% identity with the nucleic acid sequences as shown in FIG. 1 (SEQ.ID.NO.:1), FIG. 2 (SEQ.ID.NO.:4), FIG. 3 (SEQ.ID.NO.:6) or FIG. 4 (SEQ.ID.NO.:8). Sequence identity can be calculated according to methods known in the art. Sequence identity is most preferably assessed by the algorithm of BLAST version 2.1 advanced search. BLAST is a series of programs that are available online www.ncbi.nlm.nih.gov/BLAST. The advanced blast search www.ncbi.nlm.nih.gov/blast/blast.cgi?Jform=1) is set to default parameters. (i.e., Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

The term "sequence that hybridizes" means a nucleic add sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic add molecules in solution. Hybridization may occur to all or a portion of a nucleic add sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic add, length of nucleic acid probe (I), and temperature (Tm=81.5° C.-16.6 (Log 10 [Na+])+0.41(%(G+C)−600/1). Accordingly, the parameters in the wash conditions that determine hybrid stability are sodium ion concentration and temperature. In order to identify molecules that are similar, but not identical, to a known nucleic add molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5×sodium chloride/sodium citrate (SSC)/5× Denhardt's solution/1.0% SDS at Tm (based on the above equation) −5° C., followed by a wash of 0.2×SSC/0.1% SDS at 60° C.

The term "a nucleic acid sequence which is an analog" means a nucleic acid sequence which has been modified as compared to the sequence of (a), (b) or (c) wherein the modification does not alter the utility of the sequence (i.e. as a seed specific promoter) as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in FIG. 1 (SEQ ID NO:1), FIG. 2 (SEQ ID NO:4), FIG. 3 (SEQ ID NO:6) or FIG. 4 (SEQ ID NO:8) with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in FIG. 1 (SEQ ID NO:1), FIG. 2 (SEQ ID NO:4), FIG. 3 (SEQ ID NO:6) or FIG. 4 (SEQ ID NO:8). For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nudeotides may have morpholino backbone structures (U.S. Pat. No. 5,034,506). The analogs may also contain groups such as reporter groups, a group for improving the pharmacokinetic or pharmacodynamic properties of nucleic acid sequence.

In a specific embodiment, the promoter is selected from the group of promoters consisting of FIG. 1 (SEQ ID NO:1), FIG. 2 (SEQ ID NO:4), FIG. 3 (SEQ ID NO:6) and FIG. 4 (SEQ ID NO:8) or a nucleic acid sequence hybridizing thereto under stringent conditions.

In another aspect, the invention provides chimeric nucleic acid sequences comprising a first nucleic acid sequence obtained from flax operatively linked to a second nucleic acid sequence non-native to said first nucleic acid sequence wherein said first nucleic acid sequence comprises a novel flax seed-specific promoter.

In accordance with the present invention, the chimeric nucleic acid sequences can be incorporated in a known manner in a recombinant expression vector which ensures good expression in the seed cell. Accordingly, the present invention includes a recombinant expression vector comprising a chimeric nucleic acid sequence of the present invention suitable for expression in a seed cell.

The term "suitable for expression in a seed cell" means that the recombinant expression vectors contain the chimeric nucleic acids sequence of the invention, a regulatory region and a termination region, selected on the basis of the seed cell to be used for expression, which is operatively linked to the nucleic acid sequence encoding the polypeptide of desirable amino acid composition. Operatively linked is intended to mean that the chimeric nucleic acid sequence encoding the polypeptide is linked to a regulatory sequence and termination region which allows expression in the seed cell. A typical construct consists, in the 5' to 3' direction of a regulatory region complete with a promoter capable of directing expression in a plant, a polypeptide coding region and a transcription termination region functional in plant cells. These constructs may be prepared in accordance with methodology well known to those of skill in the art of molecular biology (see for example: Sambrook et al. (1990), Molecular Cloning, $2^{nd}$ ed. Cold Spring Harbor Press). The preparation of constructs may involve techniques such as restriction digestion, ligation, gel electrophoresis, DNA sequencing and PCR. A wide variety of cloning vectors is available to perform the necessary cloning steps. Especially suitable for this purpose are the cloning vectors with a replication system that is functional in *Escherichia coli* such as pBR322, the pUC series M13mp series, pACYC184, pBluescript etc. Nucleic add sequences may be introduced into these vectors and the vectors may be used to transform *E. coli* which may be grown in an appropriate medium. Plasmids may be recovered from the cells upon harvesting and lysing the cells. Final constructs may be introduced into plant vectors compatible with integration into the plant such as the Ti and Ri plasmids.

II. Methods

As hereinbefore mentioned, the present invention relates to improved methods for the expression of non-native genes in plants, in particular flax. The invention provides methods allowing the seed-specific expression of non-native genes in flax and other plants. The methods of the invention are advantageous in that improved control over the expression of non-native genes in seeds is obtained. Expression of the non-native gene is restricted to the seeds, thereby limiting potential undesirable effects resulting from the expression in other plant organs or tissues. In addition, the provided methodology allows improved control over expression characteristics, such as the expression level of the non-native gene and timing of expression of the non-native gene in the developmental cycle of the plant. The methods of the present invention are particularly useful in that in accordance with the present invention the seed composition with respect to valuable raw materials, such as oil, protein and polysaccharides, may be altered both qualitatively and quantitatively.

Accordingly, in one aspect, the invention provides a method for the expression of a nucleic add sequence of interest in plant seeds comprising:

(a) preparing a chimeric nucleic acid construct comprising in the 5' to 3' direction of transcription as operably linked components;
(1) a seed-specific promoter obtained from flax; and
(2) the nucleic acid sequence of interest wherein said nucleic acid of interest is non-native to said flax seed-specific promoter;
(b) introducing said chimeric nucleic acid construct into a plant cell; and
(c) growing said plant cell into a mature plant capable of setting seed, wherein said nucleic acid sequence of interest is expressed in the seed under the control of said flax seed-specific promoter.

As used herein, the term "non-native" refers to any nucleic acid sequence, including any RNA or DNA sequence, which is not normally associated with the seed-specific promoter. This includes heterologous nucleic acid sequences which are obtained from a different plant species as the promoter as well as homologous nucleic acid sequences which are obtained from the same plant species as the promoter but are not associated with the promoter in the wild-type (non-transgenic) plant.

The non-native nucleic acid sequence when linked to a seed-specific promoter obtained from flax results in a chimeric construct. The chimeric construct is introduced into a flax plant cell to create a transgenic flax plant cell which results in a detectably different phenotype of the flax plant cell or flax plant grown from it when compared with a non-transgenic flax plant cell or flax plant grown from it. A contiguous nucleic acid sequence identical to the nucleic add sequence of the chimeric construct is not present in the non-transformed flax plant cell or flax plant grown from it. In this respect, chimeric nucleic acid sequences include those sequences which contain a flax promoter linked to a nucleic acid sequence obtained from another plant species or a nucleic acid sequence from flax but normally not associated with that promoter. Chimeric nucleic acid sequences as used herein further include sequences comprising a flax promoter and a nucleic acid sequence that is normally linked to the promoter but additionally containing a non-native nucleic acid sequence. For example, if the promoter is a flax seed-specific oleosin promoter, sequences "non-native" to the flax oleosin promoter also include a sequence comprising a fusion between the flax oleosin gene naturally associated with the oleosin promoter, and a coding sequence of interest that is not naturally associated with the promoter. The term non-native is also meant to include a fusion gene as hereinabove which additionally includes a cleavage sequence separating the nucleic acid sequence that is normally linked to the promoter sequence and the gene encoding the protein of interest.

The term "nucleic acid sequence" refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine. The methods for the expression of non-native genes in flax seeds in accordance with the present invention may be practiced using any flax seed-specific promoter and are not limited by the specific flax seed specific promoter that is selected. Preferred flax seed-specific promoters are described in Section I. In preferred embodiments of the present invention, the flax seed-specific promoter confers to the non-native nucleic acid sequence at least one expression characteristic which is similar or identical to an expression characteristic conferred to the native nucleic acid sequence by the native promoter.

The term "expression characteristic" as used herein refers to any measurable property or effect conferred by the flax seed-specific promoter to the nucleic acid sequence operably linked to the flax seed-specific promoter. Thus in preferred embodiments, timing of expression in the plant's life cycle, of the non-native nucleic acid sequence is similar or identical to timing of expression of the native nucleic acid sequence. In further preferred embodiments, the expression level of the heterologous nucleic add sequence is similar or identical to the expression level of the native nucleic acid sequence. In yet further specific embodiments, the response of the non-native gene to alterations in lighting conditions, changes in wavelength or light intensity for example, changes in temperature, tissue wounding, changes in concentration of chemical agents, such as for example phytohormones and pesticides, is similar to the response of the native nucleic add sequence to these stimuli. Other desired expression characteristics conferred by a flax seed-specific promoter may be recognized by those skilled in the art and a flax seed-specific promoter may be selected accordingly.

Flax-seed specific promoters that may be used in accordance with the present invention include promoters associated with seed storage proteins, such as all albumins and globulins, including the vicilin and legumin-like proteins, as well as seed-specific promoters not associated with seed storage proteins, such as oleosins. Of further particular interest are promoters associated with fatty acid metabolism, such as acyl carrier protein (ACP), saturases, desaturases, elongases and the like.

The flax seed-specific promoter preferably comprises one or more of the following promoter elements purine-pyrimidine sequences (RY repeats), abscisic acid-responsive elements (ABRE), E-Box elements (CANNTG element) and soybean embryo factor 3 elements (SEF3). In preferred embodiments of the present invention the seed specific promoter used is an oleosin promoter, a legumin-like seed storage protein promoter or a 2S storage protein promoter. In particularly preferred embodiments the seed specific promoter has the sequence shown in FIG. 1 (SEQ ID NO:1), FIG. 2 (SEQ ID NO:4), FIG. 3 (SEQ ID NO:6) or FIG. 4 (SEQ ID NO:8) or any nucleic add sequences obtainable from flax and hybridizing to any one of these four nucleic add sequences under stringent conditions.

The present invention further provides methods of use for the novel promoters shown in FIG. 1 (SEQ.ID.NO.:1), FIG. 2 (SEQ.ID.NO.:4), FIG. 3 (SEQ.ID.NO.:6) and FIG. 4 (SEQ.ID.NO.:8) in all plant species including flax. Accordingly, the invention also includes the preparation of chimeric nucleic acid constructs comprising a promoter selected from the group promoters shown in FIG. 1 (SEQ ID NO:1), FIG. 2 (SEQ ID NO:4), FIG. 3 (SEQ ID NO:6) and FIG. 4 (SEQ ID NO:8) and a nucleic add sequence of interest, and expression in a seed-specific manner of the nucleic add sequence of interest in a plant species such as flax and under the control of the flax promoter.

Accordingly, in a specific embodiment there is provided a method for the expression of a nucleic acid sequence of interest in plant seeds comprising:
(a) preparing a chimeric nucleic add construct comprising in the 5' to 3' direction of transcription as operably linked components;
(1) a seed-specific promoter selected from the group of seed- specific promoters consisting of
(i) a nucleic add sequence as shown in FIG. 1 (SEQ.ID.NO.:1), FIG. 2 (SEQ.ID.NO.:4), FIG. 3 (SEQ.ID.NO.:6) or FIG. 4 (SEQ.ID.NO.:8) wherein T can also be U;
(ii) a nucleic acid sequence that is complimentary to a nucleic add sequence of (i);
(iii) a nucleic acid sequence that has substantial sequence homology to a nucleic acid sequence of (i) or (ii); and
(iv) a nucleic acid sequence that is an analog of a nucleic add sequence of (i), (ii) or (iii);
(v) a nucleic add sequence that hybridizes to a nucleic add sequence of (i), (ii), (iii) or (iv) under stringent hybridization conditions; and
(2) said nucleic acid of interest;
(b) introducing the chimeric nucleic acid construct into a plant cell;
(c) growing said plant cell into a mature plant capable of setting seed, wherein said nucleic acid sequence of interest is expressed in the seed under the control of said seed-specific promoter.

Additional flax seed-specific promoters may be used in accordance with the present invention. These promoters may be obtained in a number of ways. Where a flax seed protein has been isolated, it may be partially sequenced, so that a nucleic acid probe may be designed for identifying RNA specific to the seed. To further enhance the RNA specifically associated with the seed, cDNA may be prepared from seed cells and the cDNA may be subtracted with mRNA or cDNA from non-seed cells. The remaining seed cDNA may then be used to probe a genomic DNA library for complementary sequences. Sequences hybridizing to the cDNA may subsequently be obtained and the associated promoter region may be isolated. It is also possible to screen genomic DNA libraries prepared from flax seed tissues using known seed specific genes from other plant species and subsequently isolate their associated promoters. Due to the relative abundance of seed-storage proteins in seeds it is also be possible to obtain sequence information through random sequencing of flax seed cDNA libraries. Those cDNA sequences matching sequence of known seed-storage proteins could be used to identify the associated promoter. Databases containing sequence information from large scale sequencing from for example *Arabidopsis* and maize may be searched for known seed-specific proteins and/or promoters and the information may be used to identify promoter sequences in flax that share sequence similarity. Alternative methods to isolate additional flax seed specific promoters may be used and novel flax seed specific promoters may be discovered by those skilled in the art and used in accordance with the present invention.

The nucleic acid sequence of interest linked to the promoter may be any nucleic acid sequence of interest including any RNA or DNA sequence encoding a peptide or protein of interest, for example, an enzyme, or a sequence complementary to a genomic sequence, where the genomic sequence may be at least one of an open reading frame, an intron, a non-coding leader sequence, or any sequence where the complementary sequence will inhibit transcription, messenger RNA processing, for example splicing or translation. The nucleic acid sequence of interest may be synthetic, naturally derived or a combination thereof. As well, the nucleic acid sequence of interest could be a fragment of the natural sequence, for example just include the catalytic domain or a structure of particular importance. Depending upon the nature of the nucleic acid sequence of interest, it may be desirable to synthesize the sequence with plant preferred codons. The plant preferred codons may be determined from the codons of highest frequency in the proteins expressed in the largest amount in particular plant species of interest.

The nucleic acid sequence of interest may encode any of a variety of recombinant proteins. Examples of recombinant proteins which might be expressed by the methods of the present invention include proteins with a favorable catalytic function or a valuable protein that will accumulate to high levels and be extracted if desired. Proteins with a catalytic function, include, but are not limited to, proteins that confer a new biochemical phenotype on the developing seeds. New phenotypes could include such modifications as altered seed-protein or seed oil composition or seed polysaccharide composition, enhanced production of pre-existing desirable products or properties and the reduction or even suppression on an undesirable gene product using antisense, ribozyme or co-supression technologies (Izant and Weintraub (1984) Cell 26: 1007-1015, antisense; Hazelhoff and Gerlach (1988) Nature 334: 585-591, ribozyme; Napoli et al. (1990) Plant Cell 2: 279-289, co-suppression).

It is expected that the desired proteins would be expressed in all embryonic tissues, although varying cellular expression may be detected in the different embryonic tissues such as the embryonic axis and cotyledons. The nucleic acid sequence of interest may be expressed at any stage in seed development. The timing of expression may depend on the particular use of the invention. Expression of enzymes involved in oil modification may be desirable early in seed development, for example before accumulation of seed storage protein.

Besides the promoter region and the nucleic acid sequence of interest, a nucleic acid sequence capable of terminating transcription is typically included in expression vectors. Transcriptional terminators are preferably about 200 to about 1,000 nucleotide base pairs and may comprise any such sequences functional in plants, such as the nopaline synthase termination region (Bevan et al., (1983) Nud. Add. Res. 11: 369-385), the phaseolin terminator (van der Geest et al., (1994) Plant J. 6(3): 413-423), the terminator for the octopine synthase gene of *Agrobacterium tumefaciens* or other similarly functioning elements. These transcription terminator regions can be obtained as described by An (1987), Methods in Enzym. 153: 292 or are already present in plasmids available from commercial sources such as ClonTech, Palo Alto, Calif. The choice of the appropriate terminator may have an effect of the rate of transcription.

The chimeric construct may further comprise enhancers such as the AMV leader (Jobling and Gehrke (1987), Nature 325: 622-625) or introns. It should be understood that the design of the expression vector may depend on such factors as the choice of the plant species and/or the type of polypeptide to be expressed.

The expression vectors will normally also contain a marker gene. Marker genes comprise all genes that enable distinction of transformed plant cells from non-transformed cells, including selectable and screenable marker genes. Conveniently, a marker may be a resistance marker to a herbicide, for example, glyphosate or phosphinothridn, or to an antibiotic such as kanamycin, G418, bleomycin, hygromycin, chloramphenicol and the like, which confer a trait that can be selected for by chemical means. Screenable markers 3 0 may be employed to identify transformants through observation. They include but are not limited to the β-glucuronidase or uidA gene, a β-lactamase gene or a green fluorescent protein (Niedz et al. (1995) Plant Cell Rep. 14: 403).

In order to introduce nucleic acid sequences into plant cells in general a variety of techniques are available to the skilled artisan. *Agrobacterium*-mediated transformation for flax plant cells has been reported and flax transformants may be obtained in accordance with the methods taught by Dong and McHughen (1993) Plant Science 88: 61-77, although a variety of other techniques (see below) may also be used to introduce the chimeric DNA constructs in flax cells if so desired.

Transformed flax plants grown in accordance with conventional agricultural practices known to a person skilled in the art are allowed to set seed. Flax seed may then be obtained from mature flax plants and analyzed for desired altered properties with respect to the wild-type seed.

Two or more generations of plants may be grown and either crossed or selfed to allow identification of plants and strains with desired phenotypic characteristics including production of the recombinant polypeptide. It may be desirable to ensure homozygosity in the plants to assure continued inheritance of the recombinant trait. Methods for selecting homozygous plants are well known to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means (e.g. treatment with colchicine or other microtubule disrupting agents).

The present invention also includes transgenic plant seeds prepared according to a method comprising:
  (a) preparing a chimeric nucleic acid construct comprising in the 5' to 3' direction of transcription as operably linked components:
  (1) a seed-specific promoter obtained from flax; and
  (2) a nucleic acid sequence of interest wherein said nucleic add of interest is non-native to said seed-specific promoter;
  (b) introducing said chimeric nucleic acid construct into a plant cell; and
  (c) growing said plant cell into a mature plant capable of setting seed
  wherein said nucleic acid sequence of interest is expressed in the seed under the control of said seed-specific promoter.

The "seed-specific promoter obtained from flax" is as defined previously in Section I. In preferred embodiments of the invention the seed-specific promoter is selected from the group of flax seed specific promoters consisting of, a 2S storage protein promoter, a globulin promoter, an oleosin promoter, and a legumin-like seed storage protein promoter. Specific promoter sequences are shown in FIG. 1 (SEQ.ID.NO.:1), FIG. 2 (SEQ.ID.NO.:4), FIG. 3 (SEQ.ID.NO.: 6) and FIG. 4 (SEQ.ID.NO.:8).

The present invention further provides plants capable of setting seed prepared by a method comprising:

(a) preparing a chimeric nucleic acid construct comprising in the 5' to 3' direction of transcription as operably linked components:
  (1) a seed-specific promoter obtained from flax; and
  (2) a nucleic acid sequence of interest wherein said nucleic acid of interest is non-native to said seed-specific promoter;
(b) introducing said chimeric nucleic acid construct into a plant cell; and
(c) growing said flax plant cell into a mature plant capable of setting seed
  wherein said nucleic acid sequence of interest is expressed in the seed under the control of said seed-specific promoter.

A variety of techniques are available for the introduction of nucleic acid sequences, in particular DNA, into plant host cells in general. For example, the chimeric DNA constructs may be introduced into host cells obtained from dicotelydenous plants, such as tobacco, and oleoagenous species, such as *Brassica napus* using standard *Agrobacterium* vectors by a transformation protocol such as described by Moloney et al. (1989), Plant Cell Rep. 8: 238-242 or Hinchee et al. (1988) Bio/Technol. 6: 915-922; or other techniques known to those skilled in the art. For example, the use of T-DNA for transformation of plant cells has received extensive study and is amply described in EP 0 120 516, Hoekema et al., (1985), Chapter V In: *The Binary Plant Vector System* Offset-drukkerij Kanters B V, Alblasserdam); Knauf et al. (1983), *Genetic Analysis of Host Expression by Agrobacterium*, p. 245, In: *Molecular Genetics of Bacteria-Plant Interaction*, Puhler, A. ed. Springer-Verlag, NY); and An et al., (1985), (EMBO J., 4: 277-284). *Agrobacterium* transformation may also be used to transform monocot plant species (U.S. Pat. No. 5,591,616).

Conveniently, explants may be cultivated with *Agrobacterium tumefaciens* or *Agrobacterium rhizogenes* to allow for the transfer of the transcription construct in the plant host cell. Following transformation using *Agrobacterium* the plant cells are dispersed into an appropriate medium for selection, subsequently callus, shoots and eventually plants are recovered. The *Agrobacterium* host will harbour a plasmid comprising the vir genes necessary for transfer of the T-DNA to plant cells. For injection and electroporation (see below) disarmed Ti-plasmids (lacking the tumour genes, particularly the T-DNA region) may be introduced into the plant cell.

The use of non-*Agrobacterium* techniques permits the use of constructs described herein to obtain transformation and expression in a wide variety of monocotyledonous and dicotyledonous plant species. These techniques are especially useful for transformation of plant species that are intractable in an *Agrobacterium* transformation system. Other techniques for gene transfer include particle bombardment (Sanford, (1988), Trends in Biotechn. 6: 299-302), electroporation (Fromm et al., (1985), PNAS USA, 82: 5824-5828; Riggs and Bates, (1986), PNAS USA 83: 5602-5606), PEG mediated DNA uptake (Potrykus et al., (1985), Mol. Gen. Genetics., 199: 169-177), microinjection (Reich et al., Bio/Techn. (1986) 4:1001-1004) and silicone carbide whiskers (Kaeppler et al. (1990) Plant Cell Rep. 9: 415-418).

In a further specific applications such as to *B. napus*, the host cells targeted to receive recombinant DNA constructs typically will be derived from cotyledonary petioles as described by Moloney et al. (1989) Plant Cell Rep. 8: 238-242. Other examples using commercial oil seeds include cotyledon transformation in soybean explants (Hinchee et al., (1988) Bio/Technol. 6: 915-922) and stem transformation of cotton (Umbeck et al., (1987) Bio/Technol. 5: 263-266).

Following transformation, the cells, for example as leaf discs, are grown in selective medium. Once the shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, to show integration into the genome of the host cell.

The methods provided by the present invention can be used in conjunction a broad range of plant species. Particularly preferred plant cells employed in accordance with the present invention include cells from the following plants: soybean (*Glycine max*), rapeseed (*Brassica napus, Brassica campestris*), sunflower (*Helianthus annuus*), cotton (*Gossypium hirsutum*), corn (*Zea mays*), tobacco (*Nicotiana tobacum*), alfalafa (*Medicago sativa*), wheat (*Triticum* sp.), barley (*Hordeum vulgare*), oats (*Avena sativa* L.), sorghum (*Sorghum bicolor*), *Arabidopsis thaliana*, potato (*Solanum* sp.), flax/linseed (*Linum usitatissimum*), safflower (*Carthamus tinctorius*), oil palm (*Eleais guineeis*), groundnut (*Arachis hypogaea*), Brazil nut (*Bertholletia excelsa*) coconut (*Cocus nucifera*), castor (*Ricinus communis*), coriander (*Coriandrum sativum*), squash (*Cucurbita maxima*), jojoba (*Simmondsia chinensis*) and rice (*Oryza sativa*). Preferably the plant is flax/linseed (*Linum usitatissimum*) or safflower (*Carthamus tinctorius*).

The present invention has a variety of uses which include improving the intrinsic value of plant seeds by their accumulation of altered polypeptides or novel recombinant peptides or by the incorporation or elimination or a metabolic step. Use of the invention may result in improved protein quality (for example, increased concentrations or essential or rare amino acids), improved liquid quality by a modification of fatty acid composition, or improved or elevated carbohydrate composition. Examples include the expression of sulfur-rich proteins, such as those found in lupins or brazil nuts in a seed deficient in sulphurous amino acids. Improved protein quality could also be achieved by the expression of a protein or a fragment of a protein that is enriched in essential amino acids including lysine, cysteine, methionine and tryptophan. Alternatively, a fatty acyl coenzyme A, a transferase enzyme capable of modifying fatty acid ratios in triglycerides (storage lipid) could be expressed. In cases where a recombinant protein is allowed to accumulate in the seed, the protein could also be a peptide which has pharmaceutical or industrial value. In this case the peptide could be extracted from the seed and used in crude or purified form as appropriate for the intended use. As well, the polypeptides that are expressed in the seeds can be fragments or derivatives or the native protein. Pharmaceutically useful proteins may include, but are not limited to, anticoagulants, such as hirudin, antibodies, including monoclonal antibodies and antibody fragments, vaccines, cytokines or growth factors such as bovine growth factor, cholinergic differentiation factor (CDF), ciliary neurotrophic factor (CNTF), fibroblast growth factor (FGF), fish growth factor, gonadotropin, granulocyte-colony stimulating factor (G-CSF), granulocyte-macrophage colony-stimulating factor (GM-CSF), human growth hormone, interferon alpha (IFN-α), interferon beta (IFN-β), interferon gamma (IFN-γ), interleukin 1-alpha (IL1-α), interleukin 1-beta (IL1-β), interleukin-2 (IL-2), interleukin-3 (IL-3), interleukin-4 (IL-4), interleukin-5 (IL-5), interleukin-6 (IL-6), interleukin-10 (IL-10), leukemia inhibitory factor (LIF), thioredoxin, macrophage colony-stimulating factor (M-CSF), myelomonocytic growth factor, nerve growth factor (NGF), oncostatin M, platelet-derived growth factor (PDGF), prolactin, transforming growth factor alpha (TGF-α), transforming growth factor beta2 (TGF-β2), tumour necrosis factor alpha (TNF-α), and tumour necrosis factor beta (TNF-β). Pharmaceutically useful proteins can also include mammalian proteins, for example, but not limited to α-1-antitrypsin, anti-obesity proteins, blood proteins, collagen, collagenase, elastin, elastase, enteropeptidase, fibrinogen, haemoglobin, human serum albumin, insulin, lactoferrin, myoglobin and pulmonary surfactant proteins.

Industrially useful peptides may include, but are not limited to α-amylase or other amylases, amyloglucosidase, arabinase, catalase, cellobiohydrolase, cellulases, chitinases, chymotrypsin, dehydrogenases, endo-glucanase, chymosin, endo-galactanase, esterases, β-galactosidase, α-galactosidase or other galactosidases, gastric lipases, glucanases, glucose isomerase, hemi-cellulases, hydrolases, isomerase, ligninases, lipases, lyases, lysozymes, oxidases, oxidoreductase, papain, pectinases, pectin lyase, peroxidases, phosphatases, phytase, proteases, pullulanases, reductases, serine proteases, thioredoxin, transferase, trypsin, and xylanase.

The following non-limiting examples are illustrative of the present invention:

EXAMPLES

Example 1

Isolation of Seed-Specific Flax Promoters

Seed specific cDNA clones were isolated form a flax seed specific cDNA-library. These cDNA clones were sequenced and the Basic Local Alignment Search Tool (BLAST) was used to compare these sequences against others in public databases such as Genbank. This comparison revealed that the deduced amino acid sequence of several of the isolated cDNAs had a high degree of similarity to both the low and high molecular weight dass of oleosins, 2S-albumin and legumin-like storage proteins. Probes were prepared individually from (portions of) cDNAs encoding oleosins, 2S albumin and legumin-like storage proteins and these were used to screen a genomic library prepared from the flax line Forge that is homozygous for four rust resistance genes (Anderson et al. (1997), The Plant Cell 9: 641-651). Several positive lambda clones for each probe were identified after high-stringency screening. The inserts were subcloned into the plasmid vector pBluescript and sequenced. Sequence information revealed that we had isolated the genomic counterparts to the oleosins, 2S albumin and cDNAs legumin-like cDNAs. Sequence information of the genomic clones containing sequences encoding a high and low molecular weight oleosin isoforms, 2S albumin and a legumin-like gene are presented in FIGS. 1 to 4 respectively.

FIG. 1 and SEQ.ID.NO.:1 shows the DNA sequence of a flax genomic clone encoding a 16.0 kDa oleosin protein (low molecular weight or L-isoform). Putative regulatory elements are identified and indicated. These include inverted repeats (base pairs 805 to 813 and 821 to 829; base pairs 1858 to 1866 and 1877 to 1885), direct repeats (base pairs 184 to 193 and 1102 and 1111; base pairs 393 to 402 and 1701 to 1710; base pairs 683 to 692 and 1546 to 1555; base pairs 770 to 781 and 799 to 810; base pairs 955 to 964 and 1936 to 1945; base pairs 1483 to 1496 and 1513 to 1526), the abscisic add responsive element (ABRE) (base pairs 1859 to 1866), CACA box (base pairs 1933 to 1936), TATA box (base pairs 1925 to 1931) and CAT box (base pairs 1989 to 1993). As well, the poly adenylation signal is indicated (base pairs 3020 to 3025). The open reading frame is interrupted by 1 short intron (which are marked) and the 2 exons are translated and indicated in IUPAC single letter amino-acid codes.

FIG. 2 and SEQ.ID.NO.:4 shows the DNA sequence of a flax genomic clone encoding a 18.6 kDa oleosin protein (high molecular weight or H-isoform). Putative regulatory elements are identified and indicated. These include direct repeats (base pairs 14 to 25 and 1427 to 1438; base pairs 80 to 89 and 1242 to 1251; base pairs 177 to 186 and 837 to 846; base pairs 1281 to 1290 and 1242 to 1251; base pairs 1591 to 1600 and 1678 to 1287). The open reading frame is not interrupted by introns and is translated and indicated in IUPAC single letter amino-acid codes.

FIG. 3 and SEQ.ID.NO.:6 shows the DNA sequence of the flax genomic clone encoding a 2S storage protein. Nucleotide sequencing of this clone revealed it to have an open reading frame of 174 amino acids that showed homology to the plant 2S storage group of proteins. The sequence encodes an open reading frame with 38% overall similarity to a *Brassica oleracea* 2S storage protein, including complete conservation of the glutamine-rich stretch QQQGQQQGQQQ (SEQ.ID.NO.:13). In addition, the 2S storage protein gene promoter contained several putative promoter regulatory elements. These include AT rich repeats (base pairs 25-36, 97-108 and 167-190), RY-like repeat (base pairs 240-247), G-box-like element (base pairs 274-280), seed specific box-like motif (base pairs 285-290) and TATA box (base pairs 327-333).

FIG. 4 and SEQ.ID.NO.:8 shows the DNA sequence of a flax genomic clone encoding a 54.4 kDa flax legumin-like seed storage protein. This legumin-like seed storage protein gene will also be referred to as "linin". The deduced amino add sequence of the linin gene was compared to the legumin-like protein from *R. communis*, the legumin precursor from *M. salicifolia, Q.robur* and *G. hirsutum*, the glutelin precursor from *O.sativa* and a 12 S seed storage protein from *A. thaliana*. The linin gene shows a sequence identity/similarity with the corresponding proteins from *R. communis, M. salicifolia, Q.robur, G. hirsutum, O.sativa* and *A. thaliana* of 59/15, 47/16, 50/17, 45/17, 43/18 and 43/18 percent respectively. Putative regulatory elements in the promoter region are identified and indicated. These indude inverted repeats (base pairs 265 to 276 and 281 to 292; base pairs 513 to 524 and 535 to 545), repeats (base pairs 1349 to 1360 and 1367 to 1378; base pairs 1513 to 1529 and 1554 to 1572), the abscisic add responsive element (ABRE) (base pairs 1223 and 1231), legumin box (RY repeats) (between base pairs 1223 and 1231), a possible vicilin box region (base pairs 1887 to 1894), CAAT box (base pairs 1782 to 1785) and TATA box (base pairs 1966 to 1970). As well, the signal peptide for ER membrane targeting is indicated (base pairs 2034-2080). The open reading frame is interrupted by 3 short introns (which are marked) and the 4 exons are translated and indicated in IUPAC single letter amino-acid codes.

FIG. 5 shows Southern blot analysis of flax genomic DNA. 60 μg of flax genomic DNA was isolated from leaves, digested with EcoRI (lane I), HindIII (lane 2) and BamHI (lane 3) and was loaded into the respective lanes. A) Hybridizations were performed with random primed $^{32}$P-labelled 3T cDNA (high molecular weight flax oleosin isoform). B) Hybridizations were performed with random primed 32P-labelled 7R cDNA (low molecular weight flax oleosin isoform). The results demonstrate that both 3T (high molecular weight oleosin isoform) and 7R (low molecular weight oleosin isoform) oleosin cDNAs hybridize with flax genomic DNA. More specifically the results indicate that 3T is likely to represent a 2-copy gene in flax, as seen by two bands in each lane of digestion. Similarly, 7R is likely to represent a multigene family in flax as multiple bands were detected for each digestion.

Example 2

Seed Specific Expression of Flax Oleosin Genes

Figure 6:
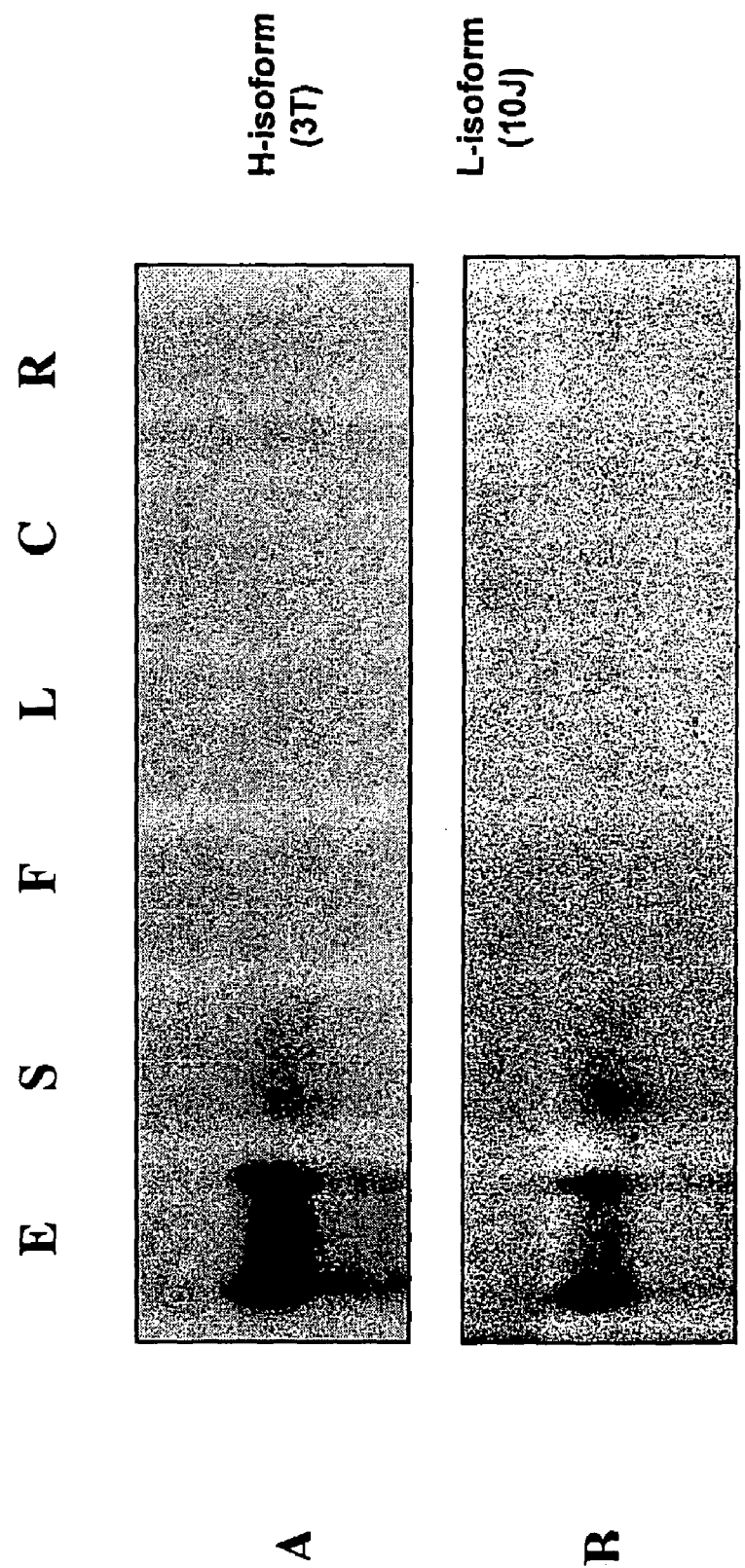
FIG. 6 shows a Northern blot analysis of the seed specific expression of flax oleosins.

FIG. 6 shows a Northern blot analysis of the seed specific expression of flax oleosins. Northern hybridization of the two oleosin mRNA in different tissues. Ten µg of total RNA was extracted from different tissues, R, root; C, cotyledon; L, leaf; S, seed capsule; E, embryo. The membrane was probed with (A) cDNA encoding high molecular weight (H)-isoform (identical to coding sequence as presented in FIG. 2) and (B) cDNA encoding low molecular weight (L)-isoform (identical to coding sequence as presented in FIG. 1). Both the transcripts are expressed only in the embryo and seed capsule, which contains embryos.

Example 3

Developmental Expression of Flax Oleosin Genes During Seed Development

Figure 7:
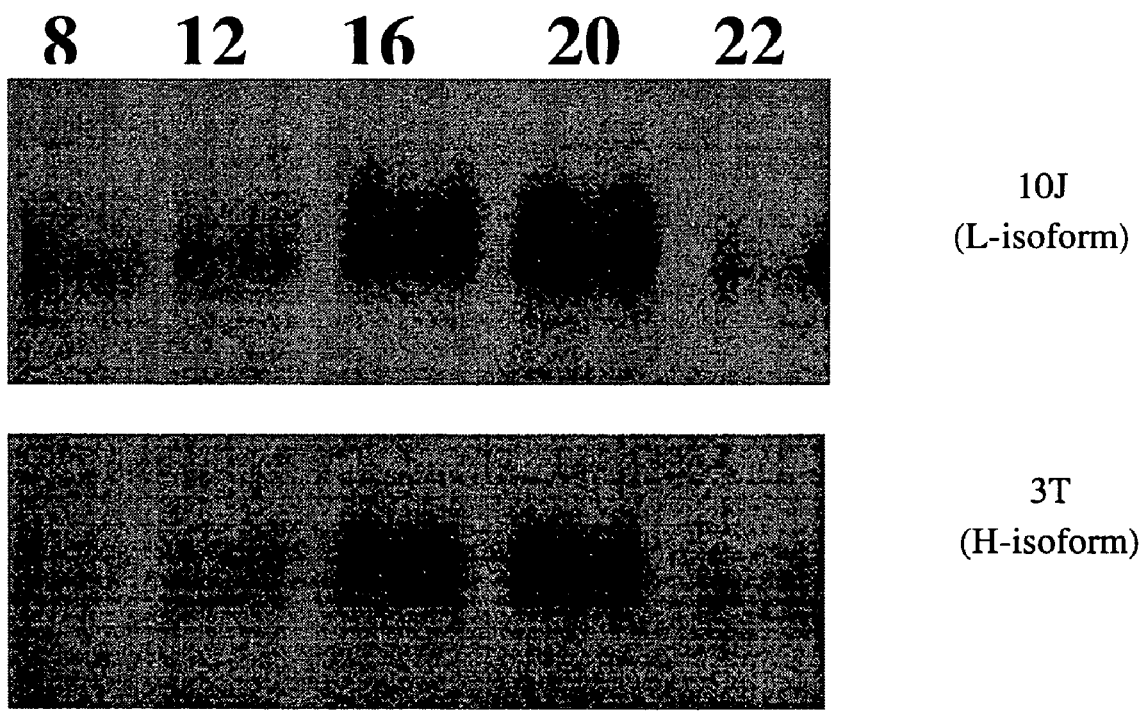
FIG. 7 shows a Northern blot analysis of the developmental expression of flax oleosins during seed development.

FIG. 7 shows a Northern blot analysis of the developmental expression of flax oleosins during seed development. 15 µg per lane of total RNA was loaded in each lane on agarose/formaldehyde gel and blotted onto HybondN+ membrane. 10J: This membrane was probed using the $^{32}$P dCTP labeled flax oleosin cDNA clone (low molecular weight isoform). Stages indicated are the number of days past anthesis (DPA). 3T) 15 µg per lane of total RNA was loaded in each lane on agarose/formaldehyde gel and blotted onto HybondN+ membrane. 3T: This membrane was probed using the $^{32}$P dCTP labeled flax oleosin cDNA clone (high molecular weight isoform). Both the transcripts were expressed very early in development (6DPA, early cotyledonary stage). Expression is maximum at 16 to 20 DPA (late cotyledonary stage) and declines at 22 DPA (mature embryos).

Example 4

Transient Seed specific Expression of β-glucuronidase (GUS) when under the Regulatory Control of Flax Oleosin Regulatory Sequences Two constructs were made using standard molecular biology techniques (eg see Sambrook et al. (1990), Molecular Cloning, 2nd ed. Cold Spring Harbor Press, including restriction enzyme digestions, ligation and polymerase chain reaction (PCR).

Construct pSC54: The β-glucuronidase reporter coding sequence from vector GUSN358>S (Clontech Laboratories) was placed between the promoter sequence from nucleotide 21 to 1852 and terminator sequence from 2395 to 3501 (as described in FIG. 1). This insert was cloned into pBluescript and the resulting vector is called pSC54

Figure 8:
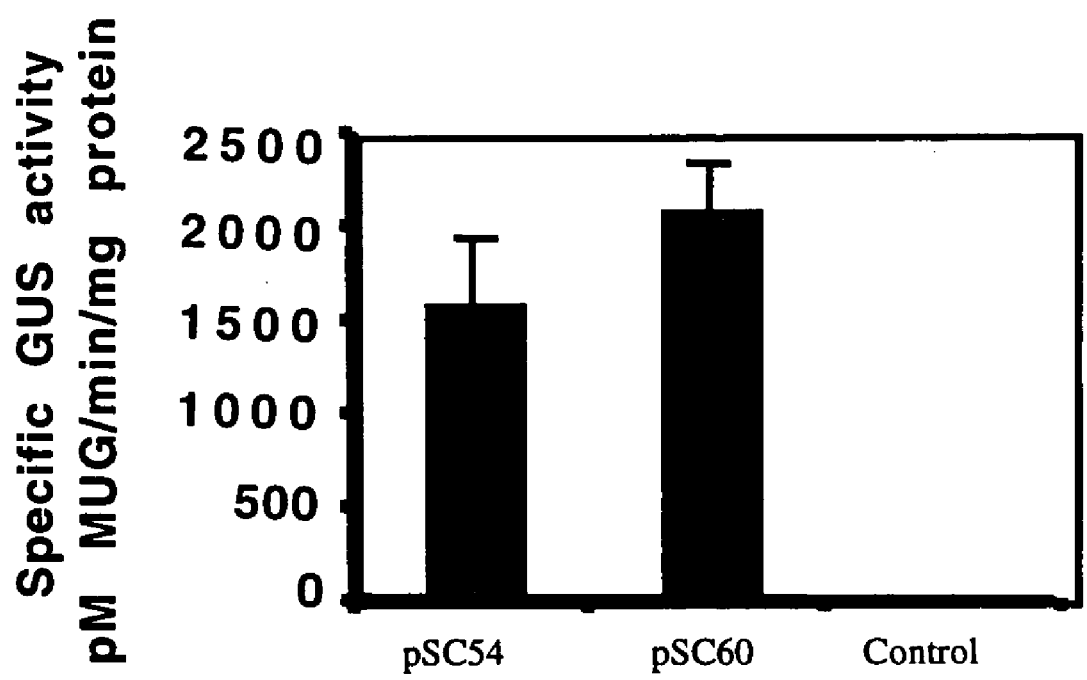
FIG. 8 shows the GUS activity of flax embryos bombarded with flax oleosin promoter-GUS-flax terminator gene constructs.

Construct pSC60: The β-glucuronidase reporter coding sequence from vector GUSN358>S (Clontech Laboratories) was placed between the promoter sequence from nucleotide 1 to 2023 and terminator sequence from 2867 to 3925 (as described in FIG. 2). This insert was cloned into pBluescript and the resulting vector is called pSC60.

pSC54, pSC60 and a promoter-less GUS construct (Control) were introduced into the flax embryos using particle bombardment using standard protocols (eg see Abenes et al. (1997) Plant Cell reports 17:1-7). FIG. 8 shows the GUS activity of flax embryos bombarded with pSC54, pSC60 and a promoterless GUS construct measured 48 hours after particle bombardment. As can be seen the flax oleosin regulatory sequences are sufficient to drive the expression of GUS in flax embryos.

Example 5

Stable Seed Specific Expression of β-glucuronidase (GUS) in Flax and *Arabidopsis* when under the Regulatory Control of Flax 2S Storage Protein Gene Promoter A GUS reporter gene construct was made by incorporating 5' and 3' regions from the DNA fragment described in FIG. 3 into promoterless-GUS pBI101 vector as follows.

A 400bp amplicon from the 5' end of the DNA fragment described in FIG. 3 was PCR amplified using the following primers (location shown in FIG. 3):

```
5' primer(1):
5'-TCCACTATGTAGGTCATA-3'       (SEQ. ID. NO.: 14)

3' primer(1):
5'-CTTTAAGGTGTGAGAGTC-3'       (SEQ. ID. NO.: 15)
```

The PCR primers also contained restriction sites for HindIII and BamHI which were used to clone the 400bp 5'UTR amplicon into the HindIII/BamHI sites of the pBI101 vector in front of the GUS reporter gene. A 736bp amplicon from the 3' untranslated region (3'UTR) of the DNA fragment described in FIG. 3 was PCR amplified using the following primers (location shown in FIG. 3):

```
5' primer (2):
5'-AGGGGTGATCGATTA-3'          (SEQ. ID. NO.: 16)

3' primer (2):
5'-GATAGAACCCACACGAGC-3'       (SEQ. ID. NO.: 17)
```

The PCR primers also contained restriction sites for SacI and EcoRI. The NOS terminator region of the pBI101 vector was cut out with SacI/EcoRI digestion and replaced with the similarly digested 736bp 3'UTR amplicon of the DNA fragment described in FIG. 3.

The GUS reporter construct was then electroporated into *Agrobacterium tumifaciens* strain AGLI and transformation of flax (Finnegan et al. (1993) Plant Mol Biol. 22(4): 625-633) and *Arabidopsis* (Valvekens et al. Proc. Natl. Acad. Sci. 85: 5536-5540) carried out according to previously described protocols.

Various tissues from flax and *Arabidopsis* plants carrying the GUS reporter construct were assayed histologically for evidence of GUS activity. In the case of flax, leaf tissue, root tissue and mid- maturity embryos dissected out of developing seeds were stained for GUS activity. For *Arabidopsis*, developing seeds were stained for GUS in situ in their siliques.

GUS staining was carried out by immersing the tissues in histochemical buffer containing 0.5 mM X-gluc, 0.5 M potassium phosphate buffer (pH 7.0), 1 mM EDTA, 0.5 M sorbital, 0.5 mM potassium ferricyanide and 0.5 mM potassium ferrocyanide. The staining reaction was carried out for 12-16 hrs at 37° C. and the reaction was stopped by adding 95% ethanol. Tissues were subsequently cleared of chlorophyll by repeated washing in 95% ethanol prior to photography. FIG. 9 shows clear evidence of strong GUS activity in developing flax embryos and *Arabidopsis* seeds, and no evidence of GUS reporter gene expression in flax roots or leaves, or in *Arabidopsis* silique walls.

Example 6

Stable Seed Specific Expression of β-glucuronidase (GUS) in Flax, *Arabidopsis* and *Brassica napus* when under the regulatory control of Flax Legumin-like Storage Protein Gene Regulatory Sequences A construct was made using standard molecular biology techniques, including restriction enzyme digestions, ligation and polymerase chain reaction (PCR). In order to obtain a DNA fragment containing approximately 2 kilobases from the 5' transcriptional initiation region of the flax legumin-like seed storage protein in a configuration suitable for ligation to a GUS coding sequence, a PCR based approach was used. This involved the use of the polymerase chain reaction to amplify the precise sequence desired for the expression analysis. To perform the necessary PCR amplification, two oligonucleotide primers were synthesized (Beckman Oligo 1000M DNA synthesizer) have the following sequences:

```
5' primer:
5'TATCTAGACTCAAGCATACG       (SEQ. ID. NO.: 18)

GACAAGGGT 3' (SJ-634)
```

The italicized bases correspond to nucleotide positions 1 to 21 in the sequence reported in FIG. 4. The additional nucleotides 5' of this sequence in the primer are not identical to the promoter sequence, but were included in order to place a XbaI site at the 5' end of the amplification product. The XbaI (5'-TCTAGA-3') (SEQ.ID.NO.:19) site is underlined.

A second (3') primer was synthesized which had the following sequence:

```
3' primer
5'GGTTATCATTGTATGAACTGA3'    (SEQ. ID. NO.: 20)

(SJ-618)
```

This primer contains the precise complement (shown in italics) to the sequence reported in FIG. 4 from bases 2343 to 2363. This primer was not designed with an additional restriction enzyme site due to the fact that a natural NcoI site (5'-CCATGG-3') (SEQ.ID.NO.:21) straddles the start codon between base pairs 2034 and 2039, thereby allowing for insertion of the storage protein promoter into the appropriate cloning vector.

These two primers were used in a PCR amplification reaction to produce a DNA fragment containing the sequence between nucleotides 1 and 2342 of the flax seed storage protein gene with a XbaI site at the 5' end and a NcoI site 302 base pairs from the 3' end. PCR amplification was performed using the enzyme Pfu (Strategene) using conditions recommended by the enzyme manufacturer and a temperature program of 94° C. (denaturation) for 1 minute, 55° C. (annealing) for 1 minute, and 72° C. (elongation) for 3.5 minutes. The template was the legumin seed storage protein genomic clone shown in FIG. 4.

The resulting amplification product was subsequently digested with XbaI and NcoI to remove the desired 2 kb promoter region. This promoter fragment was cloned into the XbaI and NcoI sites of a XbaI and NcoI digested plasmid designated pGUS1318 (Plasmid pGUSN358S (Clontech Laboratories) was cut with NcoI and EcoRI and the GUS insert was cloned into pBluescriptKS+ (Stratagene) which was adapted to contain an NcoI site in the multiple cloning site.) The resulting plasmid containing the promoter-GUS fusion was called pPGUS1318. The terminator of the legumin seed storage protein from flax was also amplified from the above mentioned genomic clone. To perform the necessary PCR amplification, oligonucleotide primers were synthesized having the following sequences:

```
5' primer:
5' GCAAGCTTAATGTGACGGTG       (SEQ. ID. NO.: 22)

AAATAATAACGG 3' (SJ620)
```

The italicized bases correspond to nucleotide positions 3780 to 3803 in the sequence reported in FIG. 4. The additional nucleotides 5' of this sequence in the primer are not identical to the promoter sequence, but were included in order to place a HindIII site at the 5' end of the amplification product. The HindIII site (5'-AAGCTT-3') (SEQ.ID.NO.:23) is underlined.

A second (3') primer was synthesized which had the following sequence:

```
3' primer
5'TAGGTACCTGGCAGGTAAA        (SEQ. ID. NO.: 24)

GACTCTGCTC3' (SJ-618)
```

This primer contains the precise complement (shown in italics) to the sequence reported in FIG. 4 from bases 4311 to 4290. The additional nucleotides 5' of this sequence in the primer are not identical to the promoter sequence, but were included in order to place a KpnI site at the 5' end of the amplification product. The KpnI site (5'-GGTACC-3') (SEQ.ID.NO.:25) is underlined.

These two primers were used in a PCR amplification reaction to produce a DNA fragment containing the sequence between nucleotides 3779 and 4311 of the flax seed storage protein gene terminator with a HindIII site at the 5' end and a KpnI site at 3' end. Amplification using PCT was as described above. The above pPGUS1318 vector that contains the amplified promoter was digested with XhoI and treated with Klenow to create a blunt end. The vector was subsequently digested with KpnI and the above amplified terminator sequence was inserted so that it was located 3' of the GUS coding sequence. The resulting vector containing the flax seed storage protein promoter, GUS and the flax seed storage protein terminator is referred to as pPGUST.

The XbaI-KpnI insert of pPGUST which contains the linin promoter-GUS coding sequence-linin terminator sequence was ligated into the XbaI-KpnI sites of pSBS3000 (This vector is a derivative from the *Agrobacterium* binary plasmid pPZP221 (Hajdukiewicz et al., 1994, Plant Molec. Biol. 25: 989-994). In pSBS3000 the plant gentamycin resistance gene of pPZP221 was replaced with parsley ubiquitin promoter-phosphinothricin acetyl transferase gene-parsley ubiquitin termination sequence to confer resistance to the herbicide glufosinate ammonium). The resulting vector is called pSBS2089. In addition the XbaI-KpnI insert of pPGUST which contains the linin promoter-GUS coding sequence-linin terminator sequence was ligated into the XbaI-KpnI sites of the *Agrobacterium* binary plasmid pCGN1559 (MacBride and Summerfield, 1990, Plant Molec. Biol. 14 269-276, confers resistance to the antibiotic kanamycin)). The resulting vector was called pSBS2083. Plasmids pSBS2089 and pSBS2083 were electroporated into *Agrobac-* terium strain EHA101. Agrobacterium strain EHA101 (pSBS2089) was used to transform flax and Arabidopsis, Agrobacterium strain EHA101 (pSBS2083) was used to transform Brassica napus. Flax transformation was performed essentially as described in Jordan and McHughen (1988) Plant cell reports 7: 281-284, except transgenic shoots were selected on 10 μM L-phosphinothricine instead of kanamycin. Arabidopsis transformation was done essentially as described in "Arabidopsis Protocols; Methods in Molecular Biology" Vol 82. Edited by Martinez-Zapater J M and Salinas J. ISBN 0-89603-391-0 pg 259-266 (1998) except the putative transgenic plants were selected on agarose plates containing 80 μM L-phosphinothricine. Brassica napus transformation was done essentially as described in Moloney et al. (1989). Plant Cell Reports. 8: 238-242.

Figure 10:
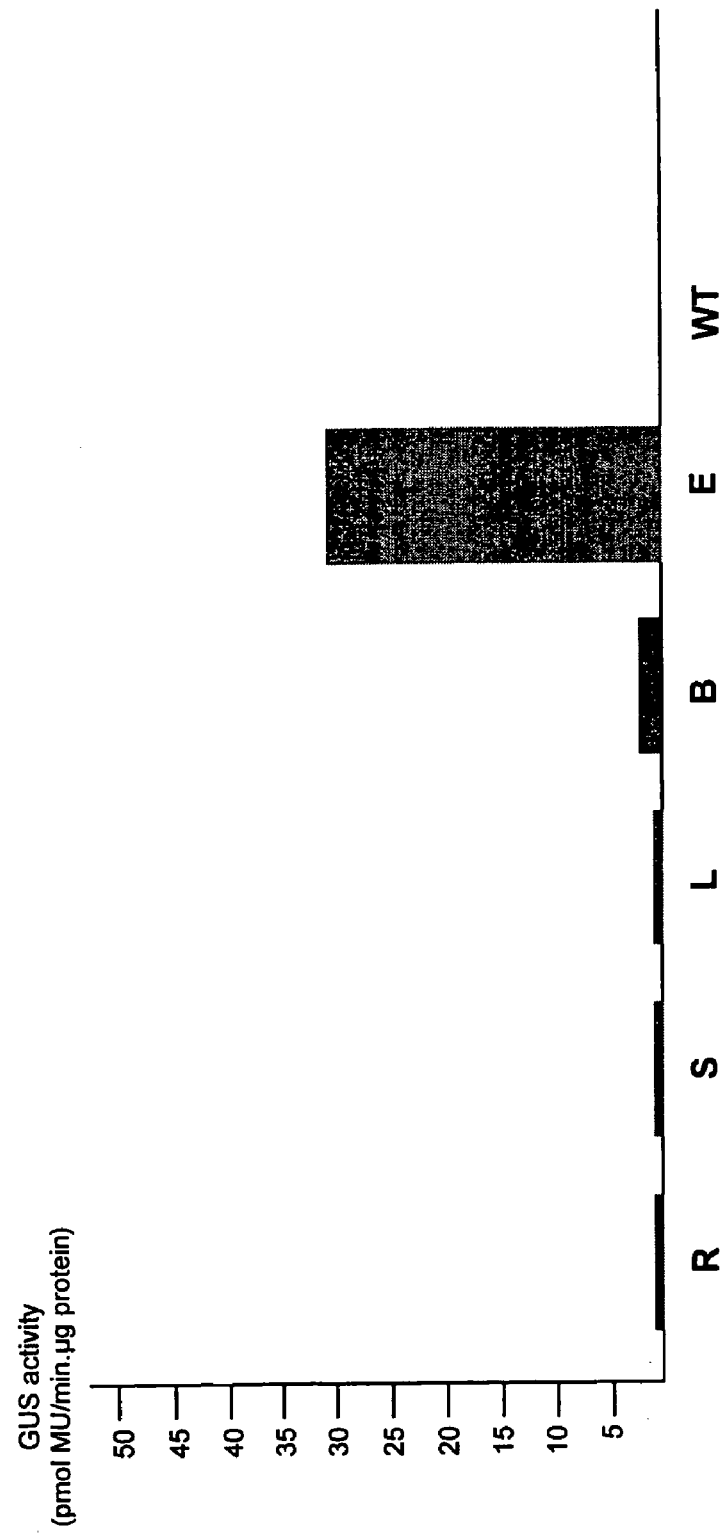
FIG. 10 shows the tissue-specific expression of GUS in transgenic flax plants transformed with a linin promoter-GUS-linin terminator gene construct.

FIG. 10 shows the tissue-specific expression of GUS in transgenic flax plants transformed with a linin-GUS gene construct (pSBS2089). GUS expression was measured in roots (R), stems (S), leaves (L), Buds (B) and embryo (E). Some expression was seen in buds, and maximal expression was achieved in embryo tissues. No detectable expression was seen in any of the untransformed (WT) tissues.

Figure 11:
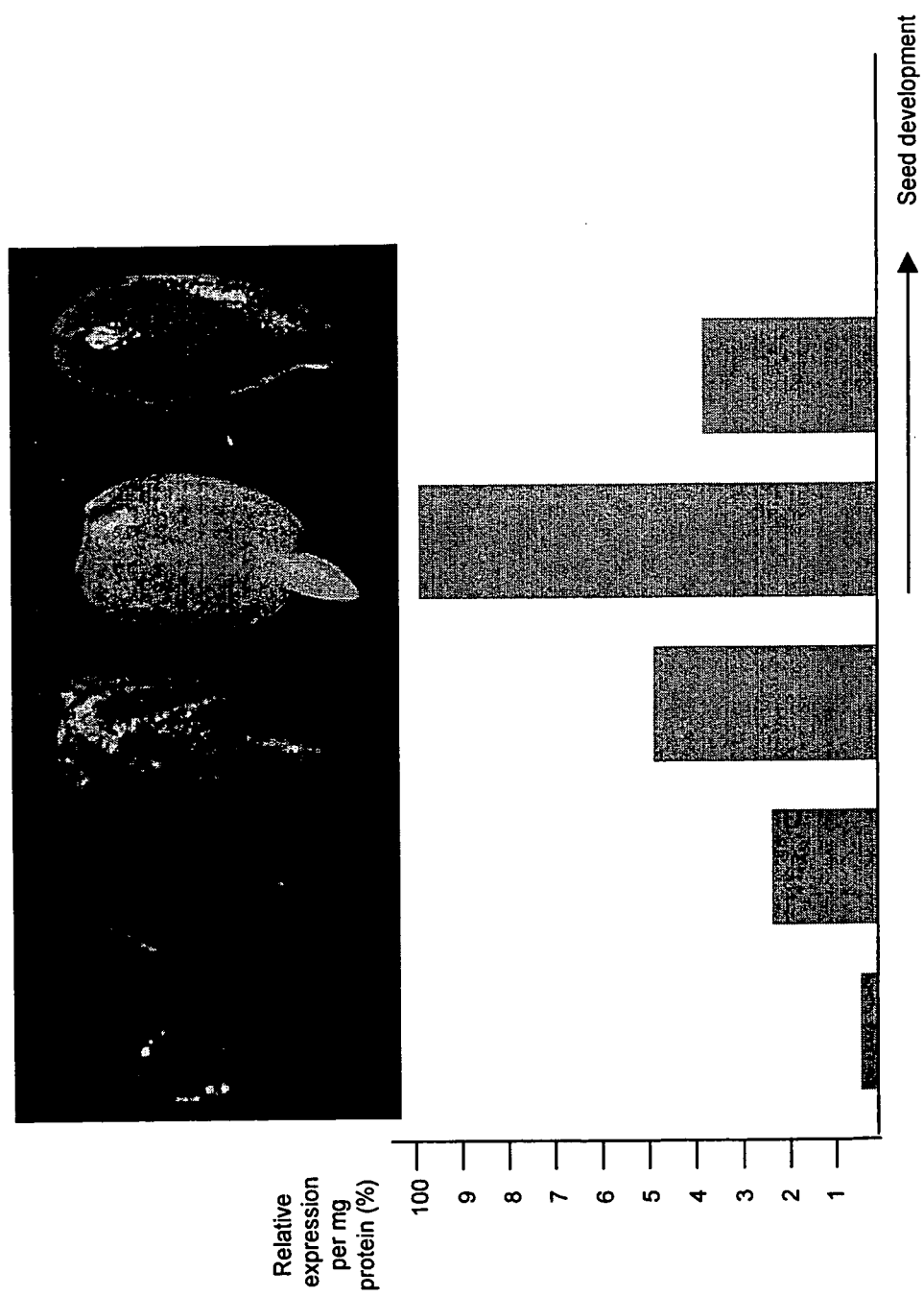
FIG. 11 shows the temporal expression of GUS in transgenic flax plants transformed a linin promoter-GUS-linin terminator gene construct.

FIG. 11 shows the temporal expression of GUS in transgenic flax plants transformed with a linin-GUS gene construct (pSBS2089). As can be seen, maximum expression is achieved in mature (pre-dessicated) flax embryos.

Figure 12:
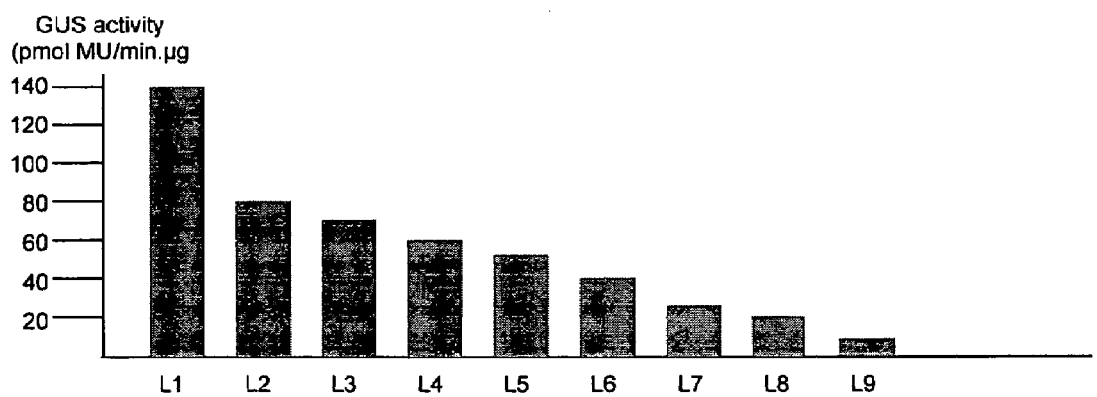
FIG. 12 shows the expression of GUS in transgenic *Brassica napus* plants (L1 to L9) transformed with a linin promoter-GUS-linin terminator gene construct.

FIG. 12 shows the absolute expression of GUS in transgenic Brassica napus plants (L1 to L9) transformed with a linin-GUS gene construct (pSBS2083). As can be seen high level expression can be achieved in Brassica napus plants. When comparing individual transgenic plants, a typical variation in expression due to position effect can also be seen.

Figure 13:
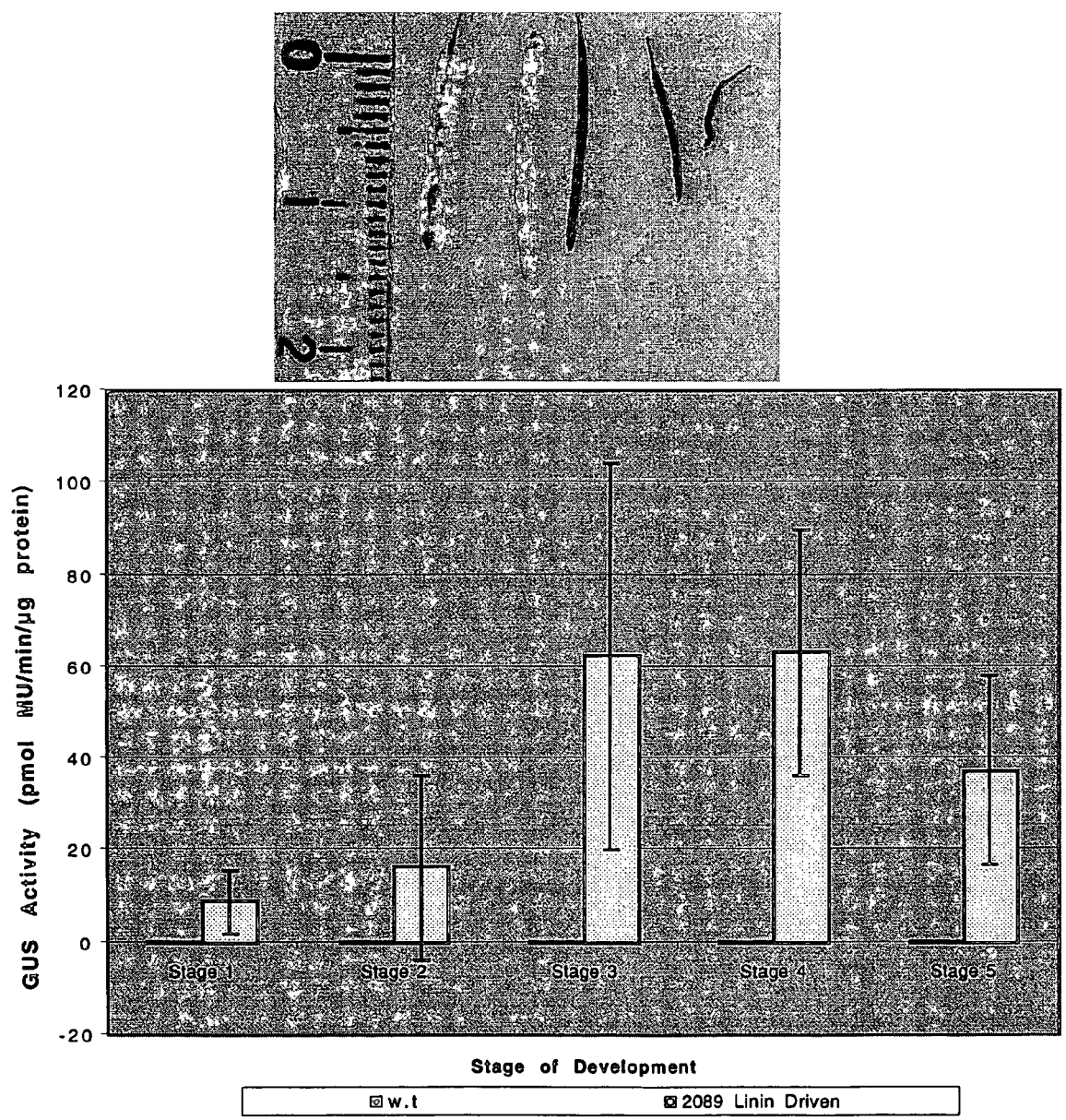
FIG. 13 shows the expression of GUS in transgenic *Arabidopsis* plants transformed with a linin promoter-GUS-linin terminator gene construct at different stages of seed development.

FIG. 13 shows expression of GUS in transgenic Arabidopsis siliques (transformed with a linin-GUS gene construct (pSBS2089)) during seed development. As can be seen high level expression can also be achieved in Arabidopsis seed tissues. Maximum expression is achieved at stage 4 (mature but not fully dessicated) of seed development. No detectable expression is observed in non-seed tissues such as leaves, stems, roots and silique walls (results not shown).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A method for the expression of a nucleic acid sequence of interest in flax seeds comprising:
   (a) preparing a chimeric nucleic acid construct comprising in the 5' to 3' direction of transcription as operably linked components:
      (1) a seed-specific promoter obtained from flax wherein said seed-preferred promoter comprises the nucleic acid sequence as shown in FIG. 3 (SEQ ID NO: 6) from nucleotides 1 to 398; and
      (2) said nucleic acid sequence of interest wherein said nucleic acid of interest is non-native to said seed-specific promoter;
   (b) introducing said chimeric nucleic acid construct into a flax plant cell; and
   (c) regenerating a mature flax plant from said flax plant cell, wherein said nucleic acid sequence of interest is expressed in the seed of said flax plant.

2. The method according to claim 1, wherein expression of said nucleic acid sequence of interest results in alteration in protein or fatty acid composition in said seed.

3. A transgenic flax seed prepared according to a method comprising:
   (a) preparing a chimeric nucleic acid construct comprising in the 5' to 3' direction of transcription as operably linked components:
      (1) a seed-preferred promoter obtained from flax wherein said seed-preferred promoter comprises the nucleic acid sequence as shown in FIG. 3 (SEQ ID NO: 6) from nucleotides 1 to 398; and
      (2) a nucleic acid sequence of interest wherein said nucleic acid of interest is non-native to said seed-preferred promoter;
   (b) introducing said chimeric nucleic acid construct into a flax plant cell;
   (c) regenerating a mature flax plant from said flax plant cell, wherein said nucleic acid sequence of interest is expressed in the seed of said flax plant; and
   (d) harvesting seed from said mature flax plant.

4. The transgenic flax seed of claim 3, wherein expression of said non-native gene of interest results in an alteration in the seed protein or fatty acid composition.

5. A transgenic flax plant capable of setting seed prepared by a method comprising:
   (a) preparing a chimeric nucleic acid construct comprising in the 5' to 3' direction of transcription as operably linked components:
      (1) a seed-preferred promoter obtained from flax wherein said seed-preferred promoter comprises the nucleic acid sequence as shown in FIG. 3 (SEQ ID NO: 6) from nucleotides 1 to 398; and
      (2) a nucleic acid sequence of interest wherein said nucleic acid of interest is non-native to said seed-preferred promoter;
   (b) introducing said chimeric nucleic acid construct into a flax plant cell; and
   (c) regenerating a mature flax plant from said flax plant cell, wherein said nucleic acid sequence of interest is expressed in the seed of said flax plant.

6. An isolated nucleic acid molecule comprising:
   (a) the nucleic acid sequence as shown in FIG. 3 (SEQ ID NO: 6) from nucleotides 1 to 398 wherein; or
   (b) a nucleic acid sequence that is complementary to the nucleic acid sequence of (a).

7. A chimeric nucleic acid molecule comprising:
   (a) a seed-preferred promoter obtained from flax which comprises:
   the nucleic acid sequence as shown in FIG. 3 (SEQ ID NO: 6) from nucleotides 1 to 398 and
   (b) a second nucleic acid sequence non-native to said flax seed-preferred promoter.

8. A method for expressing a nucleic acid sequence of interest in a plant seed comprising:
   (a) introducing the chimeric nucleic acid molecule according to claim 7 into a plant cell; and (b) regenerating a mature plant from said plant cell, wherein the second nucleic acid sequence is expressed in the seed of said plant.

9. The method of claim 8, wherein said plant cell is selected from the group consisting of soybean (*Glycine max*), rapeseed (*Brassica napus, Brassica campestris*), sunflower (*Helianthus annuus*), cotton (*Gossypium hirsutum*), corn (*Zea mays*), tobacco (*Nicotiana tobacum*), alfalafa (*Medicago sativa*), wheat (*Triticum* sp.), barley (*Hordeum vulgare*), oats (*Avena sativa* L.), sorghum (*Sorghum* bicolor), *Arabidopsis thiliana*, potato (*Solanum* sp.), flax/linseed (*Linum usitatissimum*), safflower *Carthamus tinctorius*), oil palm (*Eleais guineeis*), groundnut (*Arachis hypogaea*), Brazil nut (*Bertholletia excelsa*), coconut (*Cocus nucifera*), castor (*Ricinus communis*), coriander (*Coriandrum sativum*) squash (*Cucurbita maxima*), jojoba (*Simmondsia chinensis*) and rice (*Oryza sativa*).

10. A method of making a transgenic plant comprising:
(a) introducing the chimeric nucleic acid molecule of claim 7, into a plant cell; and
(b) regenerating a transgenic plant form said plant cell.

11. A transgenic plant prepared according to the method of claim 10.

12. A plant cell comprising the chimeric nucleic acid sequence of claim 7.

13. Plant seeds comprising the chimeric nucleic acid sequence of claim 7.

14. Transgenic plant seed obtained from the plant of claim 11.

15. A recombinant expression vector comprising the promoter of claim 6.

16. A recombinant expression vector comprising the chimeric nucleic acid molecule of claim 6.

* * * * *

UNITED STATES PATENT AND TRADEMARK OFFICE
CERTIFICATE OF CORRECTION

PATENT NO.       : 7,642,346 B2                                              Page 1 of 1
APPLICATION NO.  : 10/804219
DATED            : January 5, 2010
INVENTOR(S)      : Chaudhary et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 779 days.

Signed and Sealed this

Sixteenth Day of November, 2010

David J. Kappos
*Director of the United States Patent and Trademark Office*

SEQUENCE LISTING

```
<160> NUMBER OF SEQ ID NOS: 25

<210> SEQ ID NO 1
<211> LENGTH: 4305
<212> TYPE: DNA
<213> ORGANISM: Linum usitatissimum
<220> FEATURE:
<221> NAME/KEY: CDS
<222> LOCATION: (2024)..(2350)
<220> FEATURE:
<221> NAME/KEY: CDS
<222> LOCATION: (2727)..(2867)

<400> SEQUENCE: 1
ttcaaaaccc gattcccgag gcggccctat tgaagatatg ggggaagttc gacgagatcg      60
atgtcgggtc gagtgctatg gtgatggtgc cgtttggggg gaggatgagc gagatagcca     120
agactagcat tccgttccca cacagagttg ggaatttgta ccaaatccaa cacttgtcgt     180
attggagcga cgatagggac gcggaaaaac acatccgttg gatcagggag ttgtacgatg     240
atctcgagcc ttatgtgtcg aagaatccga ggtatgctta cgtgaactac agggatctcg     300
acatcgggat gaatggagga ggtgaagggg atgagaaggg tacttatggt gaggctaagg     360 tgtggggga gaagtacttt ggggtcaact ttgatcggtt ggttcgggtg aagacgattg     420
ttgatcccaa taatgtgttt cgaaacgagc agagcattcc ctcaattcca actcggttat     480
aaggatcaat gatcaatgag aattttcctt tccaatgtga ttacaagttc tattgggtca     540
gctttctcaa ctgctcctat tcatttagat taattcataa caactattaa tttaccagcc     600
ttttatccgg cccgttggcc gatttatttt cttaagtttt agatgaaatg aaaccgattt     660
agtttttatt gagatgagat taatcttaat ttgcttgaaa tttactcacg gttgatgtga     720
tatttggaat taactaaaat gataaatatc ggataaaaat aaaaatattt aaaataaata     780
acataaacat aagaacaata aaataaataa atttaatttt aatttatttc cttgttttct     840
```

```
ttctgtatca tacatctctt ctccttacttc ttaaaggctt ttcaattatc acttaattaa    900
atacaataga taaatcgtta attctataac attaacctat acacttgcac ggtgaacaat    960
caatatgata atataataat aatataataa ttcaattatt aatctacaat tttttaatta   1020
taaagtttat gcggtcagtt tctgcaagct ccgagctcct tgtcatcgtt agtttctgcg   1080
gtctcaaggt ataacgactc ggagcgacga gcccttcgct tccaatggac gggttgcatt   1140
tctgccgtcg ttgagctcga ttggcgtgtc atgctggagt cagagttcct acaaaaaaac   1200
cctaaactag agggtgatta gggtgaaatt agggtgttgg cctgggttcc attgtccaaa   1260
gttttagtca acttaaaaac agacttaaat tttatgcttc aaaatagttt atctgttatt   1320
atattagcgt gtaattagtc ttgacaatgg ggccggacgg gtacggattc gggaccccga   1380
tccccgccca tagtgtaatg gctcaactgc caagtcagca ttggaccgaa attattggac   1440
acgaagtact aatgtgaaaa actttacatt tgttatttc tactttaata ctatgctatt   1500
ttcaaaattt gaactttaat actatgtttt tatatagttt agtatatctt aattttatg   1560
caaattcatc taattgtatt aaactatttt cgatccgtag ctaattattt cgaaggcaag   1620
tcaaagtgtt attgtggact atgtgagcta atattgaacc tttatctctc ccaaccactc   1680
aagttaattg aaccaaactc gatcggttgg gtttcgagct atttcgagcc attgttgtta   1740
tatgcacgtg agatatcaag attgacccga acactttatt atgataatgt agaaaaagaa   1800
aacatattct aagactacat gcatgcaaag tgcaaccct gcatggaaag ctgctcaaca   1860
cgtggcatag actcccgcca cgtgtccatt ccacctcatc acctcacccc caccgttcac   1920
ctcttattat atcacaacaa tcaatcaatc ctactcctcc atactcgaac aaatccgacc   1980
aacttatacc aatattccca aacttgatta atttctcagc aat atg gat cag acg     2035
                                              Met Asp Gln Thr
                                                1
cac cag aca tac gcc gga acc acg cag aac ccg agc tat ggc ggc ggg     2083
His Gln Thr Tyr Ala Gly Thr Thr Gln Asn Pro Ser Tyr Gly Gly Gly
  5                  10                  15                  20
ggc aca atg tac cag cag cag cag ccg agg tct tac cag gcg gtg aag     2131
Gly Thr Met Tyr Gln Gln Gln Gln Pro Arg Ser Tyr Gln Ala Val Lys
              25                  30                  35
gcg gcc act gca gcc acc gcg ggt gga tcc ctc atc gtt ctg tcc ggt     2179
Ala Ala Thr Ala Ala Thr Ala Gly Gly Ser Leu Ile Val Leu Ser Gly
          40                  45                  50
ctc atc ctt acg gcc acc gtc att tca ctc atc ata gcc acc cct ctc     2227
Leu Ile Leu Thr Ala Thr Val Ile Ser Leu Ile Ile Ala Thr Pro Leu
      55                  60                  65
ctt gtc atc ttc agc cct gtt ctt gtc ccg gct ctc atc acc gtc ggg     2275
Leu Val Ile Phe Ser Pro Val Leu Val Pro Ala Leu Ile Thr Val Gly
  70                  75                  80
ctc ttg atc acc ggg ttt ctt gct tcc ggt ggg ttc gga gtc gcc gcc     2323
Leu Leu Ile Thr Gly Phe Leu Ala Ser Gly Gly Phe Gly Val Ala Ala
 85                  90                  95                 100
gtc acc gtc ttg tcc tgg atc tat agg tatgtataag ctttggactt            2370
Val Thr Val Leu Ser Trp Ile Tyr Arg
                105
tagtattgtt ataaaataca taagctgatt tatgaacatg gatctcccaa caagagttat   2430
ttaaatgcat tctcggtctg actcgatcgg ttgggttttg agctactcgg tcacaatggt   2490
cgggtcggct ctggatctgt tatactaata tttggaagcc tgaagtttca ttgttctgcc   2550
ccaacttccc actaccttt gagggtgtta agaagccata caaactaatt atgaatccct   2610
```

-continued

```
cccaacaact cagaactcga gtcagtgggt tgtgacggtt ctctataaac atttcgaaaa    2670
tctttgttca atgaacgtag aaatgaccat gcttgatgat tgtgggtctt ataagg tac   2729
                                                             Tyr
                                                             110 gtg acc ggc ggg cac ccg gcg gga ggg gat tcg ctg gac cag gct agg     2777
Val Thr Gly Gly His Pro Ala Gly Gly Asp Ser Leu Asp Gln Ala Arg
            115                 120                 125 tcg aag ctg gcc gga aag gcc agg gag gtg aag gac agg gcg tcg gag     2825
Ser Lys Leu Ala Gly Lys Ala Arg Glu Val Lys Asp Arg Ala Ser Glu
130                 135                 140 ttc gca cag cag cat gtc aca ggt ggt caa cag acc tct taa             2867
Phe Ala Gln Gln His Val Thr Gly Gly Gln Gln Thr Ser
    145                 150                 155 agagagtcct ctagttaaat tggtcttcgt ttctgtttcg tggcggcttg taaactctct    2927
tttaagtgtg ctgttttcct tttgtctcgt gtgttgtaag tgaaagtgta atcgaagttc    2987
caagttggag atgtttgtaa cgatgatgtt ttctaataat cagagatatt aaaagggttg    3047
ctaatttagt attgcgtctg atctcggacc aaactcgcaa gtaaaattgc agaggatgag    3107
ttgtacagaa caagcgtgca ttgttctgga agttcatctc cttggagccg accttgttgc    3167
ttgcagtttc gccaagtcca ctagacaatg ttacgagtta agcctctgtc aaacagatcg    3227
ctctagcgtc ccagaaaaca ccagattttt cgaaaaccat cggggatcaa ttttcgattc    3287
aattccgatc ttggaagtac ttgaacagaa gcatgatgct aaaagataat agaaaatcga    3347
agcctagaaa agttgtacag aaagcaacaa gtcaaaaata tagatcaact tcaaaggttc    3407
aaattacatc ttacagaccc caaaaaatga cagttaacag aagtcgacta aacagaaacc    3467
agccagcttc acctggaatg aaggagcttt gatcaatcca tcctagcttc attcccctt     3527 gaaattgcag acagagctct catcctgcta aagctggtgg cttattctta accctgcaat    3587
caataagcat gaactaacat tggacacctt catcggcgga ttgctcgaaa atcagtgagc    3647
gagggattta cctgtgtgtg tagtaacctc tctccttgta cataaaatct ggaaattccg    3707
gcatcaacta ctgccacctt tctgcttaag gtgattttat caccaaggct gagcgtgatt    3767
ccttgcgtct tgctccgaat cctgatgtat ccactgagct ttccatctcc ttccttctcc    3827
aggcttatgt tcaccaatgc gtcctcgccg aacacactct tggcgtacaa gttcgcagcc    3887
aggaatccac actctccatc aagtgcagac ctgcaaaccc caaataagaa cacaaactcc    3947
aaagtcaacg atcaattctc cgccttttat gaagaaaagg aaacttctgg gtacttacgg    4007
tgccgtcaga cacttcatat ttgtagactt gatgatatgt tccaggaatt ccttctcgtt    4067
ctgaattgtt gtgttaacag caacctgaca gacagaaaga tatcgcaaat ttaagatact    4127
gggatgacta ggcacagaga aatgaaatct aattctagaa gtaaaacctt attttcccat    4187
tcaaattctg cccacatagt ccggaacgca gcatccgagc aagaagcagg agagatgtaa    4247
tccatgatat cgatgtggat atcgttgagg acgacaactg aacgttccat cacattgg     4305
```

<210> SEQ ID NO 2
<211> LENGTH: 109
<212> TYPE: PRT
<213> ORGANISM: Linum usitatissimum

<400> SEQUENCE: 2

```
Met Asp Gln Thr His Gln Thr Tyr Ala Gly Thr Thr Gln Asn Pro Ser
1               5                   10                  15

Tyr Gly Gly Gly Gly Thr Met Tyr Gln Gln Gln Pro Arg Ser Tyr
            20                  25                  30
```

```
Gln Ala Val Lys Ala Ala Thr Ala Ala Thr Ala Gly Gly Ser Leu Ile
            35                  40                  45

Val Leu Ser Gly Leu Ile Leu Thr Ala Thr Val Ile Ser Leu Ile Ile
 50                  55                  60

Ala Thr Pro Leu Leu Val Ile Phe Ser Pro Val Leu Val Pro Ala Leu
 65                  70                  75                  80

Ile Thr Val Gly Leu Leu Ile Thr Gly Phe Leu Ala Ser Gly Gly Phe
                 85                  90                  95

Gly Val Ala Ala Val Thr Val Leu Ser Trp Ile Tyr Arg
            100                 105

<210> SEQ ID NO 3
<211> LENGTH: 46
<212> TYPE: PRT
<213> ORGANISM: Linum usitatissimum

<400> SEQUENCE: 3

Tyr Val Thr Gly Gly His Pro Ala Gly Gly Asp Ser Leu Asp Gln Ala
 1               5                  10                  15

Arg Ser Lys Leu Ala Gly Lys Ala Arg Glu Val Lys Asp Arg Ala Ser
            20                  25                  30

Glu Phe Ala Gln Gln His Val Thr Gly Gly Gln Gln Thr Ser
        35                  40                  45

<210> SEQ ID NO 4
<211> LENGTH: 3501
<212> TYPE: DNA
<213> ORGANISM: Linum usitatissimum
<220> FEATURE:
<221> NAME/KEY: CDS
<222> LOCATION: (1853)..(2395)

<400> SEQUENCE: 4
```

| | |
|---|---:|
| tctagacatt tgacataaac cgaattcaaa gaacacaaca ttgactaaca ccaaaaagaa | 60 |
| atagagtagt gaaatttgga agattaaaaa atagaaacaa actgattctt agaaagaaga | 120 |
| gatgattagg tgcttttcagt tcggtctgtc aggaaatcga gatgttcact tatttacatt | 180 |
| gtcgattcat ctcccaattg tcctggttcc tttactgtcc gacgcttttt tgaatcccag | 240 |
| ttaattccca tcaagtcttc cttcagctgc gtagcactgc tagctccaac atggagcgtg | 300 |
| gagtctactc gttcatgggg catcgcaaag gtttgccttc atgttctgct accagccagc | 360 |
| gcccaccgcc tcttggttgt gtggacaatt gcggtgaagc gcgcaagttg acatcccata | 420 |
| gtctcgacac ttcaccatat ggatgtttaa acgtatatc acgagtgcga tctacatgtc | 480 |
| ccatcacacc acatataaag caatagtttg ggagcttttc atatttgaaa cgggcattga | 540 |
| cgacttgccc tctcgataat ttaatctttt tttctcttca gctgattgtg tgcatccatt | 600 |
| cgggctcaga agcacatcaa aggatctct ccatcgtagt attgggtcgt gtcgtatgat | 660 |
| acgaagcagt cgatgaagtt tcctaatgtg cgagctacag gctccgcaaa gaacccgcga | 720 |
| ggtagatcgt atgctagtac ccaaaaatca gtttgtcgta gcggaatcaa cactagagac | 780 |
| tcaccctaat gcatctcatg tgtgatgaac agtttatcat ttgtgagtct agggtcatt | 840 |
| gtcgatgacc caatgcacat tgagcttatg atagaatttg aataggaagc gttttccacc | 900 |
| cagatcacga atagctaccc cttttttcggg cgccaaattt ccggcatcct atcttccacc | 960 |
| acaacttaaa gatgcgatcg gtaaggaact caccgaccac acatcgaa taatcttcgg | 1020 |
| tgaccggttc ctgttgatca agtccctcaa tttcctcaac ctagtcttca atcgccgcta | 1080 |

-continued

```
gcgttatccc ccgcatatgg actttcatag cgcggagcgt agccggagac gacgagcaag   1140
aaggatgagc ggcggcagat tgcggctaaa gaaacgagct tcctgccttg ctctatggag   1200
gcagatttct gagttgatgg tgatggattt gtgatgtgga cacttttaat ttaagttgat   1260
tttttagcac ttcattcacg taattaaata aataatttcc agtattttat atttatttcc   1320
ttacgttatc taattttttg aaagattaaa actttgatat aggcaagatc atgacacgtc   1380
gaagttaagt gaatgagact cctaacaagg taataacaaa gcagttcata aaccgaatga   1440
ccttgatctt tactaagctt gagatcattg aacatatat taaatacgtt aatgaaagat   1500
aagaacttta atataaaaat cattcaaaac gagaaactga taacaaaaac aaagcaaacg   1560
gccaacaaaa taatagacgg tggaaggatg atgcagagcc atccacccct ttttcccagt   1620
ttccttactg cttacttctc tatgcatatc acaagacgcc cttgaaactt gttagtcatg   1680
cagagccctt actcgccagg tcaccgcacc acgtgttact ctatcacttc tcctcccttt   1740
cctttaaaga accaccacgc cacctccctc tcacaaacac tcataaaaaa accacctctt   1800
gcatttctcc caagttcaaa ttagttcaca gctaagcaag aactcaacaa ca atg gcg   1858
                                                            Met Ala
                                                              1 gat cgt aca aca cag cca cac caa gtc cag gtc cac acc cag cac cac   1906
Asp Arg Thr Thr Gln Pro His Gln Val Gln Val His Thr Gln His His
        5                  10                  15 tat ccc acc ggc ggg gct ttc ggc cgt tat gaa ggt gga ctc aaa ggc   1954
Tyr Pro Thr Gly Gly Ala Phe Gly Arg Tyr Glu Gly Gly Leu Lys Gly
    20                  25                  30 ggt cca cat cac cag caa gga tca ggc agc ggc cca tca gct tcc aag   2002
Gly Pro His His Gln Gln Gly Ser Gly Ser Gly Pro Ser Ala Ser Lys
35                  40                  45                  50 gtg tta gca gtc atg acc gcg ctc ccc atc ggc ggg acc ctc ctt gcc   2050
Val Leu Ala Val Met Thr Ala Leu Pro Ile Gly Gly Thr Leu Leu Ala
                55                  60                  65 ttg gcc ggg ata acc ttg gct ggg acg atg atc ggg ctg gcg atc acc   2098
Leu Ala Gly Ile Thr Leu Ala Gly Thr Met Ile Gly Leu Ala Ile Thr
            70                  75                  80 acc ccg att ttt gtc atc tgc agc cct gtt cta gtc ccg gcc gct ctg   2146
Thr Pro Ile Phe Val Ile Cys Ser Pro Val Leu Val Pro Ala Ala Leu
        85                  90                  95 ctc atc ggg ttt gcc gtg agc gcg ttt ctg gcc tcg ggg atg gcc ggg   2194
Leu Ile Gly Phe Ala Val Ser Ala Phe Leu Ala Ser Gly Met Ala Gly
    100                 105                 110 ctg aca ggg ctg acc tcg ctg tcg tgg ttt gcg agg tat ctg cag cag   2242
Leu Thr Gly Leu Thr Ser Leu Ser Trp Phe Ala Arg Tyr Leu Gln Gln
115                 120                 125                 130 gct ggg cag gga gtt gga gtg ggg gtg ccg gat agt ttc gag cag gcg   2290
Ala Gly Gln Gly Val Gly Val Gly Val Pro Asp Ser Phe Glu Gln Ala
                135                 140                 145 aag agg cgc atg cag gat gct gct ggg tat atg ggg cag aag acc aag   2338
Lys Arg Arg Met Gln Asp Ala Ala Gly Tyr Met Gly Gln Lys Thr Lys
            150                 155                 160 gaa gtt ggg cag gag atc cag agg aag tct cag gat gtg aaa gca tca   2386
Glu Val Gly Gln Glu Ile Gln Arg Lys Ser Gln Asp Val Lys Ala Ser
        165                 170                 175 gac aaa taa ggtgataata aggggttttg ggttcgtgtg taaactggta             2435
Asp Lys
    180 aaatggaaat tctgggtttt actgtacttt tgcatgtagt ggaatgaatg agttcttgtt   2495
```

-continued

```
ctcttttgtc ttttaatcat aaagtaagaa gcagcatttc atgttctggt tgaatattgt    2555
caagaattcg caacaaattt agctaaacca gttcaatctt accggttaga cgacttccca    2615
gtaagaaaca ttccaggtcc atcccggtat aagagtctgg acttctgaaa cctttagacc    2675
ttggatttgg aaaaaagatg aaaccttag aataaattac aacgatggca gattgtacaa    2735
aactggagtc gagatcatgt aaattagccc ataactaaga accggcgatg acaacaatta    2795
ctaggaatat ggttgttggg ctggtcggcg gctagcggtg atgatttgga gaatcgggg    2855 atccagaatg tgagaaccga atcatcgacg aacattaccc ggcgaggagc ccatttcaag    2915
caactttgga actcctatat ggctgttcca gcaggccacc tgctcaagaa agaaagaagc    2975
catgtcagaa atccttacga aatctaactg gatgctgata tgaatccgcc aggtgtgcgg    3035
agttctttac aggcaggatc tataaagaag aaacatgttt tgtattggca ttgttgatgt    3095
tccaagcacg cagcgatcta tctccggatc ctaacaacaa aaatacggat tctgtaagaa    3155
acaagcgcag aaaacttctg caacgaaacc actcgtatat ttggttctga gttggagaaa    3215
gatgaccata ctactgtatt tggttgaact tggattggaa ccgaaatttt gagttgaaaa    3275
gcgagtgatc gtatataaat ttcagattca gattaggata tcctatgaga gaaggtagag    3335
ttacctgata ctacatactg cccatcaggg gtaaaagttg cctcgatggt tgtgtttgga    3395
gatggttcca ggctaaatcc acaacgctga acaaattaaa agatgaatgg atcaatcttc    3455 aaccccttact tctgcattta tgaggattgg ctcaaggctc tctaga                 3501
```

<210> SEQ ID NO 5
<211> LENGTH: 180
<212> TYPE: PRT
<213> ORGANISM: Linum usitatissimum

<400> SEQUENCE: 5

```
Met Ala Asp Arg Thr Thr Gln Pro His Gln Val Gln Val His Thr Gln
 1               5                  10                  15

His His Tyr Pro Thr Gly Gly Ala Phe Gly Arg Tyr Glu Gly Gly Leu
            20                  25                  30

Lys Gly Gly Pro His His Gln Gln Gly Ser Gly Ser Gly Pro Ser Ala
        35                  40                  45

Ser Lys Val Leu Ala Val Met Thr Ala Leu Pro Ile Gly Gly Thr Leu
    50                  55                  60

Leu Ala Leu Ala Gly Ile Thr Leu Ala Gly Thr Met Ile Gly Leu Ala
65                  70                  75                  80

Ile Thr Thr Pro Ile Phe Val Ile Cys Ser Pro Val Leu Val Pro Ala
                85                  90                  95

Ala Leu Leu Ile Gly Phe Ala Val Ser Ala Phe Leu Ala Ser Gly Met
            100                 105                 110

Ala Gly Leu Thr Gly Leu Thr Ser Leu Ser Trp Phe Ala Arg Tyr Leu
        115                 120                 125

Gln Gln Ala Gly Gln Gly Val Gly Val Gly Val Pro Asp Ser Phe Glu
    130                 135                 140

Gln Ala Lys Arg Arg Met Gln Asp Ala Ala Gly Tyr Met Gly Gln Lys
145                 150                 155                 160

Thr Lys Glu Val Gly Gln Glu Ile Gln Arg Lys Ser Gln Asp Val Lys
                165                 170                 175

Ala Ser Asp Lys
            180
```

<210> SEQ ID NO 6
<211> LENGTH: 1676
<212> TYPE: DNA
<213> ORGANISM: Linum usitatissimum
<220> FEATURE:
<221> NAME/KEY: CDS
<222> LOCATION: (418)..(942)

<400> SEQUENCE: 6

```
tccactatgt aggtcatatc catcatttta attttgggc accattcaat tccatcttgc     60
ctttagggat gtgaatatga acggccaagg taagagaata aaataatcc aaattaaagc    120 aagagaggcc aagtaagata atccaaatgt acacttgtca tcgccgaaat tagtaaaata    180
cgcggcatat tgtattccca cacattatta aaataccgta tatgtattgg ctgcatttgc    240
atgaataata ctacgtgtaa gcccaaaaga acccacgtgt agcccatgca aagttaacac    300
tcacgacccc attcctcagt ctccactata aaacccacc atccccaatc ttaccaaacc    360
caccacacga ctcacaactc gactctcaca ccttaaagaa ccaatcacca ccaaaaa      417
```

| | | | | | | | | | | | | | | | | |
|---|---|---|---|---|---|---|---|---|---|---|---|---|---|---|---|---|
| atg | gca | aag | ctg | atg | agc | cta | gca | gcc | gta | gca | acg | cag | ttc | ctc | ttc | 465 |
| Met | Ala | Lys | Leu | Met | Ser | Leu | Ala | Ala | Val | Ala | Thr | Gln | Phe | Leu | Phe | |
| 1 | | | | 5 | | | | | 10 | | | | | 15 | | |

| ctg | atc | gtg | gtg | gac | gca | tcc | gtc | cga | acc | aca | gtg | att | atc | gac | gag | 513 |
|---|---|---|---|---|---|---|---|---|---|---|---|---|---|---|---|---|
| Leu | Ile | Val | Val | Asp | Ala | Ser | Val | Arg | Thr | Thr | Val | Ile | Ile | Asp | Glu | |
| | | | 20 | | | | | 25 | | | | | 30 | | | |

| gag | acc | aac | caa | ggc | cgc | ggt | gga | ggc | aag | gtg | gca | ggg | aca | gca | gca | 561 |
|---|---|---|---|---|---|---|---|---|---|---|---|---|---|---|---|---|
| Glu | Thr | Asn | Gln | Gly | Arg | Gly | Gly | Gly | Lys | Val | Ala | Gly | Thr | Ala | Ala | |
| | | 35 | | | | | 40 | | | | | 45 | | | | |

| gtc | tgc | gag | cag | cag | atc | cag | cag | cga | gac | ttc | ctg | agg | agc | tgc | cag | 609 |
|---|---|---|---|---|---|---|---|---|---|---|---|---|---|---|---|---|
| Val | Cys | Glu | Gln | Gln | Ile | Gln | Gln | Arg | Asp | Phe | Leu | Arg | Ser | Cys | Gln | |
| 50 | | | | | 55 | | | | | 60 | | | | | | |

| cag | ttc | atg | tgg | gag | aaa | gtc | cag | agg | ggc | ggc | cac | agc | cac | tat | tac | 657 |
|---|---|---|---|---|---|---|---|---|---|---|---|---|---|---|---|---|
| Gln | Phe | Met | Trp | Glu | Lys | Val | Gln | Arg | Gly | Gly | His | Ser | His | Tyr | Tyr | |
| 65 | | | | | 70 | | | | | 75 | | | | | 80 | |

| aac | cag | ggc | cgt | gga | gga | ggc | gaa | cag | agc | cag | tac | ttc | gaa | cag | ctg | 705 |
|---|---|---|---|---|---|---|---|---|---|---|---|---|---|---|---|---|
| Asn | Gln | Gly | Arg | Gly | Gly | Gly | Glu | Gln | Ser | Gln | Tyr | Phe | Glu | Gln | Leu | |
| | | | 85 | | | | | 90 | | | | | 95 | | | |

| ttt | gtg | acg | acc | tta | agc | aat | tgc | gca | ccg | cgg | tgc | acc | atg | cca | ggg | 753 |
|---|---|---|---|---|---|---|---|---|---|---|---|---|---|---|---|---|
| Phe | Val | Thr | Thr | Leu | Ser | Asn | Cys | Ala | Pro | Arg | Cys | Thr | Met | Pro | Gly | |
| | | | 100 | | | | | 105 | | | | | 110 | | | |

| gac | ttg | aag | cgt | gcc | atc | ggc | caa | atg | agg | cag | gaa | atc | cag | cag | cag | 801 |
|---|---|---|---|---|---|---|---|---|---|---|---|---|---|---|---|---|
| Asp | Leu | Lys | Arg | Ala | Ile | Gly | Gln | Met | Arg | Gln | Glu | Ile | Gln | Gln | Gln | |
| | | 115 | | | | | 120 | | | | | 125 | | | | |

| gga | cag | cag | cag | gga | cag | cag | cag | gaa | gtt | cag | agg | tgg | atc | cag | caa | 849 |
|---|---|---|---|---|---|---|---|---|---|---|---|---|---|---|---|---|
| Gly | Gln | Gln | Gln | Gly | Gln | Gln | Gln | Glu | Val | Gln | Arg | Trp | Ile | Gln | Gln | |
| 130 | | | | | 135 | | | | | 140 | | | | | | |

| gct | aaa | caa | atc | gct | aag | gac | ctc | ccc | gga | cag | tgc | cgc | acc | cag | cct | 897 |
|---|---|---|---|---|---|---|---|---|---|---|---|---|---|---|---|---|
| Ala | Lys | Gln | Ile | Ala | Lys | Asp | Leu | Pro | Gly | Gln | Cys | Arg | Thr | Gln | Pro | |
| 145 | | | | | 150 | | | | | 155 | | | | | 160 | |

| agc | caa | tgc | cag | ttc | cag | ggc | cag | cag | caa | tct | gca | tgg | ttt | tga | | 942 |
|---|---|---|---|---|---|---|---|---|---|---|---|---|---|---|---|---|
| Ser | Gln | Cys | Gln | Phe | Gln | Gly | Gln | Gln | Gln | Ser | Ala | Trp | Phe | | | |
| | | | 165 | | | | | 170 | | | | | 175 | | | |

```
agggtgatc gattatgaga tcgtacaaag acactgctag gtgttaagga tggataataa   1002
taataataat gagatgaatg tgttttaagt tagtgtaaca gctgtaataa agagagagag   1062
agagagagag agagagagag agagagagag agagagagag aggctgatga aatgttatgt   1122
atgtttcttg gttttaaaa taaatgaaag cacatgctcg tgtggttcta tcgaattatt   1182
cggcggttcc tgtgggaaaa agtccagaag ggcggccgca gctactacta caaccaaggc   1242
cgtggaggag ggcaacagag ccagcacttc gatagctgct gcgatgatct taagcaattg   1302
```

-continued

```
aggagcgagt gcacatgcag gggactggag cgtgcaatcg ccagatgag gcaggacatc    1362 cagcagcagg gacagcagca ggaagttgag aggtggtccc atcaatctaa acaagtcgct    1422
agggaccttc cgggacagtg cggcacccag cctagccgat gccagctcca ggggcagcag    1482
cagtctgcat ggttttgaag tggtgatcga tgagatcgta taaagacact gctaggtgtt    1542
aaggatggga ataagatg tgttttaagt cattaaccgt aataaaaaga gagagaggct       1602
gatggaatgt tatgtatgta tgtttcttgg ttttaaaat taaatggaaa gcacatgctc     1662
gtgtgggttc tatc                                                       1676
```

<210> SEQ ID NO 7
<211> LENGTH: 174
<212> TYPE: PRT
<213> ORGANISM: Linum usitatissimum

<400> SEQUENCE: 7

```
Met Ala Lys Leu Met Ser Leu Ala Ala Val Ala Thr Gln Phe Leu Phe
 1               5                  10                  15

Leu Ile Val Val Asp Ala Ser Val Arg Thr Thr Val Ile Ile Asp Glu
             20                  25                  30

Glu Thr Asn Gln Gly Arg Gly Gly Lys Val Ala Gly Thr Ala Ala
         35                  40                  45

Val Cys Glu Gln Gln Ile Gln Gln Arg Asp Phe Leu Arg Ser Cys Gln
     50                  55                  60

Gln Phe Met Trp Glu Lys Val Gln Arg Gly Gly His Ser His Tyr Tyr
 65                  70                  75                  80

Asn Gln Gly Arg Gly Gly Gly Glu Gln Ser Gln Tyr Phe Glu Gln Leu
                 85                  90                  95

Phe Val Thr Thr Leu Ser Asn Cys Ala Pro Arg Cys Thr Met Pro Gly
            100                 105                 110

Asp Leu Lys Arg Ala Ile Gly Gln Met Arg Gln Glu Ile Gln Gln Gln
        115                 120                 125

Gly Gln Gln Gln Gly Gln Gln Gln Glu Val Gln Arg Trp Ile Gln Gln
    130                 135                 140

Ala Lys Gln Ile Ala Lys Asp Leu Pro Gly Gln Cys Arg Thr Gln Pro
145                 150                 155                 160

Ser Gln Cys Gln Phe Gln Gly Gln Gln Ser Ala Trp Phe
                165                 170
```

<210> SEQ ID NO 8
<211> LENGTH: 4999
<212> TYPE: DNA
<213> ORGANISM: Linum usitatissimum
<220> FEATURE:
<221> NAME/KEY: CDS
<222> LOCATION: (2036)..(2329)
<220> FEATURE:
<221> NAME/KEY: CDS
<222> LOCATION: (2428)..(2682)
<220> FEATURE:
<221> NAME/KEY: CDS
<222> LOCATION: (2771)..(3265)
<220> FEATURE:
<221> NAME/KEY: CDS
<222> LOCATION: (3354)..(3779)
<220> FEATURE:
<221> NAME/KEY: modified_base
<222> LOCATION: (4396)..(4396)
<223> OTHER INFORMATION: a, c, g, or t
<220> FEATURE:
<221> NAME/KEY: modified_base

```
<222> LOCATION: (4407)..(4407)
<223> OTHER INFORMATION: a, c, g, or t
<220> FEATURE:
<221> NAME/KEY: modified_base
<222> LOCATION: (4415)..(4415)
<223> OTHER INFORMATION: a, c, g, or t
<220> FEATURE:
<221> NAME/KEY: modified_base
<222> LOCATION: (4423)..(4423)
<223> OTHER INFORMATION: a, c, g, or t
<220> FEATURE:
<221> NAME/KEY: modified_base
<222> LOCATION: (4445)..(4445)
<223> OTHER INFORMATION: a, c, g, or t
<220> FEATURE:
<221> NAME/KEY: modified_base
<222> LOCATION: (4475)..(4475)
<223> OTHER INFORMATION: a, c, g, or t
<220> FEATURE:
<221> NAME/KEY: modified_base
<222> LOCATION: (4497)..(4497)
<223> OTHER INFORMATION: a, c, g, or t
<220> FEATURE:
<221> NAME/KEY: modified_base
<222> LOCATION: (4515)..(4515)
<223> OTHER INFORMATION: a, c, g, or t
<220> FEATURE:
<221> NAME/KEY: modified_base
<222> LOCATION: (4545)..(4545)
<223> OTHER INFORMATION: a, c, g, or t
<220> FEATURE:
<221> NAME/KEY: modified_base
<222> LOCATION: (4548)..(4548)
<223> OTHER INFORMATION: a, c, g, or t
<220> FEATURE:
<221> NAME/KEY: modified_base
<222> LOCATION: (4550)..(4550)
<223> OTHER INFORMATION: a, c, g, or t
<220> FEATURE:
<221> NAME/KEY: modified_base
<222> LOCATION: (4552)..(4552)
<223> OTHER INFORMATION: a, c, g, or t
<220> FEATURE:
<221> NAME/KEY: modified_base
<222> LOCATION: (4556)..(4556)
<223> OTHER INFORMATION: a, c, g, or t
<220> FEATURE:
<221> NAME/KEY: modified_base
<222> LOCATION: (4567)..(4567)
<223> OTHER INFORMATION: a, c, g, or t
<220> FEATURE:
<221> NAME/KEY: modified_base
<222> LOCATION: (4580)..(4580)
<223> OTHER INFORMATION: a, c, g, or t
<220> FEATURE:
<221> NAME/KEY: modified_base
<222> LOCATION: (4587)..(4587)
<223> OTHER INFORMATION: a, c, g, or t
<220> FEATURE:
<221> NAME/KEY: modified_base
<222> LOCATION: (4591)..(4591)
<223> OTHER INFORMATION: a, c, g, or t
<220> FEATURE:
<221> NAME/KEY: modified_base
<222> LOCATION: (4593)..(4594)
<223> OTHER INFORMATION: a, c, g, or t
<220> FEATURE:
<221> NAME/KEY: modified_base
<222> LOCATION: (4605)..(4605)
<223> OTHER INFORMATION: a, c, g, or t
<220> FEATURE:
<221> NAME/KEY: modified_base
<222> LOCATION: (4613)..(4613)
<223> OTHER INFORMATION: a, c, g, or t
<220> FEATURE:
<221> NAME/KEY: modified_base
<222> LOCATION: (4616)..(4616)
<223> OTHER INFORMATION: a, c, g, or t
<220> FEATURE:
```

```
<221> NAME/KEY: modified_base
<222> LOCATION: (4620)..(4620)
<223> OTHER INFORMATION: a, c, g, or t
<220> FEATURE:
<221> NAME/KEY: modified_base
<222> LOCATION: (4622)..(4622)
<223> OTHER INFORMATION: a, c, g, or t
<220> FEATURE:
<221> NAME/KEY: modified_base
<222> LOCATION: (4626)..(4626)
<223> OTHER INFORMATION: a, c, g, or t
<220> FEATURE:
<221> NAME/KEY: modified_base
<222> LOCATION: (4635)..(4636)
<223> OTHER INFORMATION: a, c, g, or t
<220> FEATURE:
<221> NAME/KEY: modified_base
<222> LOCATION: (4657)..(4657)
<223> OTHER INFORMATION: a, c, g, or t
<220> FEATURE:
<221> NAME/KEY: modified_base
<222> LOCATION: (4659)..(4659)
<223> OTHER INFORMATION: a, c, g, or t
<220> FEATURE:
<221> NAME/KEY: modified_base
<222> LOCATION: (4664)..(4664)
<223> OTHER INFORMATION: a, c, g, or t
<220> FEATURE:
<221> NAME/KEY: modified_base
<222> LOCATION: (4668)..(4668)
<223> OTHER INFORMATION: a, c, g, or t
<220> FEATURE:
<221> NAME/KEY: modified_base
<222> LOCATION: (4677)..(4677)
<223> OTHER INFORMATION: a, c, g, or t
<220> FEATURE:
<221> NAME/KEY: modified_base
<222> LOCATION: (4685)..(4685)
<223> OTHER INFORMATION: a, c, g, or t
<220> FEATURE:
<221> NAME/KEY: modified_base
<222> LOCATION: (4695)..(4696)
<223> OTHER INFORMATION: a, c, g, or t
<220> FEATURE:
<221> NAME/KEY: modified_base
<222> LOCATION: (4705)..(4705)
<223> OTHER INFORMATION: a, c, g, or t
<220> FEATURE:
<221> NAME/KEY: modified_base
<222> LOCATION: (4708)..(4708)
<223> OTHER INFORMATION: a, c, g, or t
<220> FEATURE:
<221> NAME/KEY: modified_base
<222> LOCATION: (4711)..(4713)
<223> OTHER INFORMATION: a, c, g, or t
<220> FEATURE:
<221> NAME/KEY: modified_base
<222> LOCATION: (4715)..(4716)
<223> OTHER INFORMATION: a, c, g, or t
<220> FEATURE:
<221> NAME/KEY: modified_base
<222> LOCATION: (4731)..(4732)
<223> OTHER INFORMATION: a, c, g, or t
<220> FEATURE:
<221> NAME/KEY: modified_base
<222> LOCATION: (4738)..(4738)
<223> OTHER INFORMATION: a, c, g, or t
<220> FEATURE:
<221> NAME/KEY: modified_base
<222> LOCATION: (4740)..(4741)
<223> OTHER INFORMATION: a, c, g, or t
<220> FEATURE:
<221> NAME/KEY: modified_base
<222> LOCATION: (4743)..(4743)
<223> OTHER INFORMATION: a, c, g, or t
<220> FEATURE:
<221> NAME/KEY: modified_base
<222> LOCATION: (4746)..(4746)
<223> OTHER INFORMATION: a, c, g, or t
```

```
<220> FEATURE:
<221> NAME/KEY: modified_base
<222> LOCATION: (4759)..(4759)
<223> OTHER INFORMATION: a, c, g, or t
<220> FEATURE:
<221> NAME/KEY: modified_base
<222> LOCATION: (4766)..(4766)
<223> OTHER INFORMATION: a, c, g, or t
<220> FEATURE:
<221> NAME/KEY: modified_base
<222> LOCATION: (4773)..(4773)
<223> OTHER INFORMATION: a, c, g, or t
<220> FEATURE:
<221> NAME/KEY: modified_base
<222> LOCATION: (4780)..(4782)
<223> OTHER INFORMATION: a, c, g, or t
<220> FEATURE:
<221> NAME/KEY: modified_base
<222> LOCATION: (4784)..(4784)
<223> OTHER INFORMATION: a, c, g, or t
<220> FEATURE:
<221> NAME/KEY: modified_base
<222> LOCATION: (4790)..(4792)
<223> OTHER INFORMATION: a, c, g, or t
<220> FEATURE:
<221> NAME/KEY: modified_base
<222> LOCATION: (4795)..(4795)
<223> OTHER INFORMATION: a, c, g, or t
<220> FEATURE:
<221> NAME/KEY: modified_base
<222> LOCATION: (4802)..(4803)
<223> OTHER INFORMATION: a, c, g, or t
<220> FEATURE:
<221> NAME/KEY: modified_base
<222> LOCATION: (4810)..(4810)
<223> OTHER INFORMATION: a, c, g, or t
<220> FEATURE:
<221> NAME/KEY: modified_base
<222> LOCATION: (4813)..(4813)
<223> OTHER INFORMATION: a, c, g, or t
<220> FEATURE:
<221> NAME/KEY: modified_base
<222> LOCATION: (4820)..(4820)
<223> OTHER INFORMATION: a, c, g, or t
<220> FEATURE:
<221> NAME/KEY: modified_base
<222> LOCATION: (4822)..(4822)
<223> OTHER INFORMATION: a, c, g, or t
<220> FEATURE:
<221> NAME/KEY: modified_base
<222> LOCATION: (4830)..(4830)
<223> OTHER INFORMATION: a, c, g, or t
<220> FEATURE:
<221> NAME/KEY: modified_base
<222> LOCATION: (4839)..(4839)
<223> OTHER INFORMATION: a, c, g, or t
<220> FEATURE:
<221> NAME/KEY: modified_base
<222> LOCATION: (4843)..(4843)
<223> OTHER INFORMATION: a, c, g, or t
<220> FEATURE:
<221> NAME/KEY: modified_base
<222> LOCATION: (4845)..(4845)
<223> OTHER INFORMATION: a, c, g, or t
<220> FEATURE:
<221> NAME/KEY: modified_base
<222> LOCATION: (4847)..(4847)
<223> OTHER INFORMATION: a, c, g, or t
<220> FEATURE:
<221> NAME/KEY: modified_base
<222> LOCATION: (4851)..(4851)
<223> OTHER INFORMATION: a, c, g, or t
<220> FEATURE:
<221> NAME/KEY: modified_base
<222> LOCATION: (4854)..(4854)
<223> OTHER INFORMATION: a, c, g, or t
<220> FEATURE:
<221> NAME/KEY: modified_base
<222> LOCATION: (4858)..(4858)
```

```
<223> OTHER INFORMATION: a, c, g, or t
<220> FEATURE:
<221> NAME/KEY: modified_base
<222> LOCATION: (4865)..(4865)
<223> OTHER INFORMATION: a, c, g, or t
<220> FEATURE:
<221> NAME/KEY: modified_base
<222> LOCATION: (4880)..(4882)
<223> OTHER INFORMATION: a, c, g, or t
<220> FEATURE:
<221> NAME/KEY: modified_base
<222> LOCATION: (4885)..(4885)
<223> OTHER INFORMATION: a, c, g, or t
<220> FEATURE:
<221> NAME/KEY: modified_base
<222> LOCATION: (4887)..(4887)
<223> OTHER INFORMATION: a, c, g, or t
<220> FEATURE:
<221> NAME/KEY: modified_base
<222> LOCATION: (4891)..(4891)
<223> OTHER INFORMATION: a, c, g, or t
<220> FEATURE:
<221> NAME/KEY: modified_base
<222> LOCATION: (4893)..(4893)
<223> OTHER INFORMATION: a, c, g, or t
<220> FEATURE:
<221> NAME/KEY: modified_base
<222> LOCATION: (4895)..(4895)
<223> OTHER INFORMATION: a, c, g, or t
<220> FEATURE:
<221> NAME/KEY: modified_base
<222> LOCATION: (4901)..(4901)
<223> OTHER INFORMATION: a, c, g, or t
<220> FEATURE:
<221> NAME/KEY: modified_base
<222> LOCATION: (4906)..(4906)
<223> OTHER INFORMATION: a, c, g, or t
<220> FEATURE:
<221> NAME/KEY: modified_base
<222> LOCATION: (4927)..(4927)
<223> OTHER INFORMATION: a, c, g, or t
<220> FEATURE:
<221> NAME/KEY: modified_base
<222> LOCATION: (4931)..(4931)
<223> OTHER INFORMATION: a, c, g, or t
<220> FEATURE:
<221> NAME/KEY: modified_base
<222> LOCATION: (4933)..(4933)
<223> OTHER INFORMATION: a, c, g, or t
<220> FEATURE:
<221> NAME/KEY: modified_base
<222> LOCATION: (4937)..(4937)
<223> OTHER INFORMATION: a, c, g, or t
<220> FEATURE:
<221> NAME/KEY: modified_base
<222> LOCATION: (4942)..(4942)
<223> OTHER INFORMATION: a, c, g, or t
<220> FEATURE:
<221> NAME/KEY: modified_base
<222> LOCATION: (4945)..(4945)
<223> OTHER INFORMATION: a, c, g, or t
<220> FEATURE:
<221> NAME/KEY: modified_base
<222> LOCATION: (4949)..(4949)
<223> OTHER INFORMATION: a, c, g, or t
<220> FEATURE:
<221> NAME/KEY: modified_base
<222> LOCATION: (4951)..(4952)
<223> OTHER INFORMATION: a, c, g, or t
<220> FEATURE:
<221> NAME/KEY: modified_base
<222> LOCATION: (4954)..(4954)
<223> OTHER INFORMATION: a, c, g, or t
<220> FEATURE:
<221> NAME/KEY: modified_base
<222> LOCATION: (4958)..(4958)
<223> OTHER INFORMATION: a, c, g, or t
<220> FEATURE:
<221> NAME/KEY: modified_base
```

```
<222> LOCATION: (4965)..(4965)
<223> OTHER INFORMATION: a, c, g, or t
<220> FEATURE:
<221> NAME/KEY: modified_base
<222> LOCATION: (4968)..(4968)
<223> OTHER INFORMATION: a, c, g, or t
<220> FEATURE:
<221> NAME/KEY: modified_base
<222> LOCATION: (4970)..(4970)
<223> OTHER INFORMATION: a, c, g, or t
<220> FEATURE:
<221> NAME/KEY: modified_base
<222> LOCATION: (4975)..(4975)
<223> OTHER INFORMATION: a, c, g, or t
<220> FEATURE:
<221> NAME/KEY: modified_base
<222> LOCATION: (4982)..(4982)
<223> OTHER INFORMATION: a, c, g, or t
<220> FEATURE:
<221> NAME/KEY: modified_base
<222> LOCATION: (4989)..(4989)
<223> OTHER INFORMATION: a, c, g, or t
<220> FEATURE:
<221> NAME/KEY: modified_base
<222> LOCATION: (4994)..(4994)
<223> OTHER INFORMATION: a, c, g, or t

<400> SEQUENCE: 8
ctcaagcata cggacaaggg taaataacat agtcaccaga acataataaa caaaaagtgc      60
agaagcaaga taaaaaaatt agctatggac attcaggttc atattggaaa catcattatc     120
ctagtcttgt gaccatcctt cctcctgctc tagttgagag gccttgggac taacgagagg     180
tcagttggga tagcagatcc ttatcctgga ctagcctttc tggtgtttca gagtcttcgt     240
gccgccgtct acatctatct ccattaggtc tgaagatgac tcttcacacc aacgacgttt     300
aaggtctcta tcctactcct agcttgcaat acctggcttg caatacctgg agcatcgtgc     360
acgatgattg gatactgtgg aggaggagtg tttgctgatt tagagctccc ggttgggtga     420
tttgacttcg atttcagttt aggcttgttg aaattttttca ggttccattg tgaagccttt     480
agagcttgag cttccttcca tgttaatgcc ttgatcgaat tctcctagag aaaagggaag     540
tcgatctctg agtattgaaa tcgaagtgca cattttttt caacgtgtcc aatcaatcca     600
caaacaaagc agaagacagg taatctttca tacttatact gacaagtaat agtcttaccg     660
tcatgcataa taacgtctcg ttccttcaag aggggttttc cgacatccat aacgacccga     720
agcctcatga aagcattagg gaagaacttt tggttcttct tgtcatggcc tttataggtg     780
tcagccgagc tcgccaattc ccgtccgact ggctccgcaa atattcgaa cggcaagtta     840 tggacttgca accataactc cacggtattg agcaggacct attgtgaaga ctcatctcat     900
ggagcttcag aatgtggttg tcagcaaacc aatgaccgaa atccatcaca tgacggacgt     960
ccagtgggtg agcgaaacga acaggaagc gcctatcttt cagagtcgtg agctccacac    1020
cggattccgg caactacgtg ttgggcaggc ttcgccgtat tagagatatg ttgaggcaag    1080
acccatctgt gccactcgta caattacgag agttgttttt tttgtgattt tcctaagttt    1140
ctcgttgatg gtgagctcat attctacatc gtatggtctc tcaacgtcgt ttcctgtcat    1200
ctgatatccc gtcatttgca tccacgtgcg ccgcctcccg tgccaagtcc ctaggtgtca    1260
tgcacgccaa attggtggtg gtgcgggctg ccctgtgctt cttaccgatg ggtgcgaggtt    1320 gagtttgggg gtctccgcgg cgatggtagt gggttgacgg tttggtgtgg gttgacggca    1380
ttgatcaatt tacttcttgc ttcaaattct ttggcagaaa acaattcatt agattagaac    1440
tggaaaccag agtgatgaga cggattaagt cagattccaa cagagttaca tctcttaaga    1500
```

-continued

```
aataatgtaa ccccttttaga ctttatatat ttgcaattaa aaaaataatt taacttttag    1560
actttatata tagttttaat aactaagttt aaccactcta ttatttatat cgaaactatt    1620
tgtatgtctc ccctctaaat aaacttggta ttgtgtttac agaacctata atcaaataat    1680
caatactcaa ctgaagtttg tgcagttaat tgaagggatt aacggccaaa atgcactagt    1740
attatcaacc gaatagattc acactagatg gccatttcca tcaatatcat cgccgttctt    1800
cttctgtcca catatcccct ctgaaacttg agagacacct gcacttcatt gtccttatta    1860
cgtgttacaa aatgaaaccc atgcatccat gcaaactgaa gaatggcgca agaaccttc     1920 ccctccattt cttatgtggc gaccatccat ttcaccatct cccgctataa aacaccccca    1980
```

```
tcacttcacc tagaacatca tcactacttg cttatccatc caaagatac ccacc atg      2038
                                                           Met
                                                            1 gct aga tca tca agc cct ttg ctt ctc tca ctc tgc att ttc gcc att     2086
Ala Arg Ser Ser Ser Pro Leu Leu Leu Ser Leu Cys Ile Phe Ala Ile
             5                  10                  15 ctc ttc cac tct tct ctg ggt agg cag caa ttc cag cag ggg aac gag     2134
Leu Phe His Ser Ser Leu Gly Arg Gln Gln Phe Gln Gln Gly Asn Glu
         20                  25                  30 tgc cag atc gac agg atc gac gca tcc gag ccg gac aaa acc atc cag     2182
Cys Gln Ile Asp Arg Ile Asp Ala Ser Glu Pro Asp Lys Thr Ile Gln
     35                  40                  45 gca gaa gct ggc acc atc gag gta tgg gac cag aac cgc cag caa ttc     2230
Ala Glu Ala Gly Thr Ile Glu Val Trp Asp Gln Asn Arg Gln Gln Phe
 50                  55                  60                  65 cag tgc gct ggt gtt gcc gtt gta agg cgc acc att gag ccc aaa ggt     2278
Gln Cys Ala Gly Val Ala Val Val Arg Arg Thr Ile Glu Pro Lys Gly
                 70                  75                  80 ctt ctc ttg cct ttc tac agc aac acc cct cag ctc atc tac atc gtt     2326
Leu Leu Leu Pro Phe Tyr Ser Asn Thr Pro Gln Leu Ile Tyr Ile Val
             85                  90                  95 caa ggtataaatt aaatcagttc atacaatgat aaccaccact tcgaatgtat           2379
Gln ttatcaaata tcaatgatcg atgcacctgt atgtgttgtg tatattca ggt agg gga    2436
                                                     Gly Arg Gly
                                                             100 gtt aca gga atc atg ttc cca kga tgt cca gag aca ttc gag gaa tcc     2484
Val Thr Gly Ile Met Phe Pro Xaa Cys Pro Glu Thr Phe Glu Glu Ser
             105                 110                 115 cag cag caa gga caa cag ggc caa cag ggt agt tcc caa gac cag cac     2532
Gln Gln Gln Gly Gln Gln Gly Gln Gln Gly Ser Ser Gln Asp Gln His
             120                 125                 130 cag aag atc cgc cgc ttc cgt gaa ggt gac gtc att gcc gtc cct gcc     2580
Gln Lys Ile Arg Arg Phe Arg Glu Gly Asp Val Ile Ala Val Pro Ala
     135                 140                 145 ggt gta gcc cac tgg tcc tac aac gat ggc aac gaa cca gtc atg gcc     2628
Gly Val Ala His Trp Ser Tyr Asn Asp Gly Asn Glu Pro Val Met Ala
150                 155                 160                 165 att gtt gtc cat gac act tcc agc cac ctc aac caa ctg gac aac aac     2676
Ile Val Val His Asp Thr Ser Ser His Leu Asn Gln Leu Asp Asn Asn
                 170                 175                 180 ccc agg gtatataagc attgccgtag ttgctaataa attgcacaca attggaactc      2732
Pro Arg tattttcagt atctaataac ttttttccttt tttggcag aac ttc tac ttg gca gga  2788
                                         Asn Phe Tyr Leu Ala Gly
                                                             185 aac ccg aga gac gag ttc gaa caa tcg cag caa gga ggc agg ctg agc     2836
```

```
                Asn Pro Arg Asp Glu Phe Glu Gln Ser Gln Gln Gly Gly Arg Leu Ser
                190                 195                 200                 205 cgt ggg gag agt gaa ggt gga cga gga cgc agg gaa cct ctt caa cct        2884
Arg Gly Glu Ser Glu Gly Gly Arg Gly Arg Arg Glu Pro Leu Gln Pro
                210                 215                 220 gca aca acc tct tct tgc gga atc gac tcc aag ctc atc gcg gag gcg        2932
Ala Thr Thr Ser Ser Cys Gly Ile Asp Ser Lys Leu Ile Ala Glu Ala
                225                 230                 235 ttc aat gtc gac gag aac gtg gca agg agg cta cag agc gag aac gac        2980
Phe Asn Val Asp Glu Asn Val Ala Arg Arg Leu Gln Ser Glu Asn Asp
                240                 245                 250 aac aga ggc cag atc gtc cga gtc gaa ggc gag ctc gac atc gtc aga        3028
Asn Arg Gly Gln Ile Val Arg Val Glu Gly Glu Leu Asp Ile Val Arg
                255                 260                 265 cct ccg acc agt atc cag gag gag tca cag gag cag gga ggt cgt ggt        3076
Pro Pro Thr Ser Ile Gln Glu Glu Ser Gln Glu Gln Gly Gly Arg Gly
270                 275                 280                 285 ggt ggc cgc tac tac tcc aat gga gtg gag gag acc ttc tgc tcc atg        3124
Gly Gly Arg Tyr Tyr Ser Asn Gly Val Glu Glu Thr Phe Cys Ser Met
                290                 295                 300 aga cta att gag aac atc ggc gat cct tct cgg gca gac att ttc act        3172
Arg Leu Ile Glu Asn Ile Gly Asp Pro Ser Arg Ala Asp Ile Phe Thr
                305                 310                 315 cca gaa gcc ggc cgc gtt aga tcc ctc aac agc cac aac ctc ccc gtc        3220
Pro Glu Ala Gly Arg Val Arg Ser Leu Asn Ser His Asn Leu Pro Val
                320                 325                 330 ctg caa tgg atc cag ctt agc gcc gag aga ggc gtt ctc tac aat           3265
Leu Gln Trp Ile Gln Leu Ser Ala Glu Arg Gly Val Leu Tyr Asn
335                 340                 345 gtatagatct cactcacgca ccaactctaa attgaatccc taattattta attcaccgat     3325
atctgaccga ccggtttgaa ttttgtag gaa gcg atc agg ctg ccg cac tgg        3377
                                Glu Ala Ile Arg Leu Pro His Trp
                                350                 355 aac atc aac gca cac agc ata gtg tac gcg atc aga gga caa gcc aga      3425
Asn Ile Asn Ala His Ser Ile Val Tyr Ala Ile Arg Gly Gln Ala Arg
                360                 365                 370 gtc cag atc gtg aac gag gaa ggg aat tcg gtg ttc gat gga gtg ctg     3473
Val Gln Ile Val Asn Glu Glu Gly Asn Ser Val Phe Asp Gly Val Leu
                375                 380                 385 cag gaa gga cag gtg gtg acg gtg ccg cag aac ttc gcg gtg gta aag     3521
Gln Glu Gly Gln Val Val Thr Val Pro Gln Asn Phe Ala Val Val Lys
                390                 395                 400 aga tcc cag agc gag agg ttt gag tgg gtg gcg ttc aag acc aac gac     3569
Arg Ser Gln Ser Glu Arg Phe Glu Trp Val Ala Phe Lys Thr Asn Asp
405                 410                 415                 420 aac gcg atg gtg aac tcg cta gcc ggg agg aca tcg gca gta agg gcg     3617
Asn Ala Met Val Asn Ser Leu Ala Gly Arg Thr Ser Ala Val Arg Ala
                425                 430                 435 atc ccc gcg gat gta ctg gct aac gcc tgg agg gtg tcg ccg gag gag     3665
Ile Pro Ala Asp Val Leu Ala Asn Ala Trp Arg Val Ser Pro Glu Glu
                440                 445                 450 gcg agg agg gtg aag ttc aac agg cag gag act cac ttg gct agc acc     3713
Ala Arg Arg Val Lys Phe Asn Arg Gln Glu Thr His Leu Ala Ser Thr
                455                 460                 465 agg ggc cag tcc agg tcg ccc ggg agg ttg aat gtc gtc aag gag gtg     3761
Arg Gly Gln Ser Arg Ser Pro Gly Arg Leu Asn Val Val Lys Glu Val
                470                 475                 480 atc aac ttg ctt atg taa aatgtgacgg tgaaataata acggtaaaat             3809
Ile Asn Leu Leu Met
```

-continued

```
485 atatgtaata ataataataa taaagccaca aagtgagaat gaggggaagg ggaaatgtgt    3869 aatgagccag tagccggtgg tgctaatttt gtatcgtatt gtcaataaat catgaatttt    3929 gtggttttta tgtgtttttt taaatcatga attttaaatt ttataaaata atctccaatc    3989 ggaagaacaa cattccatat ccatggatgt ttctttaccc aaatctagtt cttgagagga    4049 tgaagcatca ccgaacagtt ctgcaactat ccctcaaaag ctttaaaatg aacaacaagg    4109 aacagagcaa cgttccaaag atcccaaacg aaacatatta tctatactaa tactatatta    4169 ttaattacta ctgcccggaa tcacaatccc tgaatgattc ctattaacta caagccttgt    4229 tggcggcgga gaagtgatcg gcgcggcgag aagcagcgga ctcggagacg aggccttgga    4289 tgagcagagt ctttacctgc cagggcgtga aggggaagag cggccttctg gagtaggagt    4349 tcagcaagcg gcggttcctt ggcggagtaa gcggacgtaa gggtggntgt cgacgtcntc    4409 gtttcnggag gcgnattcat gaaggttaa agtcanatct gtagctctcg agtgctcagg    4469 gagccnaaag acgttgggaa accgtcgncg tttgggcat cagtcngcgg ggcacgcttc    4529 cctcctgctg ctccanaanc nangtanatt taaaagannat gggaaattaa ntaatggnaa    4589 tnannaggag gattgnaacg gtcngancgc nangaanagt ttttanggt ttaaatactg    4649 ggggagtngn agccngccnc tggttccngt gtagangaaa ccaagnnccg ggaggntnc    4709 annngnnagg gagaaaaagg anncatttna nnangcngag ggacatgaan cggtacngag    4769 ctgnggttca nnnancggcg nnnggnagtc ccnngggacc nggntggggt nanaagggaa    4829 nggaacattn ggtngnangg anaanaccnt tttacnattg cctttgcagg nnngtntngg    4889 cncntncggg tnacatnccg ctgcatgggc tttgggngc cnanaggnag ccncangggn    4949 anncngccnc cttgtncang ncgctnaagt tcnattgtan atggncgttg              4999
```

```
<210> SEQ ID NO 9
<211> LENGTH: 98
<212> TYPE: PRT
<213> ORGANISM: Linum usitatissimum

<400> SEQUENCE: 9
```

```
Met Ala Arg Ser Ser Pro Leu Leu Leu Ser Leu Cys Ile Phe Ala
1               5                   10                  15

Ile Leu Phe His Ser Ser Leu Gly Arg Gln Gln Phe Gln Gln Gly Asn
            20                  25                  30

Glu Cys Gln Ile Asp Arg Ile Asp Ala Ser Glu Pro Asp Lys Thr Ile
        35                  40                  45

Gln Ala Glu Ala Gly Thr Ile Glu Val Trp Asp Gln Asn Arg Gln Gln
    50                  55                  60

Phe Gln Cys Ala Gly Val Ala Val Val Arg Arg Thr Ile Glu Pro Lys
65                  70                  75                  80

Gly Leu Leu Leu Pro Phe Tyr Ser Asn Thr Pro Gln Leu Ile Tyr Ile
                85                  90                  95

Val Gln
```

```
<210> SEQ ID NO 10
<211> LENGTH: 85
<212> TYPE: PRT
<213> ORGANISM: Linum usitatissimum
<220> FEATURE:
<221> NAME/KEY: MOD_RES
<222> LOCATION: (11)..(11)
<223> OTHER INFORMATION: Gly or stop codon (amino acid may not be
``` present)

<400> SEQUENCE: 10

| Gly | Arg | Gly | Val | Thr | Gly | Ile | Met | Phe | Pro | Xaa | Cys | Pro | Glu | Thr | Phe |
|---|---|---|---|---|---|---|---|---|---|---|---|---|---|---|---|
| 1 | | | | 5 | | | | | 10 | | | | | 15 | |

| Glu | Glu | Ser | Gln | Gln | Gly | Gln | Gln | Gly | Gln | Gln | Gly | Ser | Ser | Gln |
|---|---|---|---|---|---|---|---|---|---|---|---|---|---|---|
| | | | 20 | | | | | 25 | | | | | 30 | |

| Asp | Gln | His | Gln | Lys | Ile | Arg | Arg | Phe | Arg | Glu | Gly | Asp | Val | Ile | Ala |
|---|---|---|---|---|---|---|---|---|---|---|---|---|---|---|---|
| | | 35 | | | | | 40 | | | | | 45 | | | |

| Val | Pro | Ala | Gly | Val | Ala | His | Trp | Ser | Tyr | Asn | Asp | Gly | Asn | Glu | Pro |
|---|---|---|---|---|---|---|---|---|---|---|---|---|---|---|---|
| | 50 | | | | | 55 | | | | | 60 | | | | |

| Val | Met | Ala | Ile | Val | Val | His | Asp | Thr | Ser | Ser | His | Leu | Asn | Gln | Leu |
|---|---|---|---|---|---|---|---|---|---|---|---|---|---|---|---|
| 65 | | | | | 70 | | | | | 75 | | | | | 80 |

| Asp | Asn | Asn | Pro | Arg |
|---|---|---|---|---|
| | | | | 85 |

<210> SEQ ID NO 11
<211> LENGTH: 165
<212> TYPE: PRT
<213> ORGANISM: Linum usitatissimum

<400> SEQUENCE: 11

| Asn | Phe | Tyr | Leu | Ala | Gly | Asn | Pro | Arg | Asp | Glu | Phe | Glu | Gln | Ser | Gln |
|---|---|---|---|---|---|---|---|---|---|---|---|---|---|---|---|
| 1 | | | | 5 | | | | | 10 | | | | | 15 | |

| Gln | Gly | Gly | Arg | Leu | Ser | Arg | Gly | Glu | Ser | Glu | Gly | Gly | Arg | Gly | Arg |
|---|---|---|---|---|---|---|---|---|---|---|---|---|---|---|---|
| | | | 20 | | | | | 25 | | | | | 30 | | |

| Arg | Glu | Pro | Leu | Gln | Pro | Ala | Thr | Thr | Ser | Ser | Cys | Gly | Ile | Asp | Ser |
|---|---|---|---|---|---|---|---|---|---|---|---|---|---|---|---|
| | | 35 | | | | | 40 | | | | | 45 | | | |

| Lys | Leu | Ile | Ala | Glu | Ala | Phe | Asn | Val | Asp | Glu | Asn | Val | Ala | Arg | Arg |
|---|---|---|---|---|---|---|---|---|---|---|---|---|---|---|---|
| | 50 | | | | | 55 | | | | | 60 | | | | |

| Leu | Gln | Ser | Glu | Asn | Asp | Asn | Arg | Gly | Gln | Ile | Val | Arg | Val | Glu | Gly |
|---|---|---|---|---|---|---|---|---|---|---|---|---|---|---|---|
| 65 | | | | | 70 | | | | | 75 | | | | | 80 |

| Glu | Leu | Asp | Ile | Val | Arg | Pro | Pro | Thr | Ser | Ile | Gln | Glu | Glu | Ser | Gln |
|---|---|---|---|---|---|---|---|---|---|---|---|---|---|---|---|
| | | | | 85 | | | | | 90 | | | | | 95 | |

| Glu | Gln | Gly | Gly | Arg | Gly | Gly | Arg | Tyr | Tyr | Ser | Asn | Gly | Val | Glu |
|---|---|---|---|---|---|---|---|---|---|---|---|---|---|---|
| | | | 100 | | | | | 105 | | | | | 110 | |

| Glu | Thr | Phe | Cys | Ser | Met | Arg | Leu | Ile | Glu | Asn | Ile | Gly | Asp | Pro | Ser |
|---|---|---|---|---|---|---|---|---|---|---|---|---|---|---|---|
| | | | 115 | | | | | 120 | | | | | 125 | | |

| Arg | Ala | Asp | Ile | Phe | Thr | Pro | Glu | Ala | Gly | Arg | Val | Arg | Ser | Leu | Asn |
|---|---|---|---|---|---|---|---|---|---|---|---|---|---|---|---|
| | 130 | | | | | 135 | | | | | 140 | | | | |

| Ser | His | Asn | Leu | Pro | Val | Leu | Gln | Trp | Ile | Gln | Leu | Ser | Ala | Glu | Arg |
|---|---|---|---|---|---|---|---|---|---|---|---|---|---|---|---|
| 145 | | | | | 150 | | | | | 155 | | | | | 160 |

| Gly | Val | Leu | Tyr | Asn |
|---|---|---|---|---|
| | | | | 165 |

<210> SEQ ID NO 12
<211> LENGTH: 141
<212> TYPE: PRT
<213> ORGANISM: Linum usitatissimum

<400> SEQUENCE: 12

| Glu | Ala | Ile | Arg | Leu | Pro | His | Trp | Asn | Ile | Asn | Ala | His | Ser | Ile | Val |
|---|---|---|---|---|---|---|---|---|---|---|---|---|---|---|---|
| 1 | | | | 5 | | | | | 10 | | | | | 15 | |

| Tyr | Ala | Ile | Arg | Gly | Gln | Ala | Arg | Val | Gln | Ile | Val | Asn | Glu | Glu | Gly |
|---|---|---|---|---|---|---|---|---|---|---|---|---|---|---|---|
| | | | 20 | | | | | 25 | | | | | 30 | | |

| Asn | Ser | Val | Phe | Asp | Gly | Val | Leu | Gln | Glu | Gly | Gln | Val | Val | Thr | Val |
|---|---|---|---|---|---|---|---|---|---|---|---|---|---|---|---|
| | | 35 | | | | | 40 | | | | | 45 | | | |

```
Pro Gln Asn Phe Ala Val Val Lys Arg Ser Gln Ser Glu Arg Phe Glu
    50                  55                  60

Trp Val Ala Phe Lys Thr Asn Asp Asn Ala Met Val Asn Ser Leu Ala
 65                  70                  75                  80

Gly Arg Thr Ser Ala Val Arg Ala Ile Pro Ala Asp Val Leu Ala Asn
                 85                  90                  95

Ala Trp Arg Val Ser Pro Glu Glu Ala Arg Arg Val Lys Phe Asn Arg
                100                 105                 110

Gln Glu Thr His Leu Ala Ser Thr Arg Gly Gln Ser Arg Ser Pro Gly
            115                 120                 125

Arg Leu Asn Val Val Lys Glu Val Ile Asn Leu Leu Met
        130                 135                 140

<210> SEQ ID NO 13
<211> LENGTH: 11
<212> TYPE: PRT
<213> ORGANISM: Linum usitatissimum

<400> SEQUENCE: 13

Gln Gln Gln Gly Gln Gln Gln Gly Gln Gln Gln
  1               5                  10

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tccactatgt aggtcata                                                18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctttaaggtg tgagagtc                                                18

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aggggtgatc gatta                                                   15

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```

```
gatagaaccc acacgagc                                                   18

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tatctagact caagcatacg gacaagggt                                       29

<210> SEQ ID NO 19
<211> LENGTH: 6
<212> TYPE: DNA
<213> ORGANISM: Artificial Sequence
<220> FEATURE:
<223> OTHER INFORMATION: Description of Artificial Sequence: Synthetic
      XbaI site

<400> SEQUENCE: 19 tctaga                                                                 6

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggttatcatt gtatgaactg a                                               21

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: Synthetic
      NcoI site

<400> SEQUENCE: 21 ccatgg                                                                 6

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcaagcttaa tgtgacggtg aaataataac gg                                   32

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: Synthetic
      HindIII site

<400> SEQUENCE: 23
```

```
aagctt                                                                     6

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
taggtacctg gcaggtaaag actctgctc                                           29

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: Synthetic
      KpnI site

<400> SEQUENCE: 25 ggtacc                                                                     6
```